(12) United States Patent
Hartmann et al.

(10) Patent No.: US 8,815,503 B2
(45) Date of Patent: Aug. 26, 2014

(54) COMPOSITIONS AND METHODS FOR IMMUNOSTIMULATORY RNA OLIGONUCLEOTIDES

(75) Inventors: Gunther Hartmann, Bonn (DE); Veit Hornung, Pullach (DE)

(73) Assignee: Rheinische Friedrich-Wilhelms-Universitat Bonn, Bonn (DE)

( * ) Notice: Subject to any disclaimer, the term of this patent is extended or adjusted under 35 U.S.C. 154(b) by 971 days.

(21) Appl. No.: 12/066,906

(22) PCT Filed: Sep. 14, 2006

(86) PCT No.: PCT/EP2006/008972
§ 371 (c)(1),
(2), (4) Date: Nov. 7, 2008

(87) PCT Pub. No.: WO2007/031319
PCT Pub. Date: Mar. 22, 2007

(65) Prior Publication Data
US 2009/0111765 A1  Apr. 30, 2009

Related U.S. Application Data

(60) Provisional application No. 60/717,359, filed on Sep. 15, 2005.

(30) Foreign Application Priority Data

Sep. 14, 2005 (EP) .................................... 05020019

(51) Int. Cl.
| | | |
|---|---|---|
| C12Q 1/68 | (2006.01) | |
| A61K 39/39 | (2006.01) | |
| C07H 21/02 | (2006.01) | |
| C07H 21/04 | (2006.01) | |
| A61K 38/20 | (2006.01) | |

(52) U.S. Cl.
CPC ............... *A61K 39/39* (2013.01); *A61K 38/208* (2013.01)
USPC ........................... 435/6.1; 536/23.1; 536/24.5

(58) Field of Classification Search
None
See application file for complete search history.

(56) References Cited

U.S. PATENT DOCUMENTS

| 5,643,771 | A | 7/1997 | Stocker |
|---|---|---|---|
| 5,824,538 | A | 10/1998 | Branstrom et al. |
| 6,004,815 | A | 12/1999 | Portnoy et al. |
| 6,713,457 | B2 | 3/2004 | Farrar et al. |
| 6,747,014 | B2 | 6/2004 | Teng et al. |
| 2003/0113293 | A1 | 6/2003 | Bermudes et al. |
| 2004/0002077 | A1 | 1/2004 | Taira et al. |
| 2005/0118193 | A1 | 6/2005 | Andino-Pavlovsky et al. |
| 2008/0233651 | A1 | 9/2008 | Kreutzer et al. |

FOREIGN PATENT DOCUMENTS

| WO | 98/44131 | 10/1998 |
|---|---|---|
| WO | WO 03/086280 A2 | 10/2003 |
| WO | WO 2004/004743 A1 | 1/2004 |

OTHER PUBLICATIONS

Martinez et al., Single-stranded antisense siRNAs guide target RNA cleavage in RNAi, 2002, Cell, vol. 110, pp. 563-574.*
Barchet et al., "Dendritic cells respond to influenza virus through TLR7- and PKR-independent pathways," Eur J Immunol 35: 236-242, 2005.
Heil et al., "Species-Specific Recognition of Single-Stranded RNA via Toll-like Receptor 7 and 8," Science 303: 1526-1529, Mar. 5, 2004.
Hornung et al., "Sequence-specific potent induction of IFN-α by short interfering RNA in plasmacytoid dendritic cells through TLR7," Nature Medicine 11(3): 263-270, Mar. 2005.
Judge et al., "Sequence-dependent stimulation of the mammalian innate immune response by synthetic siRNA," Nature Biotechnology 23(4): 457-462, Apr. 2005.
Liu et al., "Small interference RNA modulation of IL-10 in human monocyte-derived dendritic cells enhances the Th1 response," Eur J Immunol 34: 1680-1687, 2004.
Lochmann et al., "Drug delivery of oligonucleotides by peptides," European Journal of Pharmaceutics and Biopharmaceutics 58: 237-251, 2004.
Schlee et al., "siRNA and isRNA: Two Edges of One Sword," Molecular Therapy 14(4): 463-470, Oct. 2006.
Sioud, "Induction of Inflammatory Cytokines and Interferon Responses by Double-stranded and Single-stranded siRNAs is Sequence-dependent and Requires Endosomal Localization," J Mol Biol 348: 1079-1090, 2005.
Sugiyama et al., "CpG RNA: Identification of Novel Single-Stranded RNA That Stimulates Human CD14+CD11c+ Monocytes," The Journal of Immunology 174: 2273-2279, 2005.
Ventura et al., Biochem and Biophys Res Comm, 203(2):889-898 (1994). "Ribozyme targeting of HIV-1 LTR."
Courvalin et al., Nature Biotechnology, 16 (1998). "Functional gene transfer from intracellular bacteria to mammalian cells."
Wagner et al., J Biol Chem, 269:12918-12924 (1994). "The influence of endosome-disruptive peptides on gene transfer using synthetic virus-like gene transfer systems."

(Continued)

*Primary Examiner* — Dana Shin
(74) *Attorney, Agent, or Firm* — Leydig, Voit & Mayer, Ltd.

(57) ABSTRACT

The present invention provides 4-nucleotide (4mer) RNA motifs that confer immunostimulatory activity, in particular, IL-12-inducing activity to a single-stranded RNA oligonucleotide. The present invention also provides single-stranded RNA oligonucleotides, including antisense RNA, with high or low immunostimulatory activity. The present invention further provides the use of the RNA oligonucleotides of the invention for therapeutic purposes.

14 Claims, 41 Drawing Sheets

(56) References Cited

OTHER PUBLICATIONS

Puttaraju et al., J. Biological Chemistry, 271(42):26081-26087 (1996). "Circular ribozymes generated in *Escherichia coli* using group I self-splicing permuted intron-exon sequences."

Dawson et al., J Theor Biol, 201:113-140 (1999). "Mean free energy topology for nucleotide sequences of varying composition based on secondary structure calculations."

Tung et al., Frontiers in Bioscience, 3:a11-15 (1998). "Targeted inhibition of hepatitis B virus gene expression: a gene therapy approach."

Robbins, et al., Nature Biotechnology, 24(5):566-571 (2006). "Stable expression of shRNAs in human CD34+ progenitor cells can avoid induction of interferon responses to siRNAs in vitro."

Perez-Ruiz, M. et al., Antisense Nucleic Acid Drug Dev, 9(1):33-42 (1999). "The antisense sequence of the HIV-1 TAR stem-loop structure covalently linked to the hairpin ribozyme enhances its catalytic activity against two artificial substrates."

Misquitta, L. and Paterson, B.M., Proc Natl Acad Sci USA, 96(4):1451-1456 (1999). "Targeted disruption of gene function in *Drosophila* by RNA interference (RNA-i): a role for nautilus in embryonic stomatic muscle formation."

Gaughan et al., FEBS Letters, 374:241-245 (1995). "Ribozyme mediated cleavage of acute phase serum amyloid A (A-SAA) mRNA in vitro."

Timmons et al., Nature, 395:854 (1998). "Specific interference by ingested dsRNA."

Vollmer et al., *J. Exp. Med.*, 202(11): 1575-1585 (2005).

\* cited by examiner

SEQUENCE LISTING

<160> NUMBER OF SEQ ID NOS: 712

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaaaaa aaaaaaaaa                                              19

<210> SEQ ID NO 2
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 2
aaaaaaaaca aaaaaaaa                                                    19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaga aaaaaaaa                                                    19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaaaua aaaaaaaa                                                    19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaacc aaaaaaaa                                                    19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaaaaaacg aaaaaaaa                                                    19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaaaaaacu aaaaaaaa                                                    19

<210> SEQ ID NO 8
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
aaaaaaaagc aaaaaaaaa                                                   19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaaaaaagg aaaaaaaaa                                                   19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
aaaaaaaagu aaaaaaaaa                                                   19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaaaaaauc aaaaaaaaa                                                   19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaaaaaug aaaaaaaaa                                                   19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaaaaaauu aaaaaaaaa                                                   19

<210> SEQ ID NO 14
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 14
aaaaaaaaca caaaaaaaa                                                      19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aaaaaaaaca gaaaaaaaa                                                      19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
aaaaaaaaca uaaaaaaaa                                                      19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaaaaaacc caaaaaaaa                                                      19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaaaaaacc gaaaaaaaa                                                      19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaaaaaacc uaaaaaaaa                                                      19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 20
aaaaaaaacg caaaaaaa                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaaaaaacg gaaaaaaa                                                    19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aaaaaaaacg uaaaaaaa                                                    19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aaaaaaaacu caaaaaaa                                                    19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
aaaaaaaacu gaaaaaaa                                                    19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaaaaaacu uaaaaaaa                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 26
aaaaaaaaga caaaaaaaa                                              19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aaaaaaaaga gaaaaaaaa                                              19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aaaaaaaaga uaaaaaaaa                                              19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
aaaaaaaagc caaaaaaaa                                              19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
aaaaaaaagc gaaaaaaaa                                              19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aaaaaaaagc uaaaaaaaa                                              19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 32
aaaaaaaagg caaaaaaaa                                               19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aaaaaaaagg gaaaaaaaa                                               19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
aaaaaaaagg uaaaaaaaa                                               19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aaaaaaaagu caaaaaaaa                                               19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aaaaaaaagu gaaaaaaaa                                               19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aaaaaaaagu uaaaaaaaa                                               19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
```
aaaaaaaaua caaaaaaaa                                                    19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aaaaaaaaua gaaaaaaaa                                                    19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aaaaaaaaua uaaaaaaaa                                                    19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
aaaaaaaauc caaaaaaaa                                                    19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aaaaaaaauc gaaaaaaaa                                                    19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aaaaaaaauc uaaaaaaaa                                                    19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
aaaaaaaaug caaaaaaaa                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aaaaaaaaug gaaaaaaaa                                                    19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aaaaaaaaug uaaaaaaaa                                                    19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aaaaaaaauu caaaaaaaa                                                    19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
aaaaaaaauu gaaaaaaaa                                                    19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aaaaaaaauu uaaaaaaaa                                                    19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
aaaaaaacaa caaaaaaaa                                                    19

```
<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aaaaaaacaa gaaaaaaaa                                                   19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
aaaaaaacaa uaaaaaaaa                                                   19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
aaaaaaacac caaaaaaaa                                                   19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
aaaaaaacac gaaaaaaaa                                                   19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
aaaaaaacac uaaaaaaaa                                                   19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
aaaaaaacag caaaaaaaa                                                   19
```

```
<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aaaaaaacag gaaaaaaaa                                                 19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
aaaaaaacag uaaaaaaaa                                                 19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aaaaaaacau caaaaaaaa                                                 19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aaaaaaacau gaaaaaaaa                                                 19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aaaaaaacau uaaaaaaaa                                                 19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aaaaaaacca caaaaaaaa                                                 19
```

```
<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
aaaaaaacca gaaaaaaaa                                                        19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
aaaaaaacca uaaaaaaaa                                                        19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
aaaaaaaccc caaaaaaaa                                                        19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
aaaaaaaccc gaaaaaaaa                                                        19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
aaaaaaaccc uaaaaaaaa                                                        19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
aaaaaaaccg caaaaaaaa                                                        19

<210> SEQ ID NO 69
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
aaaaaaaccg gaaaaaaaa                                                       19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
aaaaaaaccg uaaaaaaaa                                                       19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aaaaaaaccu caaaaaaaa                                                       19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
aaaaaaaccu gaaaaaaaa                                                       19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aaaaaaaccu uaaaaaaaa                                                       19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aaaaaaacga caaaaaaaa                                                       19

<210> SEQ ID NO 75
<211> LENGTH: 19
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
aaaaaaacga gaaaaaaaa                                                   19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
aaaaaaacga uaaaaaaaa                                                   19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
aaaaaaacgc caaaaaaaa                                                   19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aaaaaaacgc gaaaaaaaa                                                   19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
aaaaaaacgc uaaaaaaaa                                                   19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
aaaaaaacgg caaaaaaaa                                                   19

<210> SEQ ID NO 81
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 81
aaaaaaacgg gaaaaaaaa                                              19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
aaaaaaacgg uaaaaaaaa                                              19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
aaaaaaacgu caaaaaaaa                                              19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
aaaaaaacgu gaaaaaaaa                                              19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
aaaaaaacgu uaaaaaaaa                                              19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
aaaaaaacua caaaaaaaa                                              19

<210> SEQ ID NO 87
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 87
aaaaaaacua gaaaaaaaa                                                    19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
aaaaaaacua uaaaaaaaa                                                    19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
aaaaaaacuc caaaaaaaa                                                    19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
aaaaaaacuc gaaaaaaaa                                                    19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
aaaaaaacuc uaaaaaaaa                                                    19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
aaaaaaacug caaaaaaaa                                                    19

<210> SEQ ID NO 93
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 93
aaaaaaacug gaaaaaaaa                                                    19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
aaaaaaacug uaaaaaaaa                                                    19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aaaaaaacuu caaaaaaaa                                                    19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
aaaaaaacuu gaaaaaaaa                                                    19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
aaaaaaacuu uaaaaaaaa                                                    19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aaaaaaagaa caaaaaaaa                                                    19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 99
aaaaaaagaa gaaaaaaa                                                19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
aaaaaaagaa uaaaaaaa                                                19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
aaaaaaagac caaaaaaa                                                19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aaaaaaagac gaaaaaaa                                                19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
aaaaaaagac uaaaaaaa                                                19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
aaaaaaagag caaaaaaa                                                19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
aaaaaaagag gaaaaaaaa                                          19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
aaaaaaagag uaaaaaaaa                                          19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
aaaaaaagau caaaaaaaa                                          19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
aaaaaaagau gaaaaaaaa                                          19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
aaaaaaagau uaaaaaaaa                                          19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
aaaaaaagca caaaaaaaa                                          19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 111
aaaaaaagca gaaaaaaaa                                                  19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
aaaaaaagca uaaaaaaaa                                                  19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
aaaaaaagcc caaaaaaaa                                                  19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
aaaaaaagcc gaaaaaaaa                                                  19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
aaaaaaagcc uaaaaaaaa                                                  19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
aaaaaaagcg caaaaaaaa                                                  19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
```
aaaaaaagcg gaaaaaaaa                                        19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
aaaaaaagcg uaaaaaaaa                                        19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
aaaaaaagcu caaaaaaaa                                        19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
aaaaaaagcu gaaaaaaaa                                        19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
aaaaaaagcu uaaaaaaaa                                        19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
aaaaaaagga caaaaaaaa                                        19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
aaaaaaagga gaaaaaaaa                          19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
aaaaaaagga uaaaaaaaa                          19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
aaaaaaaggc caaaaaaaa                          19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
aaaaaaaggc gaaaaaaaa                          19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
aaaaaaaggc uaaaaaaaa                          19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
aaaaaaaggg caaaaaaaa                          19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
aaaaaaaggg gaaaaaaaa                          19

```
<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
aaaaaaaggg uaaaaaaa                                                       19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
aaaaaaaggu caaaaaaa                                                       19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
aaaaaaaggu gaaaaaaa                                                       19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
aaaaaaaggu uaaaaaaa                                                       19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
aaaaaaagua caaaaaaa                                                       19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
aaaaaaagua gaaaaaaa                                                       19
```

```
<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
aaaaaaagua uaaaaaaa                                                    19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
aaaaaaaguc caaaaaaa                                                    19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
aaaaaaaguc gaaaaaaa                                                    19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
aaaaaaaguc uaaaaaaa                                                    19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aaaaaaagug caaaaaaa                                                    19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
aaaaaaagug gaaaaaaa                                                    19
```

```
<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
aaaaaaagug uaaaaaaa                                                   19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
aaaaaaaguu caaaaaaa                                                   19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
aaaaaaaguu gaaaaaaa                                                   19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
aaaaaaaguu uaaaaaaa                                                   19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
aaaaaaauaa caaaaaaa                                                   19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
aaaaaaauaa gaaaaaaa                                                   19

<210> SEQ ID NO 148
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
aaaaaaauaa uaaaaaaa                                                19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
aaaaaaauac caaaaaaa                                                19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
aaaaaaauac gaaaaaaa                                                19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
aaaaaaauac uaaaaaaa                                                19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
aaaaaaauag caaaaaaa                                                19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
aaaaaaauag gaaaaaaa                                                19

<210> SEQ ID NO 154
<211> LENGTH: 19
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
aaaaaaauag uaaaaaaa                                              19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
aaaaaaauau caaaaaaa                                              19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
aaaaaaauau gaaaaaaa                                              19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aaaaaaauau uaaaaaaa                                              19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
aaaaaaauca caaaaaaa                                              19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
aaaaaaauca gaaaaaaa                                              19

<210> SEQ ID NO 160
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 160
aaaaaaauca uaaaaaaa                                                     19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
aaaaaaaucc caaaaaaa                                                     19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
aaaaaaaucc gaaaaaaa                                                     19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
aaaaaaaucc uaaaaaaa                                                     19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
aaaaaaaucg caaaaaaa                                                     19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aaaaaaaucg gaaaaaaa                                                     19

<210> SEQ ID NO 166
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 166
aaaaaaaucg uaaaaaaaa                                              19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
aaaaaaaucu caaaaaaaa                                              19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
aaaaaaaucu gaaaaaaaa                                              19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aaaaaaaucu uaaaaaaaa                                              19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
aaaaaaauga caaaaaaaa                                              19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
aaaaaaauga gaaaaaaaa                                              19

<210> SEQ ID NO 172
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 172
aaaaaaauga uaaaaaaaa                                                       19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aaaaaaaugc caaaaaaaa                                                       19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
aaaaaaaugc gaaaaaaaa                                                       19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
aaaaaaaugc uaaaaaaaa                                                       19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
aaaaaaaugg caaaaaaaa                                                       19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
aaaaaaaugg gaaaaaaaa                                                       19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 178
aaaaaaaugg uaaaaaaa                          19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
aaaaaaaugu caaaaaaa                          19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
aaaaaaaugu gaaaaaaa                          19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
aaaaaaaugu uaaaaaaa                          19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
aaaaaaauua caaaaaaa                          19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
aaaaaaauua gaaaaaaa                          19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 184
aaaaaaauua uaaaaaaaa                                              19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aaaaaaauuc caaaaaaaa                                              19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
aaaaaaauuc gaaaaaaaa                                              19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
aaaaaaauuc uaaaaaaaa                                              19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
aaaaaaauug caaaaaaaa                                              19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
aaaaaaauug gaaaaaaaa                                              19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 190
aaaaaaauug uaaaaaaa                                                   19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
aaaaaaauuu caaaaaaa                                                   19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
aaaaaaauuu gaaaaaaa                                                   19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
aaaaaaauuu uaaaaaaa                                                   19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
agcuuaaccu guccuucaa                                                  19

<210> SEQ ID NO 195
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ggugcaucga ugcagggggg                                                 20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
```
aacgcccggc ucauuacguc                                              20

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
uugauguguu uagucgcua                                               19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gcaccacuag uugguuguc                                               19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
ugcuauuggu gauugccuc                                               19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
guuguaguug uacuccagc                                               19

<210> SEQ ID NO 201
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
guugugguug ugguugug                                                18

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
aaaaaaaucg uaaaaaaaa                                                19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
aaaucguaaa aaaaaaaa                                                 19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
aaaaaaaaaa aaucguaaa                                                19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
aaaucguaaa aaucguaaa                                                19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ucguaaaucg uaaaucgua                                                19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
augguaaagu ugaaaucgu                                                19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
augguaaugg uaaaguuga                                                19

```
<210> SEQ ID NO 209
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
aaaugauaaa gguaaaaugg caaaugguaa aguugaaauc guaaa              45

<210> SEQ ID NO 210
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
aaaugauggc aaaaaa                                              16

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gcaccacuag uugguuguc                                           19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
ugcuauuggu gauugccuc                                           19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
guuguaguug uacuccagc                                           19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
uaccuaaccg gacauaauc                                           19
```

```
<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uaaaccuucg auuccgacc                                                19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
uagcgacuaa acgcaucaa                                                19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
auacgcucag acaaagcug                                                19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
auacgcucac acaaagcug                                                19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
cuaauacagg ccaauacau                                                19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
uagcgacuaa acacaucaa                                                19
```

```
<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
uaaaccuuua gcuccgacc                                                    19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
auaccaggcu ccaaagcug                                                    19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
uagcgacuaa gcgcaucaa                                                    19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
auacgcucag ccaaagcug                                                    19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
aaggcagcac gacuucuuc                                                    19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
uuuauaaguu ugcuggugc                                                    19

<210> SEQ ID NO 227
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
uuguuuguau ggcuauccg                                                  19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
uugcucucgu gugugguau                                                  19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uugcguuguu ggagugguc                                                  19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
uguguuguug gcucuacaa                                                  19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uguagugguc gguggcccc                                                  19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
uguagugaag uuguguccg                                                  19

<210> SEQ ID NO 233
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ugaguuggug gacuguuug                                                19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ucucguuggu uacguuacu                                                19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
uaugguguuu cguauaugu                                                19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
gacccaacac acacgggcc                                                19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
aaaacaaaac ggaacccag                                                19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
aaaaaccaac ccaagaucu                                                19

<210> SEQ ID NO 239
<211> LENGTH: 19
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 239
uuagggcaaa ccaccagac                                                  19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
cagaccaacg gaacgcgca                                                  19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
cggcccacca acccggacu                                                  19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
cccaagagag acgaaacgc                                                  19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
uaccacaggc ccaaacggc                                                  19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
auccgagaaa cuaccacca                                                  19

<210> SEQ ID NO 245
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 245
cccaauaaca caaagccua                                                      19

<210> SEQ ID NO 246
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
aaagguuaaa aaagguuaaa                                                     20

<210> SEQ ID NO 247
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
aaauuguaaa aaagguuaaa                                                     20

<210> SEQ ID NO 248
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
aaauugcaaa aaagguuaaa                                                     20

<210> SEQ ID NO 249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
aaaugcuaaa aaagguuaaa                                                     20

<210> SEQ ID NO 250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
aaaugauaaa aaagguuaaa                                                     20

<210> SEQ ID NO 251
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 251 aagguaaaa aaagguuaaa                                                    20

<210> SEQ ID NO 252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
aaauggcaaa aaagguuaaa                                                   20

<210> SEQ ID NO 253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
aaaugguaaa aaagguuaaa                                                   20

<210> SEQ ID NO 254
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
aaaguugaaa aaagguuaaa                                                   20

<210> SEQ ID NO 255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
aaaucguaaa aaagguuaaa                                                   20

<210> SEQ ID NO 256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
aaagguuaaa aaauuguaaa                                                   20

<210> SEQ ID NO 257
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 257
aaauuguaaa aaauuguaaa                                          20

<210> SEQ ID NO 258
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
aaauugcaaa aaauuguaaa                                          20

<210> SEQ ID NO 259
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
aaaugcuaaa aaauuguaaa                                          20

<210> SEQ ID NO 260
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
aaaugauaaa aaauuguaaa                                          20

<210> SEQ ID NO 261
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
aaagguaaaa aaauuguaaa                                          20

<210> SEQ ID NO 262
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
aaauggcaaa aaauuguaaa                                          20

<210> SEQ ID NO 263
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263 aaauggugaaa aaauuguaaa                                          20

<210> SEQ ID NO 264
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
aaaguugaaa aaauuguaaa                                           20

<210> SEQ ID NO 265
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
aaaucguaaa aaauuguaaa                                           20

<210> SEQ ID NO 266
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
aaagguuaaa aaauugcaaa                                           20

<210> SEQ ID NO 267
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
aaauuguaaa aaauugcaaa                                           20

<210> SEQ ID NO 268
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
aaauugcaaa aaauugcaaa                                           20

<210> SEQ ID NO 269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 269
aaaugcuaaa aaauugcaaa                                              20

<210> SEQ ID NO 270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
aaaugauaaa aaauugcaaa                                              20

<210> SEQ ID NO 271
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
aaagguaaaa aaauugcaaa                                              20

<210> SEQ ID NO 272
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
aaauggcaaa aaauugcaaa                                              20

<210> SEQ ID NO 273
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
aaaugguaaa aaauugcaaa                                              20

<210> SEQ ID NO 274
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
aaaguugaaa aaauugcaaa                                              20

<210> SEQ ID NO 275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
```
aaaucguaaa aaauugcaaa                                                    20

<210> SEQ ID NO 276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
aaagguuaaa aaaugcuaaa                                                    20

<210> SEQ ID NO 277
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
aaauuguaaa aaaugcuaaa                                                    20

<210> SEQ ID NO 278
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
aaauugcaaa aaaugcuaaa                                                    20

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
aaaugcuaaa aaaugcuaaa                                                    20

<210> SEQ ID NO 280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
aaaugauaaa aaaugcuaaa                                                    20

<210> SEQ ID NO 281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
aaagguaaaa aaaugcuaaa                                          20

<210> SEQ ID NO 282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
aaauggcaaa aaaugcuaaa                                          20

<210> SEQ ID NO 283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
aaaugguaaa aaaugcuaaa                                          20

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
aaaguugaaa aaaugcuaaa                                          20

<210> SEQ ID NO 285
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
aaaucguaaa aaaugcuaaa                                          20

<210> SEQ ID NO 286
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
aaagguuaaa aaaugauaaa                                          20

<210> SEQ ID NO 287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
aaauuguaaa aaaugauaaa                                          20

<210> SEQ ID NO 288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
aaauugcaaa aaaugauaaa                                              20

<210> SEQ ID NO 289
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
aaaugcuaaa aaaugauaaa                                              20

<210> SEQ ID NO 290
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
aaaugauaaa aaaugauaaa                                              20

<210> SEQ ID NO 291
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
aaagguaaaa aaaugauaaa                                              20

<210> SEQ ID NO 292
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
aaauggcaaa aaaugauaaa                                              20

<210> SEQ ID NO 293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
aaaugguaaa aaaugauaaa                                              20

```
<210> SEQ ID NO 294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
aaaguugaaa aaaugauaaa                                              20

<210> SEQ ID NO 295
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
aaaucguaaa aaaugauaaa                                              20

<210> SEQ ID NO 296
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
aaagguuaaa aaagguaaaa                                              20

<210> SEQ ID NO 297
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
aaauuguaaa aaagguaaaa                                              20

<210> SEQ ID NO 298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
aaauugcaaa aaagguaaaa                                              20

<210> SEQ ID NO 299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
aaaugcuaaa aaagguaaaa                                              20
```

```
<210> SEQ ID NO 300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
aaaugauaaa aaagguaaaa                                              20

<210> SEQ ID NO 301
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
aaagguaaaa aaagguaaaa                                              20

<210> SEQ ID NO 302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
aaauggcaaa aaagguaaaa                                              20

<210> SEQ ID NO 303
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
aaaugguaaa aaagguaaaa                                              20

<210> SEQ ID NO 304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
aaaguugaaa aaagguaaaa                                              20

<210> SEQ ID NO 305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
aaaucguaaa aaagguaaaa                                              20

<210> SEQ ID NO 306
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
aaagguuaaa aaauggcaaa                                               20

<210> SEQ ID NO 307
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
aaauuguaaa aaauggcaaa                                               20

<210> SEQ ID NO 308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
aaauugcaaa aaauggcaaa                                               20

<210> SEQ ID NO 309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
aaaugcuaaa aaauggcaaa                                               20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
aaaugauaaa aaauggcaaa                                               20

<210> SEQ ID NO 311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
aaagguaaaa aaauggcaaa                                               20

<210> SEQ ID NO 312
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
aaauggcaaa aaauggcaaa                                                   20

<210> SEQ ID NO 313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
aaaugguaaa aaauggcaaa                                                   20

<210> SEQ ID NO 314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
aaaguugaaa aaauggcaaa                                                   20

<210> SEQ ID NO 315
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aaaucguaaa aaauggcaaa                                                   20

<210> SEQ ID NO 316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
aaagguuaaa aaaugguaaa                                                   20

<210> SEQ ID NO 317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
aaauuguaaa aaaugguaaa                                                   20

<210> SEQ ID NO 318
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 318
aaauugcaaa aaaugguaaa                                              20

<210> SEQ ID NO 319
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
aaaugcuaaa aaaugguaaa                                              20

<210> SEQ ID NO 320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
aaaugauaaa aaaugguaaa                                              20

<210> SEQ ID NO 321
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
aaagguaaaa aaaugguaaa                                              20

<210> SEQ ID NO 322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
aaauggcaaa aaaugguaaa                                              20

<210> SEQ ID NO 323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
aaaugguaaa aaaugguaaa                                              20

<210> SEQ ID NO 324
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 324
aaaguugaaa aaaugguaaa                                                   20

<210> SEQ ID NO 325
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
aaaucguaaa aaaugguaaa                                                   20

<210> SEQ ID NO 326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
aaagguuaaa aaaguugaaa                                                   20

<210> SEQ ID NO 327
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
aaauuguaaa aaaguugaaa                                                   20

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
aaauugcaaa aaaguugaaa                                                   20

<210> SEQ ID NO 329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
aaaugcuaaa aaaguugaaa                                                   20

<210> SEQ ID NO 330
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 330
aaaugauaaa aaaguugaaa                                              20

<210> SEQ ID NO 331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
aaagguaaaa aaaguugaaa                                              20

<210> SEQ ID NO 332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
aaauggcaaa aaaguugaaa                                              20

<210> SEQ ID NO 333
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
aaaugguaaa aaaguugaaa                                              20

<210> SEQ ID NO 334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
aaaguugaaa aaaguugaaa                                              20

<210> SEQ ID NO 335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
aaaucguaaa aaaguugaaa                                              20

<210> SEQ ID NO 336
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 336
aaagguuaaa aaaucguaaa                                               20

<210> SEQ ID NO 337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
aaauuguaaa aaaucguaaa                                               20

<210> SEQ ID NO 338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
aaauugcaaa aaaucguaaa                                               20

<210> SEQ ID NO 339
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
aaaugcuaaa aaaucguaaa                                               20

<210> SEQ ID NO 340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
aaaugauaaa aaaucguaaa                                               20

<210> SEQ ID NO 341
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
aaagguaaaa aaaucguaaa                                               20

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 342
aaauggcaaa aaaucguaaa                                              20

<210> SEQ ID NO 343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343 aaauggbuaaa aaaucguaaa                                             20

<210> SEQ ID NO 344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
aaaguugaaa aaaucguaaa                                              20

<210> SEQ ID NO 345
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
aaaucguaaa aaaucguaaa                                              20

<210> SEQ ID NO 346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
aaaguucaaa aaagguuaaa                                              20

<210> SEQ ID NO 347
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
aaagucaaaa aaagguuaaa                                              20

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 348
aaagcucaaa aaagguuaaa                                              20

<210> SEQ ID NO 349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
aaaguugaaa aaagguuaaa                                              20

<210> SEQ ID NO 350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
aaaguuuaaa aaagguuaaa                                              20

<210> SEQ ID NO 351
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
aaagguuaaa aaagguuaaa                                              20

<210> SEQ ID NO 352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aaaguguaaa aaagguuaaa                                              20

<210> SEQ ID NO 353
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
aaaggucaaa aaagguuaaa                                              20

<210> SEQ ID NO 354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
```
aaagucuaaa aaagguuaaa                                                    20

<210> SEQ ID NO 355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
aaaguccaaa aaagguuaaa                                                    20

<210> SEQ ID NO 356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
aaaguucaaa aaauuguaaa                                                    20

<210> SEQ ID NO 357
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
aaagucaaaa aaauuguaaa                                                    20

<210> SEQ ID NO 358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
aaagcucaaa aaauuguaaa                                                    20

<210> SEQ ID NO 359
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
aaaguugaaa aaauuguaaa                                                    20

<210> SEQ ID NO 360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360

-continued aaaguuuaaa aaauuguaaa                                              20

<210> SEQ ID NO 361
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
aaagguuaaa aaauuguaaa                                              20

<210> SEQ ID NO 362
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
aaaguguaaa aaauuguaaa                                              20

<210> SEQ ID NO 363
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
aaaggucaaa aaauuguaaa                                              20

<210> SEQ ID NO 364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
aaagucuaaa aaauuguaaa                                              20

<210> SEQ ID NO 365
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
aaaguccaaa aaauuguaaa                                              20

<210> SEQ ID NO 366
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
aaaguucaaa aaauugcaaa                                              20

<210> SEQ ID NO 367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
aaagucaaaa aaauugcaaa                                              20

<210> SEQ ID NO 368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
aaagcucaaa aaauugcaaa                                              20

<210> SEQ ID NO 369
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
aaaguugaaa aaauugcaaa                                              20

<210> SEQ ID NO 370
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
aaaguuuaaa aaauugcaaa                                              20

<210> SEQ ID NO 371
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
aaagguuaaa aaauugcaaa                                              20

<210> SEQ ID NO 372
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
aaaguguaaa aaauugcaaa                                              20

```
<210> SEQ ID NO 373
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
aaaggucaaa aaauugcaaa                                                     20

<210> SEQ ID NO 374
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
aaagucuaaa aaauugcaaa                                                     20

<210> SEQ ID NO 375
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
aaaguccaaa aaauugcaaa                                                     20

<210> SEQ ID NO 376
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aaaguucaaa aaaugcuaaa                                                     20

<210> SEQ ID NO 377
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
aaagucaaaa aaaugcuaaa                                                     20

<210> SEQ ID NO 378
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
aaagcucaaa aaaugcuaaa                                                     20
```

```
<210> SEQ ID NO 379
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
aaaguugaaa aaaugcuaaa                                                    20

<210> SEQ ID NO 380
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
aaaguuuaaa aaaugcuaaa                                                    20

<210> SEQ ID NO 381
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
aaagguuaaa aaaugcuaaa                                                    20

<210> SEQ ID NO 382
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
aaaguguaaa aaaugcuaaa                                                    20

<210> SEQ ID NO 383
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
aaaggucaaa aaaugcuaaa                                                    20

<210> SEQ ID NO 384
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
aaagucuaaa aaaugcuaaa                                                    20

<210> SEQ ID NO 385
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
aaaguccaaa aaaugcuaaa                                                   20

<210> SEQ ID NO 386
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aaaguucaaa aaaugauaaa                                                   20

<210> SEQ ID NO 387
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
aaagucaaaa aaaugauaaa                                                   20

<210> SEQ ID NO 388
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
aaagcucaaa aaaugauaaa                                                   20

<210> SEQ ID NO 389
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
aaaguugaaa aaaugauaaa                                                   20

<210> SEQ ID NO 390
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
aaaguuuaaa aaaugauaaa                                                   20

<210> SEQ ID NO 391
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
aaagguuaaa aaaugauaaa                                              20

<210> SEQ ID NO 392
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
aaaguguaaa aaaugauaaa                                              20

<210> SEQ ID NO 393
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
aaaggucaaa aaaugauaaa                                              20

<210> SEQ ID NO 394
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
aaagucuaaa aaaugauaaa                                              20

<210> SEQ ID NO 395
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
aaaguccaaa aaaugauaaa                                              20

<210> SEQ ID NO 396
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
aaaguucaaa aaagguaaaa                                              20

<210> SEQ ID NO 397
<211> LENGTH: 20
<212> TYPE: RNA
```

<213> ORGANISM: Artificial Sequence
<220> FEATURE:
<223> OTHER INFORMATION: Description of Artificial Sequence: Synthetic
    oligonucleotide

<400> SEQUENCE: 397
aaagucaaaa aaagguaaaa                                                20

<210> SEQ ID NO 398
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 398
aaagcucaaa aaagguaaaa                                                20

<210> SEQ ID NO 399
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 399
aaaguugaaa aaagguaaaa                                                20

<210> SEQ ID NO 400
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 400
aaaguuuaaa aaagguaaaa                                                20

<210> SEQ ID NO 401
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 401
aaagguuaaa aaagguaaaa                                                20

<210> SEQ ID NO 402
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 402
aaaguguaaa aaagguaaaa                                                20

<210> SEQ ID NO 403
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
aaaggucaaa aaagguaaaa                                               20

<210> SEQ ID NO 404
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
aaagucuaaa aaagguaaaa                                               20

<210> SEQ ID NO 405
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
aaaguccaaa aaagguaaaa                                               20

<210> SEQ ID NO 406
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
aaaguucaaa aaauggcaaa                                               20

<210> SEQ ID NO 407
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
aaagucaaaa aaauggcaaa                                               20

<210> SEQ ID NO 408
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
aaagcucaaa aaauggcaaa                                               20

<210> SEQ ID NO 409
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 409
aaaguugaaa aaauggcaaa                                              20

<210> SEQ ID NO 410
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
aaaguuuaaa aaauggcaaa                                              20

<210> SEQ ID NO 411
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
aaagguuaaa aaauggcaaa                                              20

<210> SEQ ID NO 412
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
aaaguguaaa aaauggcaaa                                              20

<210> SEQ ID NO 413
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
aaaggucaaa aaauggcaaa                                              20

<210> SEQ ID NO 414
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
aaagucuaaa aaauggcaaa                                              20

<210> SEQ ID NO 415
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 415
aaaguccaaa aaauggcaaa                                               20

<210> SEQ ID NO 416
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
aaaguucaaa aaaugguaaa                                               20

<210> SEQ ID NO 417
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
aaagucaaaa aaaugguaaa                                               20

<210> SEQ ID NO 418
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
aaagcucaaa aaaugguaaa                                               20

<210> SEQ ID NO 419
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
aaaguugaaa aaaugguaaa                                               20

<210> SEQ ID NO 420
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
aaaguuuaaa aaaugguaaa                                               20

<210> SEQ ID NO 421
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
aaagguuaaa aaauugguaaa                                              20

<210> SEQ ID NO 422
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
aaaguguaaa aaauugguaaa                                              20

<210> SEQ ID NO 423
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
aaaggucaaa aaauugguaaa                                              20

<210> SEQ ID NO 424
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
aaagucuaaa aaauugguaaa                                              20

<210> SEQ ID NO 425
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
aaaguccaaa aaauugguaaa                                              20

<210> SEQ ID NO 426
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
aaaguucaaa aaaguugaaa                                               20

<210> SEQ ID NO 427
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 427
aaagucaaaa aaaguugaaa                                          20

<210> SEQ ID NO 428
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
aaagcucaaa aaaguugaaa                                          20

<210> SEQ ID NO 429
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
aaaguugaaa aaaguugaaa                                          20

<210> SEQ ID NO 430
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
aaaguuuaaa aaaguugaaa                                          20

<210> SEQ ID NO 431
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
aaagguuaaa aaaguugaaa                                          20

<210> SEQ ID NO 432
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
aaaguguaaa aaaguugaaa                                          20

<210> SEQ ID NO 433
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
```

```
aaaggucaaa aaaguugaaa                                          20

<210> SEQ ID NO 434
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
aaagucuaaa aaaguugaaa                                          20

<210> SEQ ID NO 435
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
aaaguccaaa aaaguugaaa                                          20

<210> SEQ ID NO 436
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
aaaguucaaa aaaucguaaa                                          20

<210> SEQ ID NO 437
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
aaagucaaaa aaaucguaaa                                          20

<210> SEQ ID NO 438
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
aaagcucaaa aaaucguaaa                                          20

<210> SEQ ID NO 439
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
```
aaaguugaaa aaaucguaaa					20

<210> SEQ ID NO 440
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
aaaguuuaaa aaaucguaaa					20

<210> SEQ ID NO 441
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
aaagguuaaa aaaucguaaa					20

<210> SEQ ID NO 442
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
aaaguguaaa aaaucguaaa					20

<210> SEQ ID NO 443
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
aaaggucaaa aaaucguaaa					20

<210> SEQ ID NO 444
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
aaagucuaaa aaaucguaaa					20

<210> SEQ ID NO 445
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
aaaguccaaa aaaucguaaa					20

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
uugaaggaca gguuaagcu                                              19

<210> SEQ ID NO 447
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 447

Arg Arg Arg Arg Arg Arg Arg Arg Arg Arg Arg Arg Arg Arg Arg Arg
1               5                   10                  15

Arg Arg Arg Arg Arg Arg Arg Arg
            20

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
aaaaaaaaug guaaaaaaa                                              19

<210> SEQ ID NO 449
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
agcuuaaccu guccuu                                                 16

<210> SEQ ID NO 450
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
uuaaccuguc cuucaa                                                 16

<210> SEQ ID NO 451
<211> LENGTH: 12
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 451
agcuuaaccu gu                                                            12

<210> SEQ ID NO 452
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
accuguccuu ca                                                            12

<210> SEQ ID NO 453
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
uugaaggaca uguccuucaa                                                    20

<210> SEQ ID NO 454
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uggaaggaca uguccuucaa                                                    20

<210> SEQ ID NO 455
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
uguaaggaca uguccuucaa                                                    20

<210> SEQ ID NO 456
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
ugucaggaca uguccuucaa                                                    20

<210> SEQ ID NO 457
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 457
uguccugaca uguccuucaa                                           20

<210> SEQ ID NO 458
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uguccuuaca uguccuucaa                                           20

<210> SEQ ID NO 459
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
uguccuucaa uguccuucaa                                           20

<210> SEQ ID NO 460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
aaaaaaaacc gaaaaaaaa                                            19

<210> SEQ ID NO 461
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
aaaaaaacac caaaaaaaa                                            19

<210> SEQ ID NO 462
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
aaaaaaaacg caaaaaaaa                                            19

<210> SEQ ID NO 463
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 463
aaaaaaacaa gaaaaaaaa                                              19

<210> SEQ ID NO 464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
aaaaaaacca caaaaaaaa                                              19

<210> SEQ ID NO 465
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
aaaaaaaagc caaaaaaaa                                              19

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
aaaaaaaagg aaaaaaaaa                                              19

<210> SEQ ID NO 467
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
aaaaaaaacc caaaaaaaa                                              19

<210> SEQ ID NO 468
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
aaaaaaacga gaaaaaaaa                                              19

<210> SEQ ID NO 469
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 469
aaaaaaaaca gaaaaaaaa                                                  19

<210> SEQ ID NO 470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
aaaaaaacac gaaaaaaaa                                                  19

<210> SEQ ID NO 471
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
aaaaaaacgg caaaaaaaa                                                  19

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
aaaaaaagac gaaaaaaaa                                                  19

<210> SEQ ID NO 473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
aaaaaaaauc gaaaaaaaa                                                  19

<210> SEQ ID NO 474
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
aaaaaaacaa caaaaaaaa                                                  19

<210> SEQ ID NO 475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
```

-continued aaaaaaaccg gaaaaaaaa                                                   19

<210> SEQ ID NO 476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
aaaaaaaggg caaaaaaaa                                                   19

<210> SEQ ID NO 477
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
aaaaaaaaca caaaaaaaa                                                   19

<210> SEQ ID NO 478
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
aaaaaaaacg gaaaaaaaa                                                   19

<210> SEQ ID NO 479
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
aaaaaaaaga aaaaaaaaa                                                   19

<210> SEQ ID NO 480
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
aaaaaaagcg gaaaaaaaa                                                   19

<210> SEQ ID NO 481
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
aaaaaaaacg aaaaaaaaa                                                19

<210> SEQ ID NO 482
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
aaaaaaacgg gaaaaaaaa                                                19

<210> SEQ ID NO 483
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
aaaaaaagag gaaaaaaaa                                                19

<210> SEQ ID NO 484
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
aaaaaaaccc gaaaaaaaa                                                19

<210> SEQ ID NO 485
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
aaaaaaaaga gaaaaaaaa                                                19

<210> SEQ ID NO 486
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
aaaaaaaagg caaaaaaaa                                                19

<210> SEQ ID NO 487
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
aaaaaaacgc caaaaaaaa                                                19

<210> SEQ ID NO 488
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
aaaaaaaacc aaaaaaaaa                                                19

<210> SEQ ID NO 489
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
aaaaaaagag caaaaaaaa                                                19

<210> SEQ ID NO 490
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
aaaaaaagaa gaaaaaaaa                                                19

<210> SEQ ID NO 491
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
aaaaaaaagc aaaaaaaaa                                                19

<210> SEQ ID NO 492
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
aaaaaaacag gaaaaaaaa                                                19

<210> SEQ ID NO 493
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
aaaaaaagac caaaaaaaa                                                19

```
<210> SEQ ID NO 494
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
aaaaaaaaga caaaaaaaa                                                  19

<210> SEQ ID NO 495
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
aaaaaaacga caaaaaaaa                                                  19

<210> SEQ ID NO 496
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
aaaaaaagaa caaaaaaaa                                                  19

<210> SEQ ID NO 497
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
aaaaaaaagc gaaaaaaaa                                                  19

<210> SEQ ID NO 498
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
aaaaaaaagg gaaaaaaaa                                                  19

<210> SEQ ID NO 499
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
aaaaaaaccc caaaaaaaa                                                  19
```

```
<210> SEQ ID NO 500
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
aaaaaaacgc gaaaaaaaa                                                      19

<210> SEQ ID NO 501
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
aaaaaaagcc gaaaaaaaa                                                      19

<210> SEQ ID NO 502
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
aaaaaaagcg caaaaaaaa                                                      19

<210> SEQ ID NO 503
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
aaaaaaagca caaaaaaaa                                                      19

<210> SEQ ID NO 504
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
aaaaaaaaca aaaaaaaaa                                                      19

<210> SEQ ID NO 505
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
aaaaaaacca gaaaaaaaa                                                      19

<210> SEQ ID NO 506
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
aaaaaaaccg caaaaaaaa                                                      19

<210> SEQ ID NO 507
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
aaaaaaaacu aaaaaaaaa                                                      19

<210> SEQ ID NO 508
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
aaaaaaaccu caaaaaaaa                                                      19

<210> SEQ ID NO 509
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
aaaaaaacag caaaaaaaa                                                      19

<210> SEQ ID NO 510
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
aaaaaaaggc gaaaaaaaa                                                      19

<210> SEQ ID NO 511
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
aaaaaaaggc caaaaaaaa                                                      19

<210> SEQ ID NO 512
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
aaaaaaagcc caaaaaaaa                                                19

<210> SEQ ID NO 513
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
aaaaaaacuc gaaaaaaaa                                                19

<210> SEQ ID NO 514
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
aaaaaaacac uaaaaaaaa                                                19

<210> SEQ ID NO 515
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
aaaaaaagga gaaaaaaaa                                                19

<210> SEQ ID NO 516
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
aaaaaaaacc uaaaaaaaa                                                19

<210> SEQ ID NO 517
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
aaaaaaaggg gaaaaaaaa                                                19

<210> SEQ ID NO 518
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 518
aaaaaaaccu gaaaaaaaa                                              19

<210> SEQ ID NO 519
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
aaaaaaaucc gaaaaaaaa                                              19

<210> SEQ ID NO 520
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
aaaaaaagcu caaaaaaaa                                              19

<210> SEQ ID NO 521
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
aaaaaaaaaa aaaaaaaaa                                              19

<210> SEQ ID NO 522
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
aaaaaaacau caaaaaaaa                                              19

<210> SEQ ID NO 523
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
aaaaaaaacu gaaaaaaaa                                              19

<210> SEQ ID NO 524
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 524
aaaaaaaauc caaaaaaaa                                                       19

<210> SEQ ID NO 525
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
aaaaaaacua caaaaaaaa                                                       19

<210> SEQ ID NO 526
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
aaaaaaacau gaaaaaaaa                                                       19

<210> SEQ ID NO 527
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
aaaaaaaauu caaaaaaaa                                                       19

<210> SEQ ID NO 528
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
aaaaaaaggg uaaaaaaaa                                                       19

<210> SEQ ID NO 529
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
aaaaaaagga caaaaaaaa                                                       19

<210> SEQ ID NO 530
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 530
aaaaaaaauc aaaaaaaaa                                                       19

<210> SEQ ID NO 531
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
aaaaaaaucc caaaaaaaa                                                       19

<210> SEQ ID NO 532
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
aaaaaaacuc caaaaaaaa                                                       19

<210> SEQ ID NO 533
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
aaaaaaaacu caaaaaaaa                                                       19

<210> SEQ ID NO 534
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
aaaaaaaaua aaaaaaaaa                                                       19

<210> SEQ ID NO 535
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
aaaaaaauca caaaaaaaa                                                       19

<210> SEQ ID NO 536
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 536
aaaaaaacuu caaaaaaaa					19

<210> SEQ ID NO 537
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
aaaaaaagcu gaaaaaaaa					19

<210> SEQ ID NO 538
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
aaaaaaacca uaaaaaaaa					19

<210> SEQ ID NO 539
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
aaaaaaacaa uaaaaaaaa					19

<210> SEQ ID NO 540
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
aaaaaaaaca uaaaaaaaa					19

<210> SEQ ID NO 541
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
aaaaaaaugg gaaaaaaaa					19

<210> SEQ ID NO 542
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
aaaaaaaauu gaaaaaaaa					19

<210> SEQ ID NO 543
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
aaaaaaacuc uaaaaaaaa					19

<210> SEQ ID NO 544
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
aaaaaaaaua caaaaaaaa					19

<210> SEQ ID NO 545
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
aaaaaaaaga uaaaaaaaa					19

<210> SEQ ID NO 546
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
aaaaaaagca gaaaaaaaa					19

<210> SEQ ID NO 547
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
aaaaaaaagc uaaaaaaaa					19

<210> SEQ ID NO 548
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
aaaaaaacug gaaaaaaaa                                                      19

<210> SEQ ID NO 549
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
aaaaaaaacu uaaaaaaaa                                                      19

<210> SEQ ID NO 550
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
aaaaaaauac gaaaaaaaa                                                      19

<210> SEQ ID NO 551
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
aaaaaaaccc uaaaaaaaa                                                      19

<210> SEQ ID NO 552
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
aaaaaaaaug gaaaaaaaa                                                      19

<210> SEQ ID NO 553
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
aaaaaaauca gaaaaaaaa                                                      19

<210> SEQ ID NO 554
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
aaaaaaaccu uaaaaaaaa                                          19

<210> SEQ ID NO 555
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
aaaaaaaguc caaaaaaaa                                          19

<210> SEQ ID NO 556
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
aaaaaaacgu caaaaaaaa                                          19

<210> SEQ ID NO 557
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
aaaaaaaucg gaaaaaaaa                                          19

<210> SEQ ID NO 558
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
aaaaaaagac uaaaaaaaa                                          19

<210> SEQ ID NO 559
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
aaaaaaaaug aaaaaaaaa                                          19

<210> SEQ ID NO 560
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560 aaaaaaaacau uaaaaaaaa                                           19

<210> SEQ ID NO 561
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
aaaaaaaauc uaaaaaaaa                                            19

<210> SEQ ID NO 562
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
aaaaaaaagu caaaaaaaa                                            19

<210> SEQ ID NO 563
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
aaaaaaacgu gaaaaaaaa                                            19

<210> SEQ ID NO 564
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
aaaaaaagau caaaaaaaa                                            19

<210> SEQ ID NO 565
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
aaaaaaaagu aaaaaaaaa                                            19

<210> SEQ ID NO 566
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
aaaaaaaccg uaaaaaaaa                                            19

<210> SEQ ID NO 567
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
aaaaaaauaa caaaaaaaa                                                19

<210> SEQ ID NO 568
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
aaaaaaaucc uaaaaaaaa                                                19

<210> SEQ ID NO 569
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
aaaaaaacuu gaaaaaaaa                                                19

<210> SEQ ID NO 570
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
aaaaaaaagu gaaaaaaaa                                                19

<210> SEQ ID NO 571
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
aaaaaaaucg caaaaaaaa                                                19

<210> SEQ ID NO 572
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
aaaaaaacuu uaaaaaaaa                                                19

<210> SEQ ID NO 573
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
aaaaaaacgc uaaaaaaa                                                    19

<210> SEQ ID NO 574
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
aaaaaaaauu aaaaaaaa                                                    19

<210> SEQ ID NO 575
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
aaaaaaauuc aaaaaaaa                                                    19

<210> SEQ ID NO 576
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
aaaaaaauuc gaaaaaaa                                                    19

<210> SEQ ID NO 577
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
aaaaaaaauu uaaaaaaa                                                    19

<210> SEQ ID NO 578
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
aaaaaaaaua gaaaaaaa                                                    19

```
<210> SEQ ID NO 579
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
aaaaaaaaua uaaaaaaa                                                       19

<210> SEQ ID NO 580
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
aaaaaaacua gaaaaaaa                                                       19

<210> SEQ ID NO 581
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
aaaaaaacug caaaaaaa                                                       19

<210> SEQ ID NO 582
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
aaaaaaagaa uaaaaaaa                                                       19

<210> SEQ ID NO 583
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583 aaaaaaacg uaaaaaaa                                                        19

<210> SEQ ID NO 584
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
aaaaaaacga uaaaaaaa                                                       19

<210> SEQ ID NO 585
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
aaaaaaaguc gaaaaaaaa                                                      19

<210> SEQ ID NO 586
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
aaaaaaaguc uaaaaaaaa                                                      19

<210> SEQ ID NO 587
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
aaaaaaagca uaaaaaaaa                                                      19

<210> SEQ ID NO 588
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
aaaaaaagau gaaaaaaaa                                                      19

<210> SEQ ID NO 589
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
aaaaaaauca uaaaaaaaa                                                      19

<210> SEQ ID NO 590
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
aaaaaaagcg uaaaaaaaa                                                      19

<210> SEQ ID NO 591
<211> LENGTH: 19
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
aaaaaaaggc uaaaaaaa                                                       19

<210> SEQ ID NO 592
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
aaaaaaauua caaaaaaa                                                       19

<210> SEQ ID NO 593
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
aaaaaaaggu caaaaaaa                                                       19

<210> SEQ ID NO 594
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
aaaaaaagcc uaaaaaaa                                                       19

<210> SEQ ID NO 595
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
aaaaaaauuc uaaaaaaa                                                       19

<210> SEQ ID NO 596
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
aaaaaaaaug caaaaaaa                                                       19

<210> SEQ ID NO 597
<211> LENGTH: 19
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 597
aaaaaaagag uaaaaaaa                                                    19

<210> SEQ ID NO 598
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
aaaaaaaagu uaaaaaaa                                                    19

<210> SEQ ID NO 599
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
aaaaaaacag uaaaaaaa                                                    19

<210> SEQ ID NO 600
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
aaaaaaauga gaaaaaaa                                                    19

<210> SEQ ID NO 601
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
aaaaaaagau uaaaaaaa                                                    19

<210> SEQ ID NO 602
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
aaaaaaagcu uaaaaaaa                                                    19

<210> SEQ ID NO 603
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 603
aaaaaaauuu caaaaaaaa                                               19

<210> SEQ ID NO 604
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
aaaaaaauau gaaaaaaaa                                               19

<210> SEQ ID NO 605
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
aaaaaaauaa gaaaaaaaa                                               19

<210> SEQ ID NO 606
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
aaaaaaauac caaaaaaaa                                               19

<210> SEQ ID NO 607
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
aaaaaaauua gaaaaaaaa                                               19

<210> SEQ ID NO 608
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
aaaaaaaugc gaaaaaaaa                                               19

<210> SEQ ID NO 609
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 609
aaaaaaacgg uaaaaaaaa                                                    19

<210> SEQ ID NO 610
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
aaaaaaacua uaaaaaaaa                                                    19

<210> SEQ ID NO 611
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
aaaaaaauac uaaaaaaaa                                                    19

<210> SEQ ID NO 612
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
aaaaaaauau caaaaaaaa                                                    19

<210> SEQ ID NO 613
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
aaaaaaauag caaaaaaaa                                                    19

<210> SEQ ID NO 614
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
aaaaaaaucu caaaaaaaa                                                    19

<210> SEQ ID NO 615
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 615
aaaaaaagua caaaaaaaa                                              19

<210> SEQ ID NO 616
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
aaaaaaauag gaaaaaaaa                                              19

<210> SEQ ID NO 617
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
aaaaaaaucu gaaaaaaaa                                              19

<210> SEQ ID NO 618
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
aaaaaaauau uaaaaaaaa                                              19

<210> SEQ ID NO 619
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
aaaaaaaggu gaaaaaaaa                                              19

<210> SEQ ID NO 620
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
aaaaaaagug gaaaaaaaa                                              19

<210> SEQ ID NO 621
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 621
aaaaaaauua uaaaaaaaa                                              19

<210> SEQ ID NO 622
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
aaaaaaaguu caaaaaaaa                                              19

<210> SEQ ID NO 623
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
aaaaaaacgu uaaaaaaaa                                              19

<210> SEQ ID NO 624
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
aaaaaaauuu uaaaaaaaa                                              19

<210> SEQ ID NO 625
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
aaaaaaagga uaaaaaaaa                                              19

<210> SEQ ID NO 626
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
aaaaaaauuu gaaaaaaaa                                              19

<210> SEQ ID NO 627
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 627
aaaaaaauug gaaaaaaaa                                                    19

<210> SEQ ID NO 628
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
aaaaaaagua gaaaaaaaa                                                    19

<210> SEQ ID NO 629
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
aaaaaaaucu aaaaaaaa                                                     19

<210> SEQ ID NO 630
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
aaaaaaauaa uaaaaaaaa                                                    19

<210> SEQ ID NO 631
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
aaaaaaaugu uaaaaaaaa                                                    19

<210> SEQ ID NO 632
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
aaaaaaauga caaaaaaaa                                                    19

<210> SEQ ID NO 633
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
```
aaaaaaaugu caaaaaaaa     19

<210> SEQ ID NO 634
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
aaaaaaacug uaaaaaaaa     19

<210> SEQ ID NO 635
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
aaaaaaaaug uaaaaaaaa     19

<210> SEQ ID NO 636
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
aaaaaaagug caaaaaaaa     19

<210> SEQ ID NO 637
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
aaaaaaagua uaaaaaaaa     19

<210> SEQ ID NO 638
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
aaaaaaaugc caaaaaaaa     19

<210> SEQ ID NO 639
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
aaaaaaagug uaaaaaaaa                                             19

<210> SEQ ID NO 640
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
aaaaaaaugu gaaaaaaaa                                             19

<210> SEQ ID NO 641
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
aaaaaaaguu aaaaaaaaa                                             19

<210> SEQ ID NO 642
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
aaaaaaaggu uaaaaaaaa                                             19

<210> SEQ ID NO 643
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
aaaaaaauag uaaaaaaaa                                             19

<210> SEQ ID NO 644
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
aaaaaaauug uaaaaaaaa                                             19

<210> SEQ ID NO 645
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
aaaaaaauug caaaaaaaa                                             19

<210> SEQ ID NO 646
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
aaaaaaaugc uaaaaaaaa                                                19

<210> SEQ ID NO 647
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
aaaaaaauga uaaaaaaaa                                                19

<210> SEQ ID NO 648
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648 aaaaaaagg uaaaaaaaa                                                 19

<210> SEQ ID NO 649
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
aaaaaaaugg caaaaaaaa                                                19

<210> SEQ ID NO 650
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
aaaaaaaugg uaaaaaaaa                                                19

<210> SEQ ID NO 651
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
aaaaaaaguu gaaaaaaaa                                                19

```
<210> SEQ ID NO 652
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
aaaaaaaucg uaaaaaaa                                                   19

<210> SEQ ID NO 653
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
aaaaaaaucg uaaaaaaa                                                   19

<210> SEQ ID NO 654
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
aaaaaaaguu gaaaaaaa                                                   19

<210> SEQ ID NO 655
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
aaaaaaaugg uaaaaaaa                                                   19

<210> SEQ ID NO 656
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
aaaaaaaugg caaaaaaa                                                   19

<210> SEQ ID NO 657
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
aaaaaaaagg uaaaaaaa                                                   19
```

```
<210> SEQ ID NO 658
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
aaaaaaauga uaaaaaaa                                                        19

<210> SEQ ID NO 659
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
aaaaaaaugc uaaaaaaa                                                        19

<210> SEQ ID NO 660
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
aaaaaaauug caaaaaaa                                                        19

<210> SEQ ID NO 661
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
aaaaaaauug uaaaaaaa                                                        19

<210> SEQ ID NO 662
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
aaaaaaauag uaaaaaaa                                                        19

<210> SEQ ID NO 663
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
aaaaaaaggu uaaaaaaa                                                        19

<210> SEQ ID NO 664
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
aaaaaaaguu uaaaaaaa                                                  19

<210> SEQ ID NO 665
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
aaaaaaaugu gaaaaaaaa                                                 19

<210> SEQ ID NO 666
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
aaaaaaagug uaaaaaaaa                                                 19

<210> SEQ ID NO 667
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
aaaaaaaugc caaaaaaaa                                                 19

<210> SEQ ID NO 668
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
aaaaaaagua uaaaaaaaa                                                 19

<210> SEQ ID NO 669
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
aaaaaaagug caaaaaaaa                                                 19

<210> SEQ ID NO 670
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
aaaaaaaaug uaaaaaaaa                                                   19

<210> SEQ ID NO 671
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
aaaaaaacug uaaaaaaaa                                                   19

<210> SEQ ID NO 672
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
aaaaaaaugu caaaaaaaa                                                   19

<210> SEQ ID NO 673
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
aaaaaaauga caaaaaaaa                                                   19

<210> SEQ ID NO 674
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
aaaaaaaugu uaaaaaaaa                                                   19

<210> SEQ ID NO 675
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
aaaaaaauaa uaaaaaaaa                                                   19

<210> SEQ ID NO 676
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 676
aaaaaaaucu aaaaaaaa                                                    19

<210> SEQ ID NO 677
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
aaaaaaagua gaaaaaaaa                                                   19

<210> SEQ ID NO 678
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
aaaaaaauug gaaaaaaaa                                                   19

<210> SEQ ID NO 679
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
aaaaaaauuu gaaaaaaaa                                                   19

<210> SEQ ID NO 680
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
aaaaaaagga uaaaaaaaa                                                   19

<210> SEQ ID NO 681
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
aaaaaaauuu uaaaaaaaa                                                   19

<210> SEQ ID NO 682
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 682
aaaaaaacgu uaaaaaaa                                                          19

<210> SEQ ID NO 683
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
aaaaaaaucg uaaaaaaaa                                                         19

<210> SEQ ID NO 684
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
aaaaaaaguu gaaaaaaa                                                          19

<210> SEQ ID NO 685
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
aaaaaaaugg uaaaaaaa                                                          19

<210> SEQ ID NO 686
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
aaaaaaaugg caaaaaaa                                                          19

<210> SEQ ID NO 687
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
aaaaaaaagg uaaaaaaa                                                          19

<210> SEQ ID NO 688
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 688
aaaaaaauga uaaaaaaa                                                   19

<210> SEQ ID NO 689
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689
aaaaaaaugc uaaaaaaa                                                   19

<210> SEQ ID NO 690
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
aaaaaaauug caaaaaaa                                                   19

<210> SEQ ID NO 691
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
aaaaaaauug uaaaaaaa                                                   19

<210> SEQ ID NO 692
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
aaaaaaauag uaaaaaaa                                                   19

<210> SEQ ID NO 693
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
aaaaaaaggu uaaaaaaa                                                   19
```

```
<210> SEQ ID NO 694
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
aaaaaaaguu uaaaaaaa                                                    19

<210> SEQ ID NO 695
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 695
aaaaaaaugu gaaaaaaa                                                    19

<210> SEQ ID NO 696
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
aaaaaaagug uaaaaaaa                                                    19

<210> SEQ ID NO 697
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
aaaaaaaugc caaaaaaa                                                    19

<210> SEQ ID NO 698
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
aaaaaaagua uaaaaaaa                                                    19

<210> SEQ ID NO 699
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
aaaaaaagug caaaaaaa                                                    19

<210> SEQ ID NO 700
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
aaaaaaaaug uaaaaaaaa                                                   19

<210> SEQ ID NO 701
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
aaaaaaacug uaaaaaaaa                                                   19

<210> SEQ ID NO 702
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
aaaaaaaugu caaaaaaaa                                                   19

<210> SEQ ID NO 703
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
aaaaaaauga caaaaaaaa                                                   19

<210> SEQ ID NO 704
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
aaaaaaaugu uaaaaaaaa                                                   19

<210> SEQ ID NO 705
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
aaaaaaauaa uaaaaaaaa                                                   19

<210> SEQ ID NO 706
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
aaaaaaaucu aaaaaaaa                                                   19

<210> SEQ ID NO 707
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
aaaaaaagua gaaaaaaa                                                   19

<210> SEQ ID NO 708
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
aaaaaaauug gaaaaaaa                                                   19

<210> SEQ ID NO 709
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
aaaaaaauuu gaaaaaaa                                                   19

<210> SEQ ID NO 710
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
aaaaaaagga uaaaaaaa                                                   19

<210> SEQ ID NO 711
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
aaaaaaauuu uaaaaaaa                                                   19

<210> SEQ ID NO 712
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 712
aaaaaaacgu uaaaaaaa                                                      19
```

COMPOSITIONS AND METHODS FOR IMMUNOSTIMULATORY RNA OLIGONUCLEOTIDES

SEQUENCE LISTING

The instant application contains a Sequence Listing which has been submitted via EFS-Web and is hereby incorporated by reference in its entirety. Said ASCII copy, created on Jul. 16, 2010, is named 51058059.txt and is 169,189 bytes in size.

FIELD OF THE INVENTION

The present invention relates to the field of immunotherapy and drug discovery. The present invention provides a method for determining the immunostimulatory activity of a RNA oligonucleotide. The present invention also provides a method for predicting the immunostimulatory activity of a single-stranded RNA oligonucleotide (ssRNA). The present invention further provides a method for preparing ssRNA oligonucleotides with high or low immunostimulatory activity. Moreover, the present invention provides ssRNA oligonucleotides with immunostimulatory activity and the therapeutic uses thereof. In addition, the present invention provides antisense RNA with gene silencing activity and with either high or low immunostimulatory activity, the methods of their preparation, and their therapeutic uses.

BACKGROUND OF THE INVENTION

The development of synthetic compounds that mimic the presence of viruses may result in potent novel candidate drugs for the treatment of viral infection and cancer. The immune system employs at least four members of the family of Toll-like receptors (TLR3, TLR7, TLR8 and TLR9) to detect viruses based on the presence of certain characteristics of viral nucleic acid [1]. By far the most information is available for TLR9 [2, 3]. TLR9 detects so-called CpG motifs within microbial DNA [4]. Synthetic oligonucleotides containing such CpG motifs (CpG ODN) have been extensively studied over the last 10 years, and the lead compound ODN 2006 (identical with ODN 7909, ProMune) is currently entering clinical phase III for the treatment of cancer. Although CpG ODN represent strong Th1 vaccine adjuvants and show excellent anti-tumor activity in murine models of cancer [5, 6], their application for the treatment of human disease is limited. In mice TLR9 is expressed on B cells and both myeloid and plasmacytoid dendritic cells, whereas in humans expression is restricted to B cells and PDC [7, 8]. As a consequence, in the absence of T cell help, in mice CpG ODN stimulate both IL-12 and IFN-α in mice, while in humans, CpG ODN stimulate only IFN-α.

Recent data suggest that this deficit of CpG ODN in humans can be overcome by RNA oligonucleotides. Unlike TLR9 detecting DNA, TLR3, TLR7 and TLR8 all recognize RNA. TLR3 binds to long double-stranded (ds) RNA [9] and therefore by definition can not be activated by short synthetic oligoribonucleotides (ORN). TLR7 detects short dsRNA (as used for siRNA) [10] and both long and short single-stranded (ss) RNA [10-12]. RNA recognition by TLR8 is limited to ssRNA. Both TLR7 and TLR8 are expressed in human myeloid cells and thus, ORNs that serve as ligands for TLR7 and TLR8 are excellent candidates for eliciting the desired IL-12 response which is missing when CpG ODN is used for stimulation in the human system.

While for TLR9 the optimal sequence motif (CpG motif) has been exactly defined [4, 13, 14], the situation is much less clear for TLR7 and TLR8. It has been suggested that the potency of RNA oligonucleotides depends on a high content of G and U. One group proposed that the presence of the UGUGU motif confers IFN-α-inducing activity to RNA oligonucleotides. Our group defined a 9mer sequence motif [10]. WO 03/086280 discloses that guanosine, particularly guanosine in combination with uracil, are natural ligands of TLR8. Additional TLR8 ligands disclosed in WO 03/086280 include nucleic acid molecules containing one or more copies of GUU, GUG, GGU, GGG, UGG, UGU, UUG, UUU, UUGUGG, UGGUUG, GUGUGU, and GGGUUU.

In none of the studies published to date efforts were undertaken to distinguish potentially distinct sequence requirements for TLR7 and TLR8. However, small molecules (nucleoside analogues) have been proposed that specifically activate TLR7 or TLR8 [15], supporting the idea that TLR7 and TLR8 may indeed have preferences for distinct RNA motifs.

It is an object of the present invention to identify RNA oligonucleotide motifs for stimulating an immune response, in particular, IL-12 induction. It is also an object of the present invention to identify ligands for activating TLR8. It is another object of the present invention to develop a method for determining the immunostimulatory activity, in particular, the IL-12-inducing activity, of a RNA oligonucleotide. It is yet another object of the present invention to develop a method for predicting the immunostimulatory activity, in particular, IL-12-inducing activity, of a RNA oligonucleotide. It is a further object of the invention to develop a method for designing and preparing RNA oligonucleotide having or lacking immunostimulatory activity, in particular, IL-12-inducing activity. It is also an object of the invention to provide RNA oligonucleotides having high immunostimulatory activity which can be used to induce an immune response, in particular, IL-12 production, in patients in need thereof. It is yet another object of the present invention to provide antisense RNA molecules that either have or lack immunostimulatory activity which can be used to treat disorders caused by the expression or overexpression of disease/disorder-related genes.

SUMMARY OF THE INVENTION

The present invention provides a method for determining the immunostimulatory activity of a RNA oligonucleotide, a method for predicting the immunostimulatory activity of a RNA oligonucleotide, a method for preparing a RNA oligonucleotide with high or low immunostimulatory activity, and a method for preparing an antisense RNA oligonucleotide with gene silencing activity and with high or low immunostimulatory activity.

The present application also provides an in vitro method for inducing IL-12 production from a mammalian cell.

The present invention further provides a single-stranded RNA oligonucleotide with immunostimulatory activity, an antisense RNA oligonucleotide with gene silencing activity and with high or low immunostimulatory activity, and the therapeutic uses thereof.

In addition, the present invention provides a pharmaceutical composition comprising one or more of the RNA oligonucleotides of the invention.

BRIEF DESCRIPTION OF THE FIGURES

FIG. 9A discloses SEQ ID NOS 460-509, respectively, in order of appearance. FIG. 9B discloses SEQ ID NOS 510-559, respectively, in order of appearance. FIG. 9C discloses SEQ ID NOS 560-609, respectively, in order of appearance. FIG. 9D discloses SEQ ID NOS 610-652, respectively, in order of appearance.

FIG. 10 discloses "IL-12 index rank" oligonucleotides as SEQ ID NOS 653-682, respectively, in order of appearance. FIG. 10 also discloses SEQ ID NOS 683-712, respectively, in order of appearance.

Figure 11:
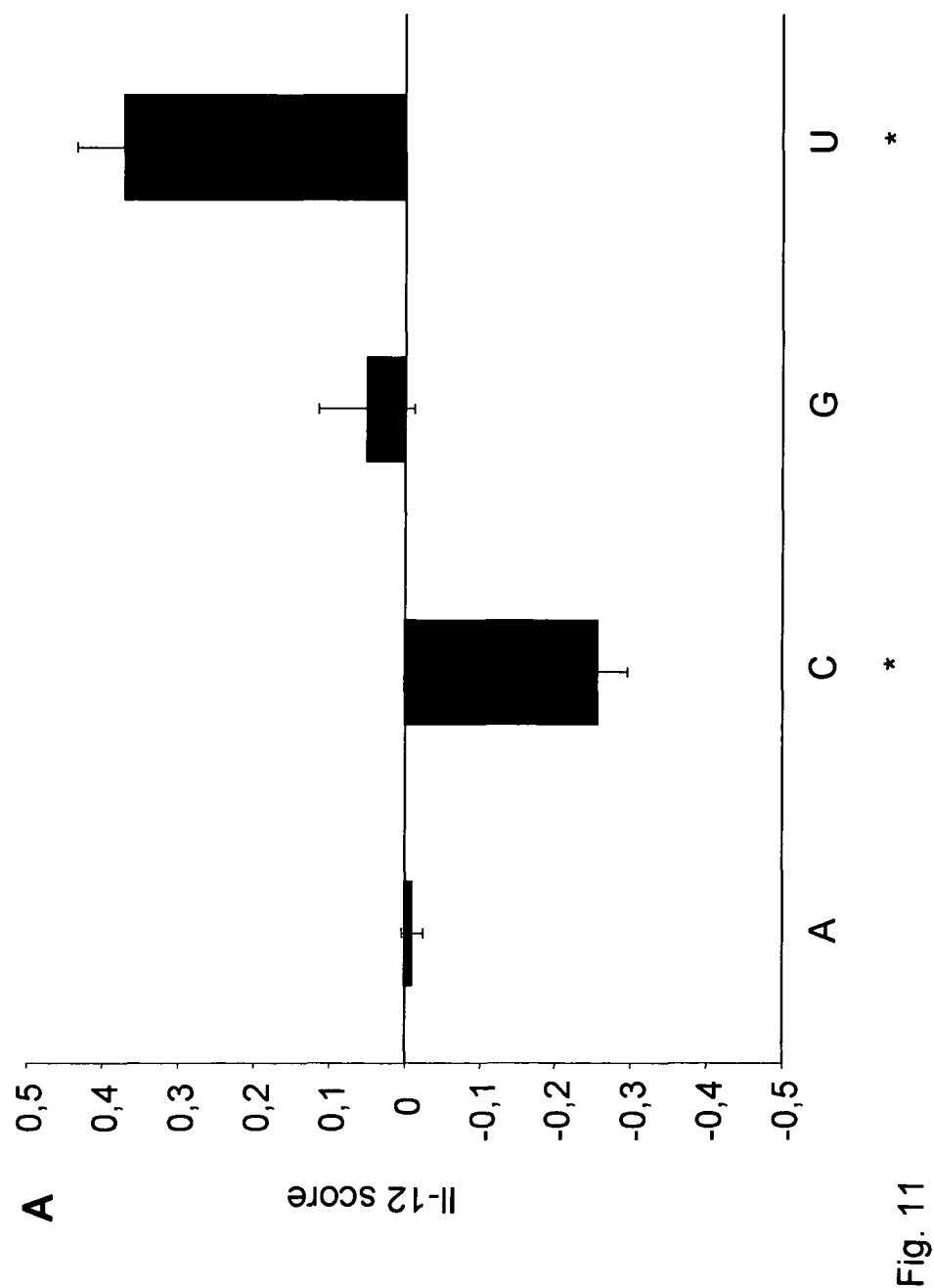
FIG. 11: For all possible 1 mer motifs (5'-X-3'), 2mer motifs (5'-XX-3',5'-X*X-3',5'-X**X-3') or 3mer motifs (5'-
Figure 11:
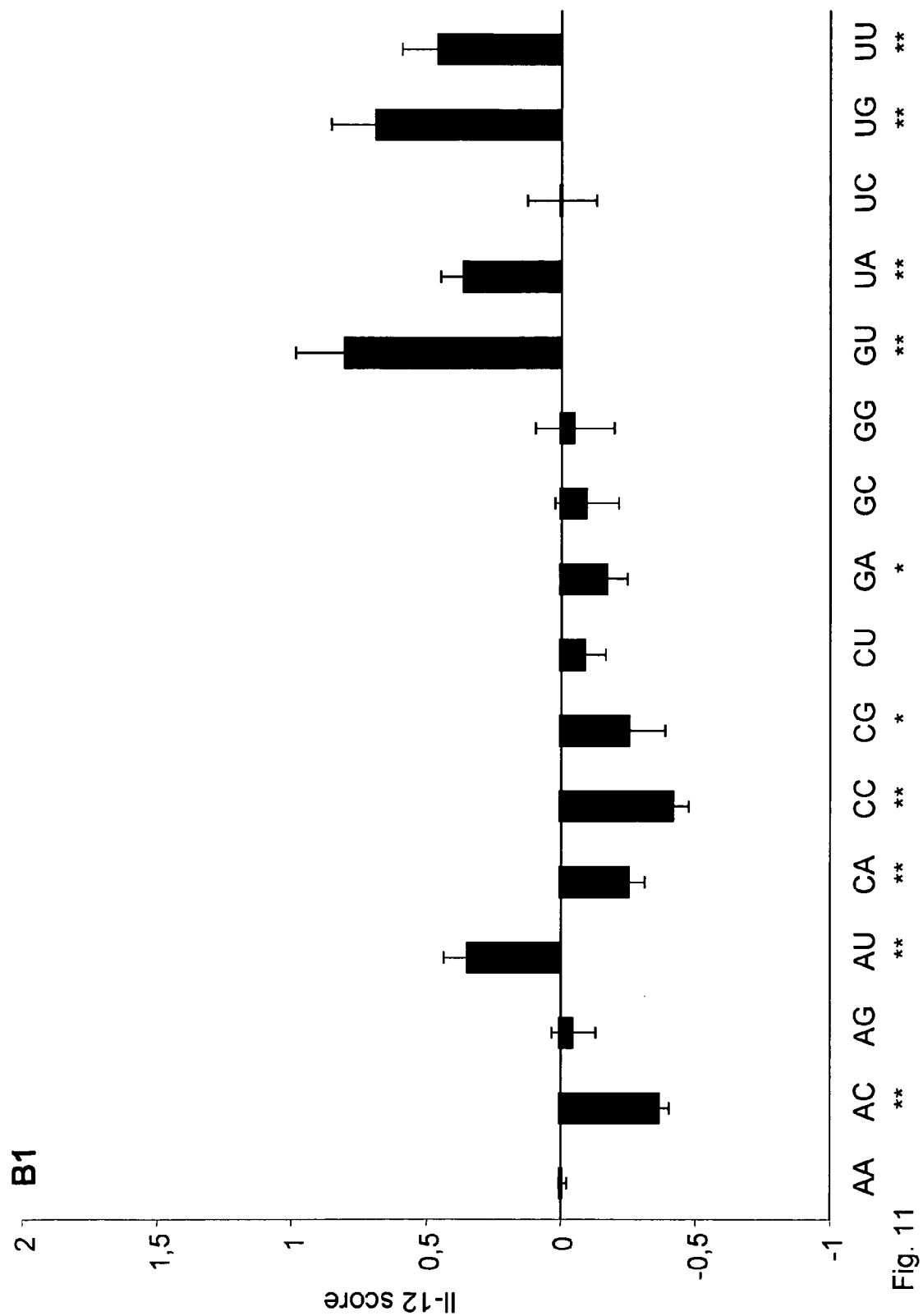
Figure 11:
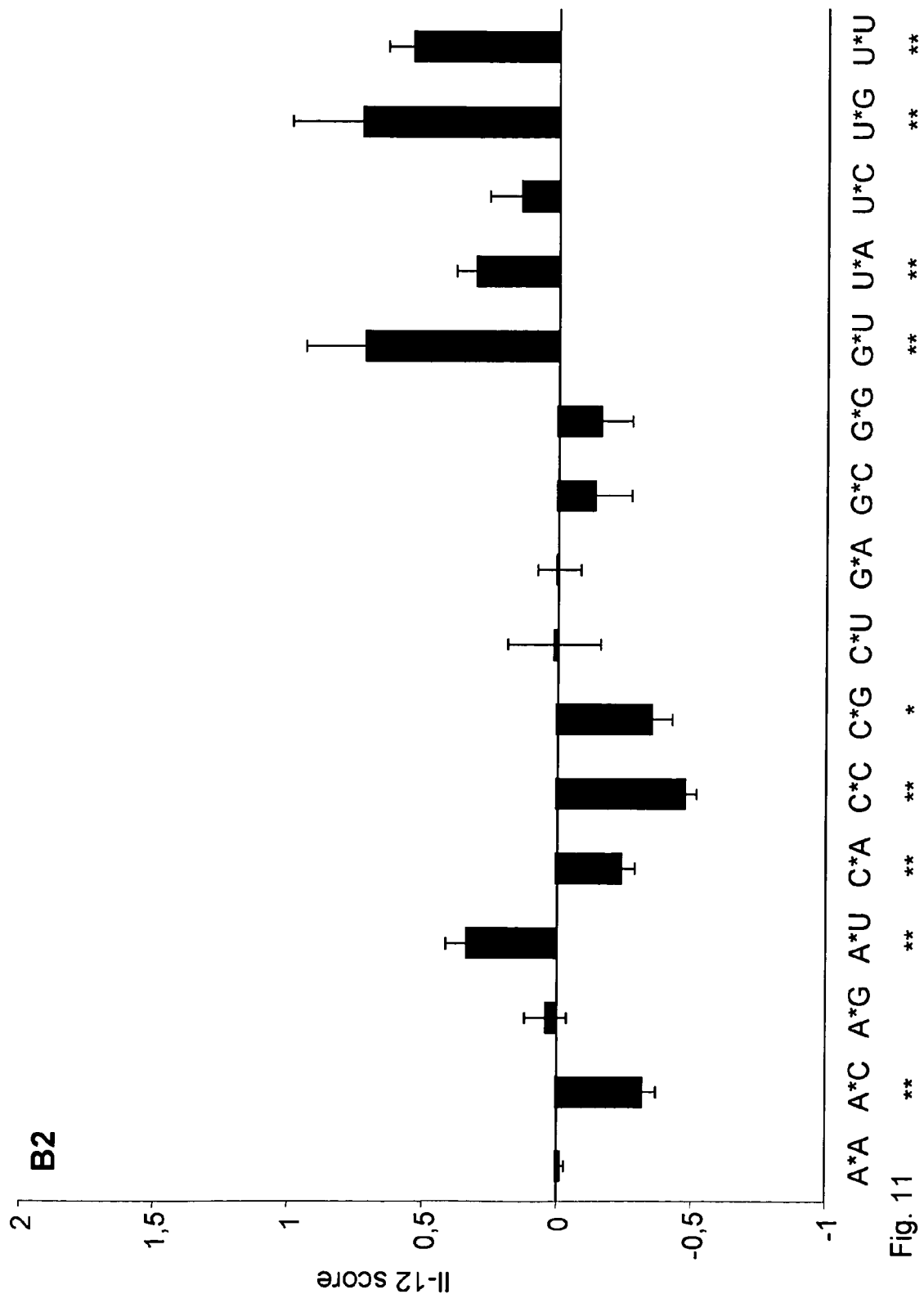
Figure 11:
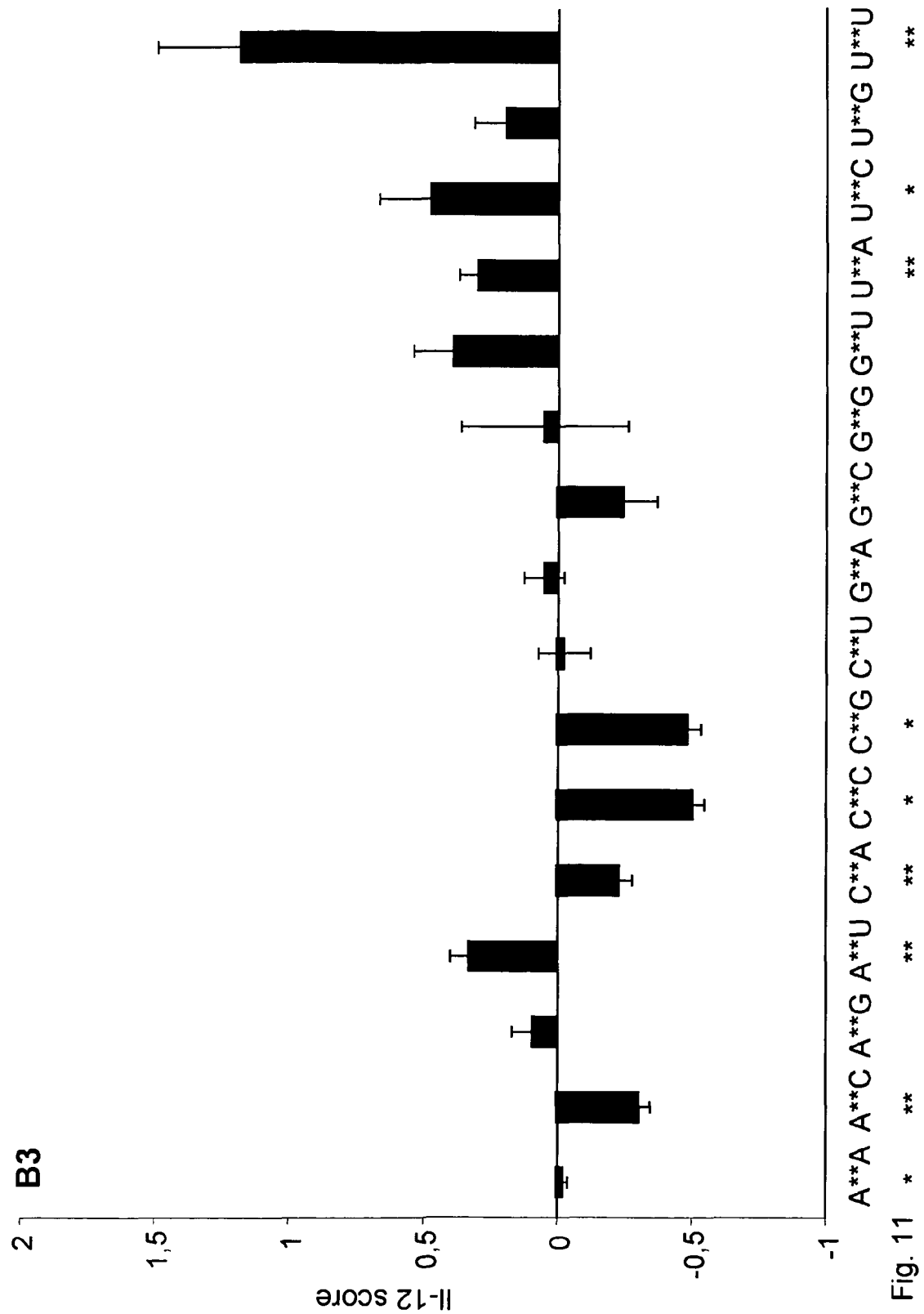
Figure 11:
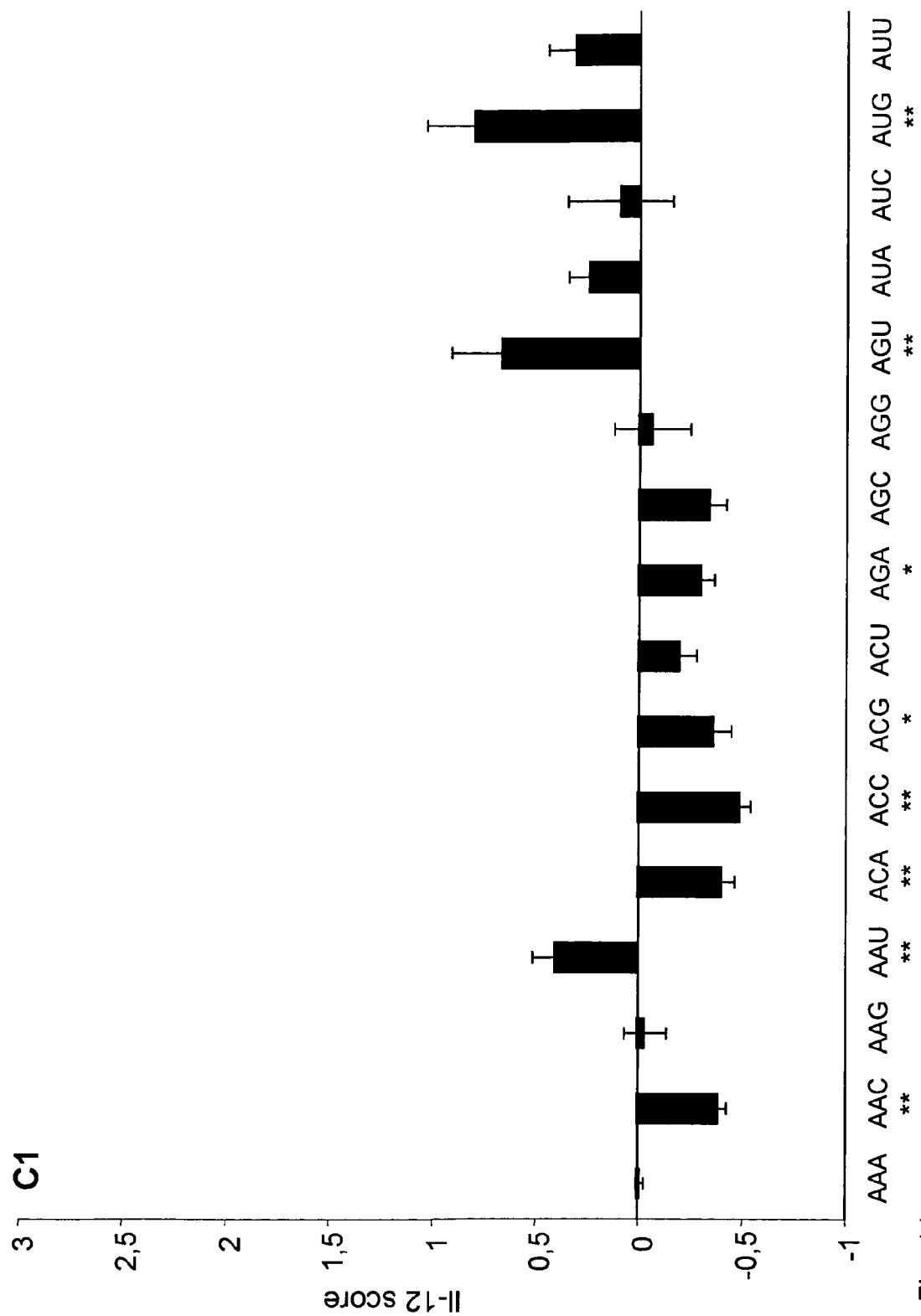
Figure 11:
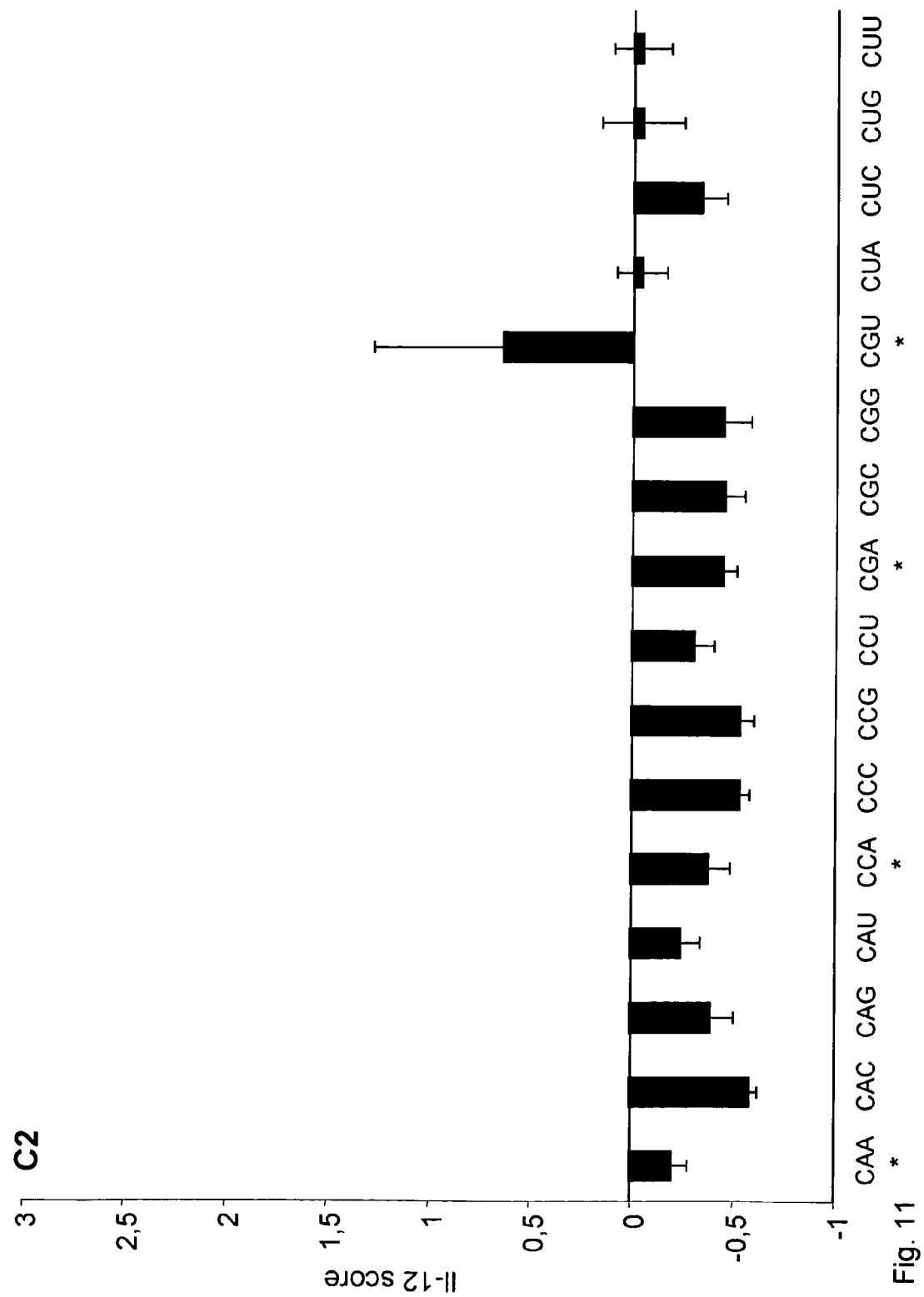
Figure 11:
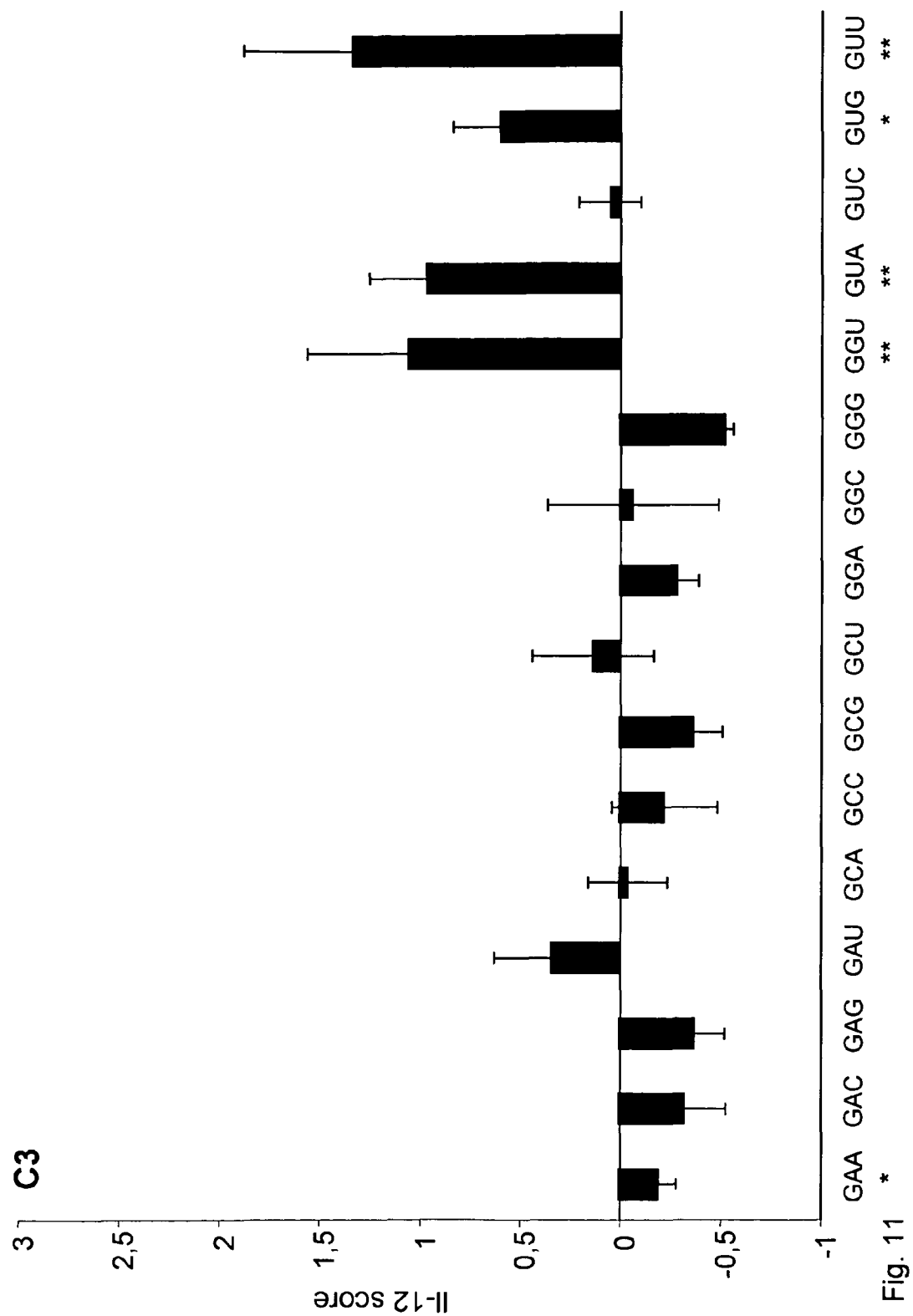
Figure 11:
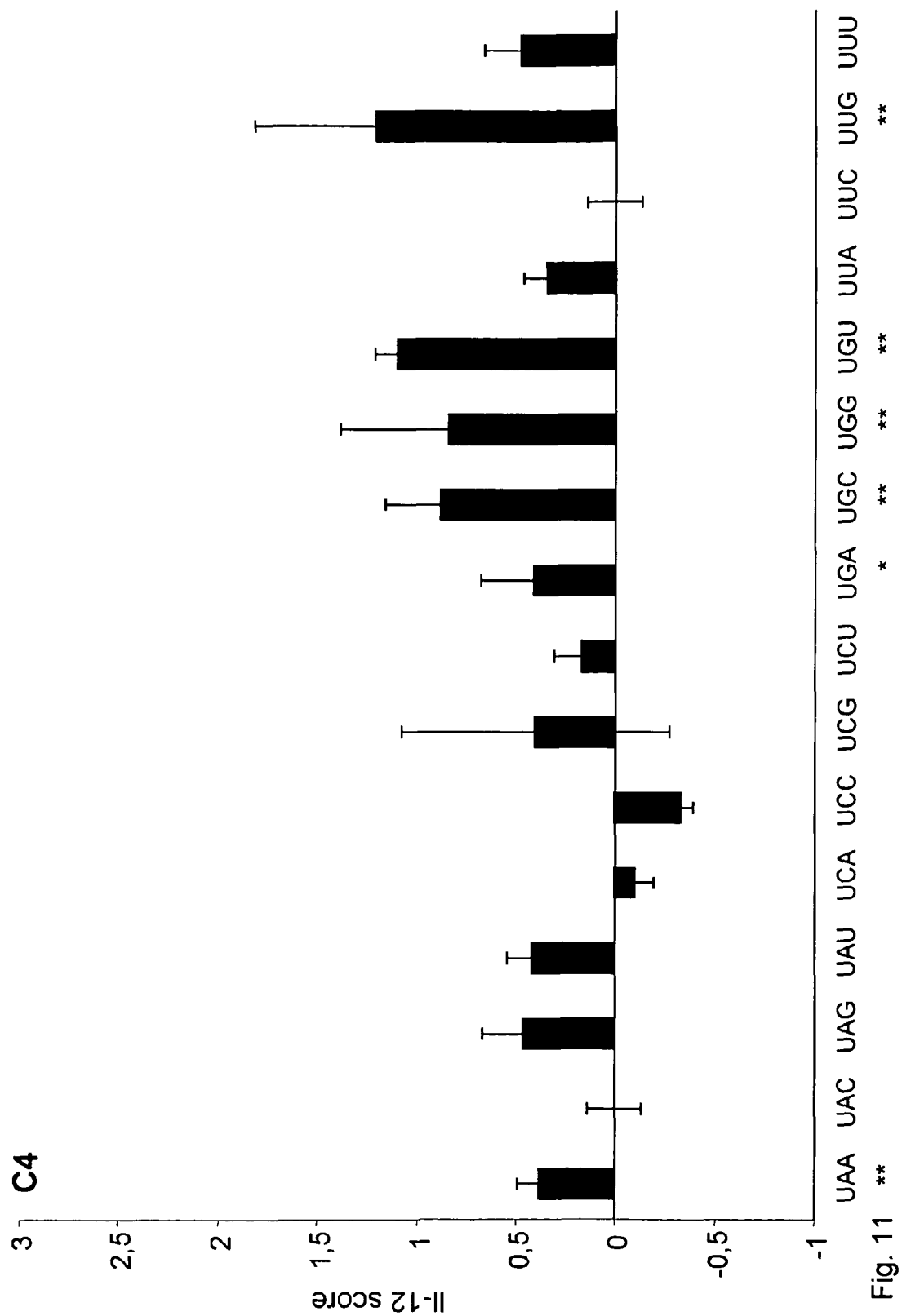
Figure 11:
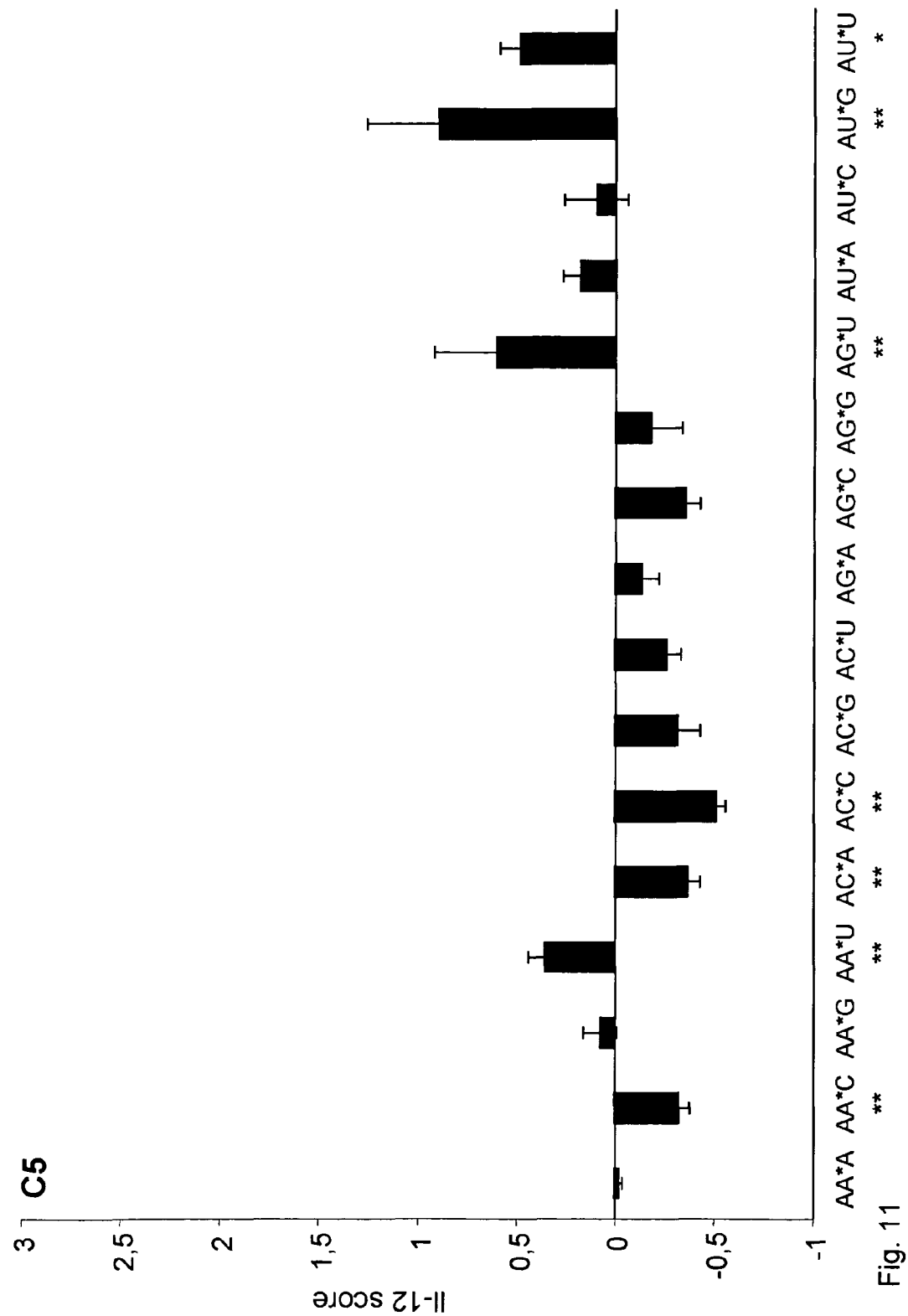
Figure 11:
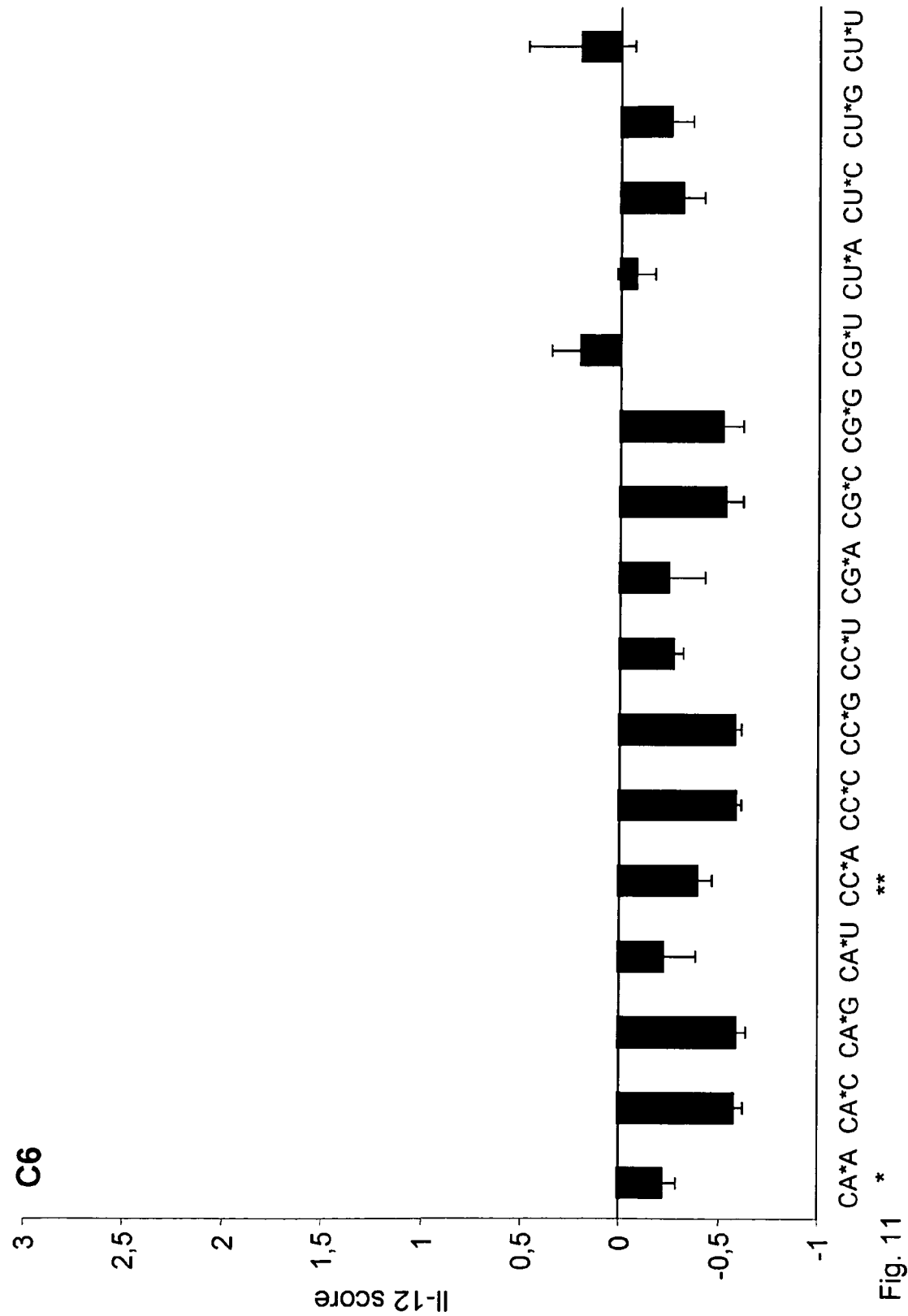
Figure 11:
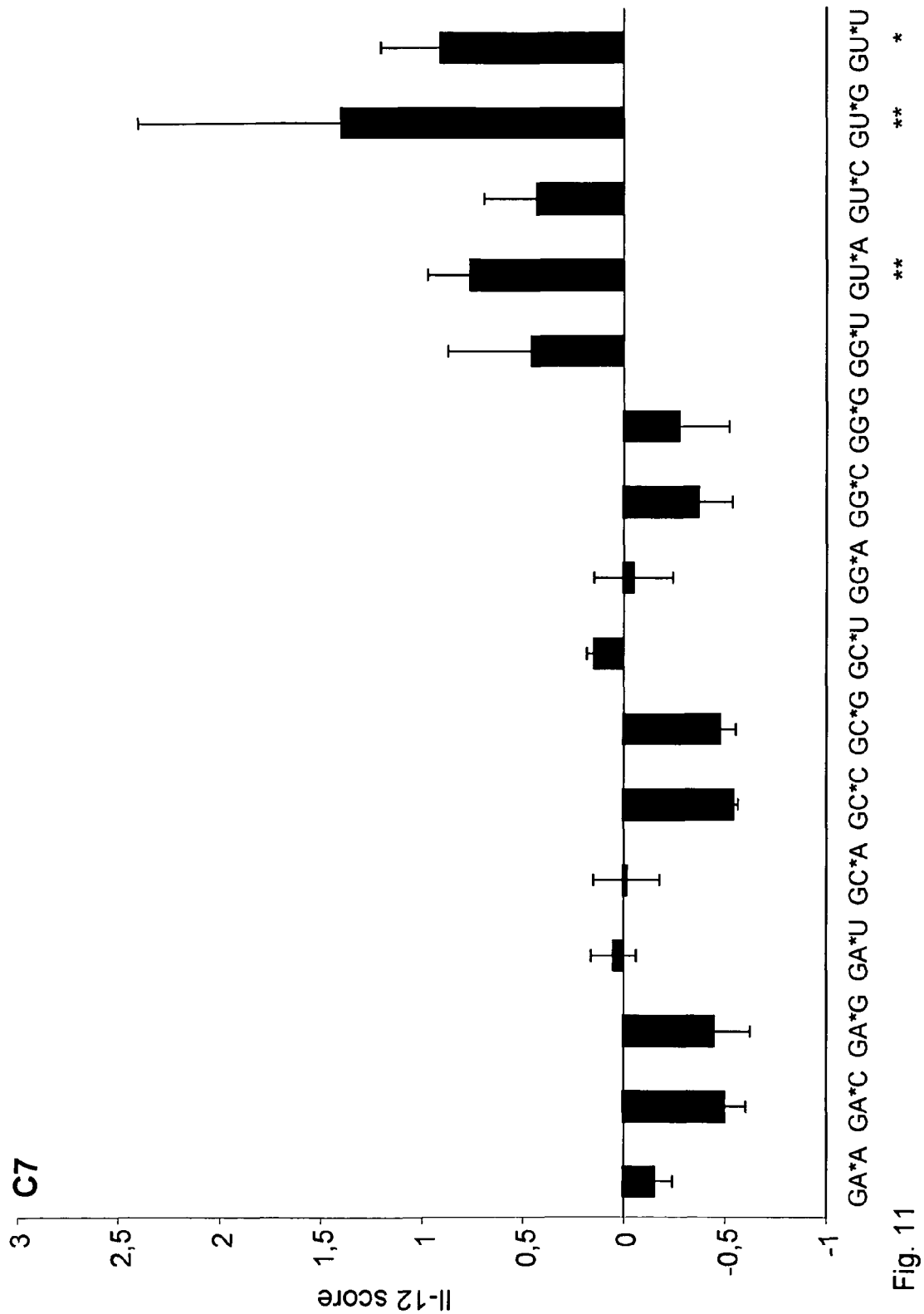
Figure 11:
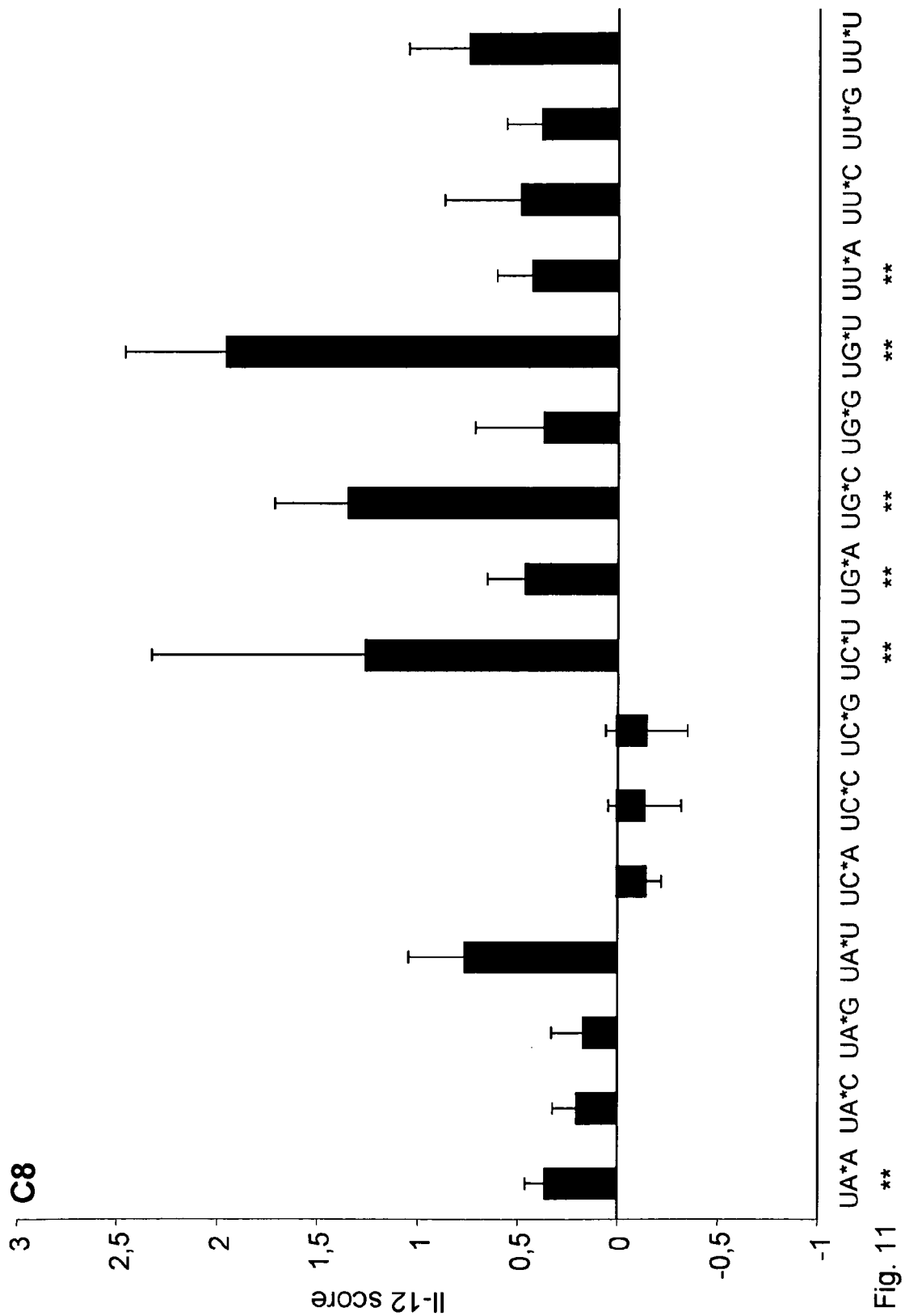
Figure 11:
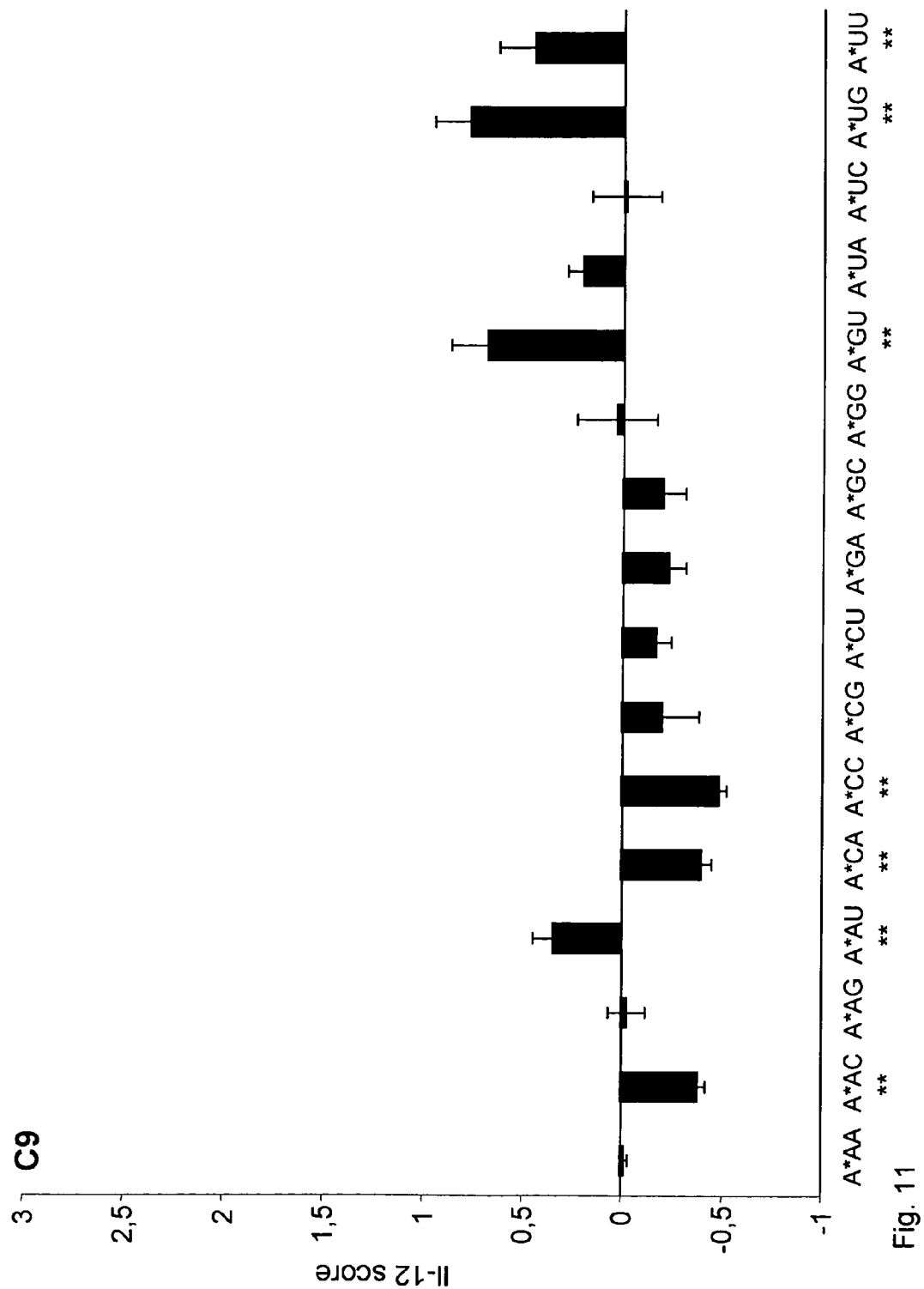
Figure 11:
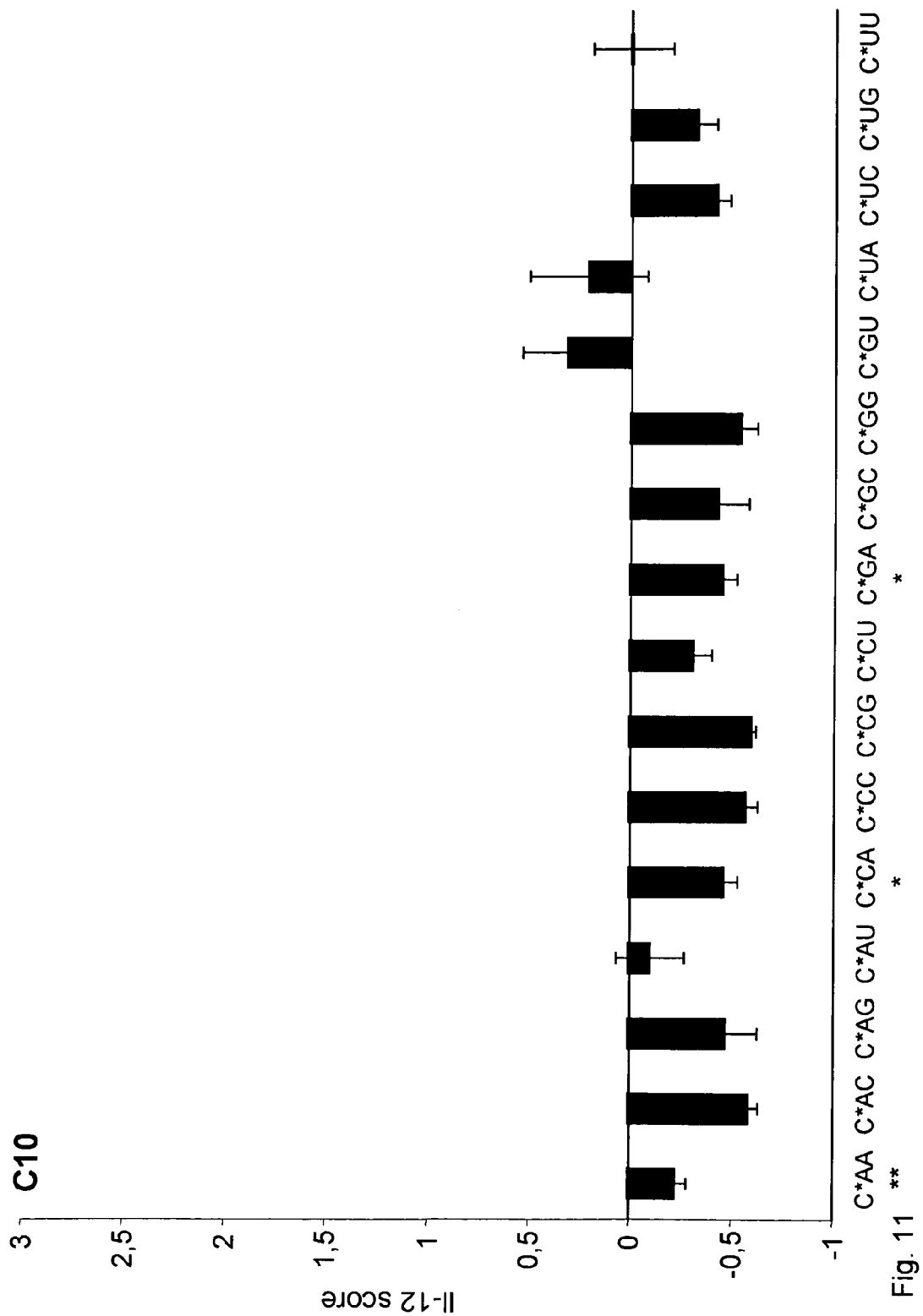
Figure 11:
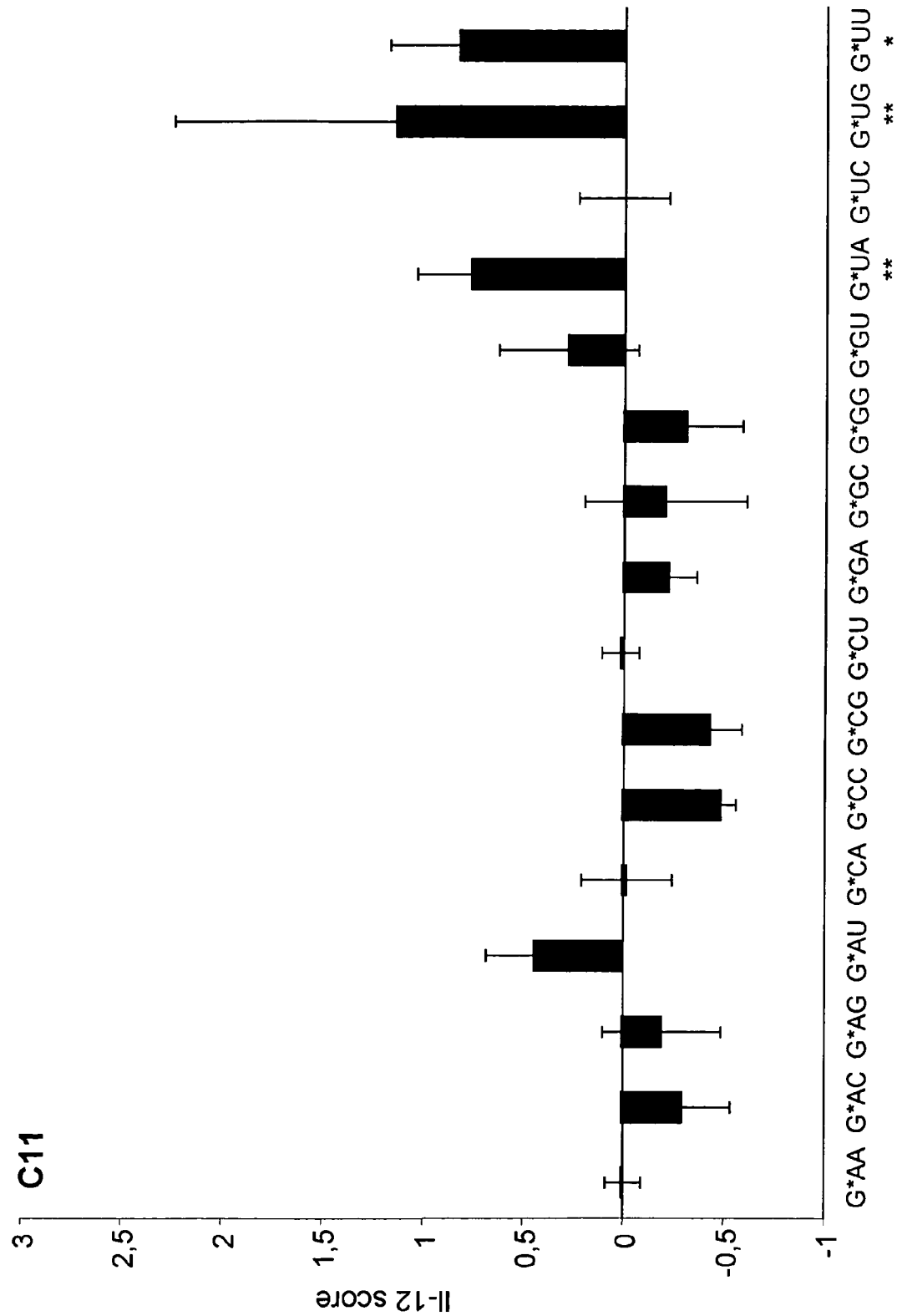
Figure 11:
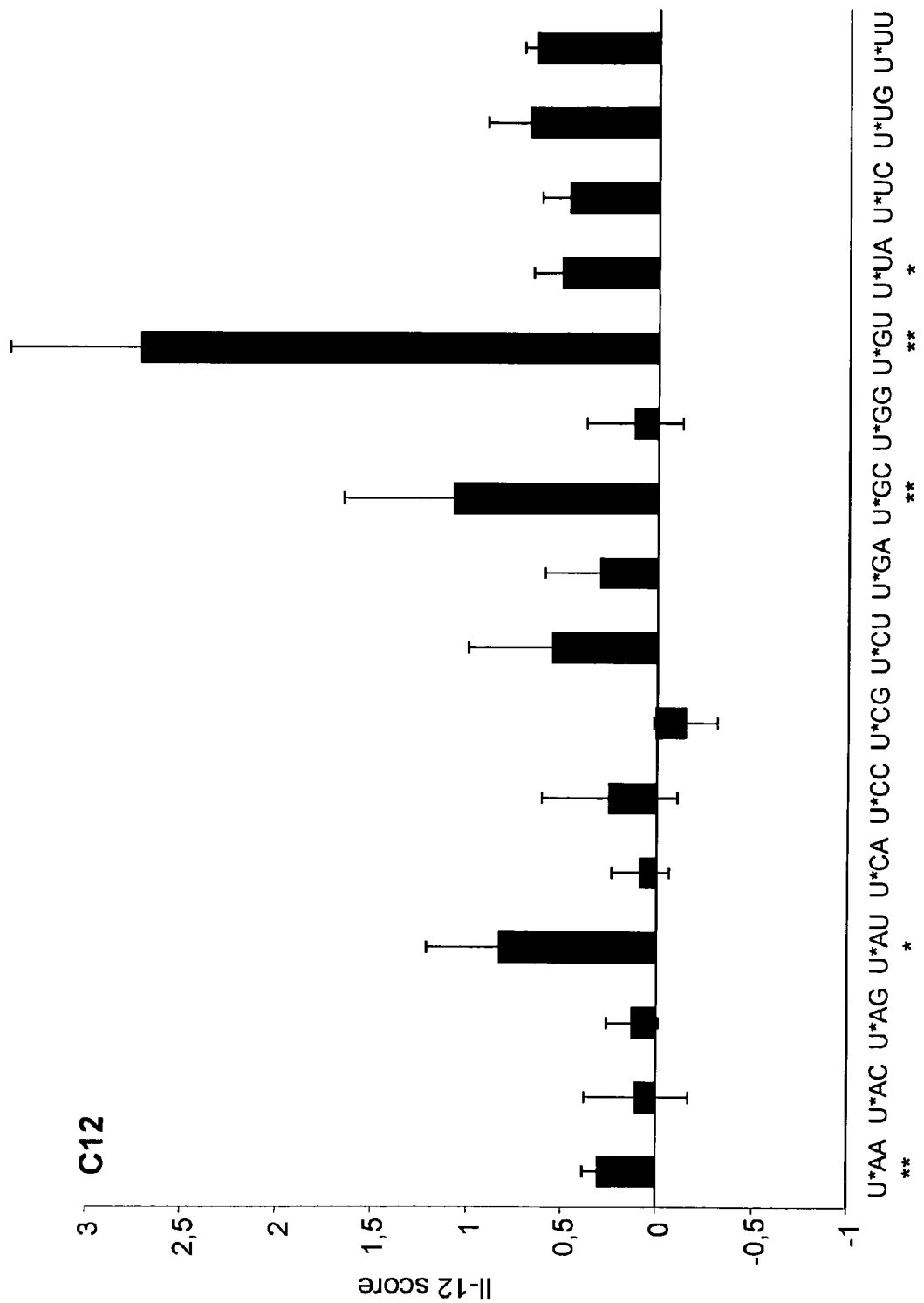
Figure 12:
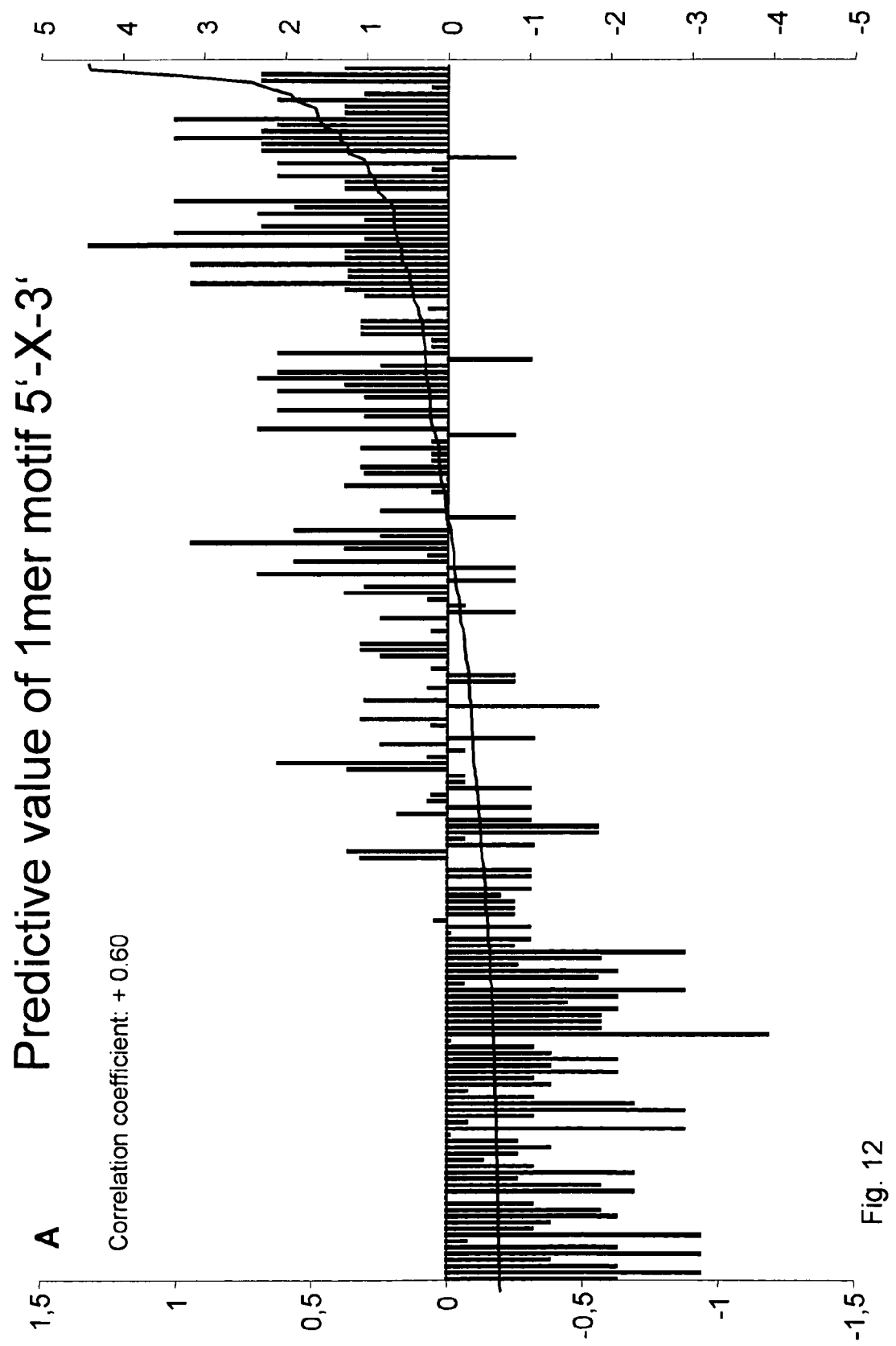
Figure 12:
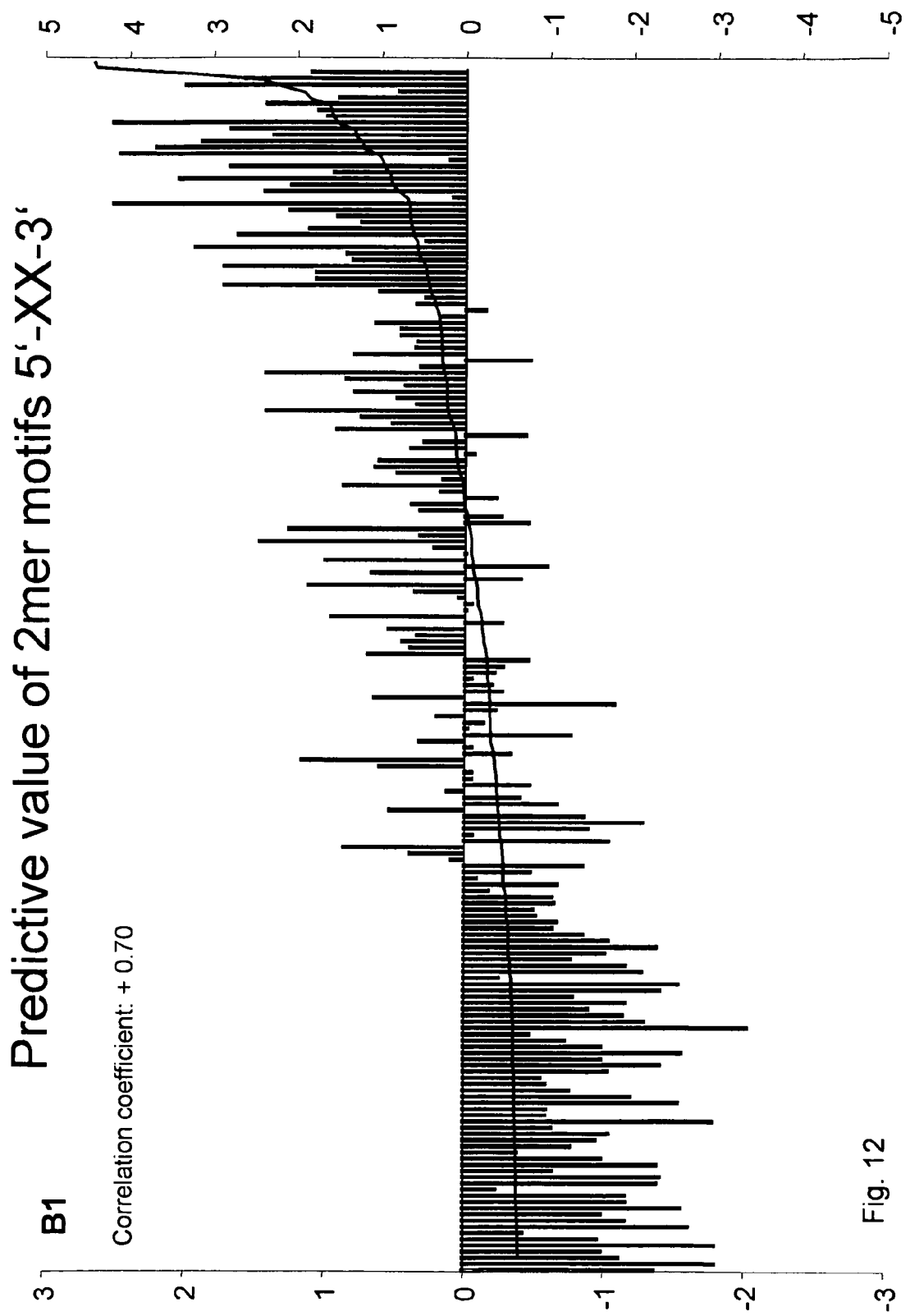
Figure 12:
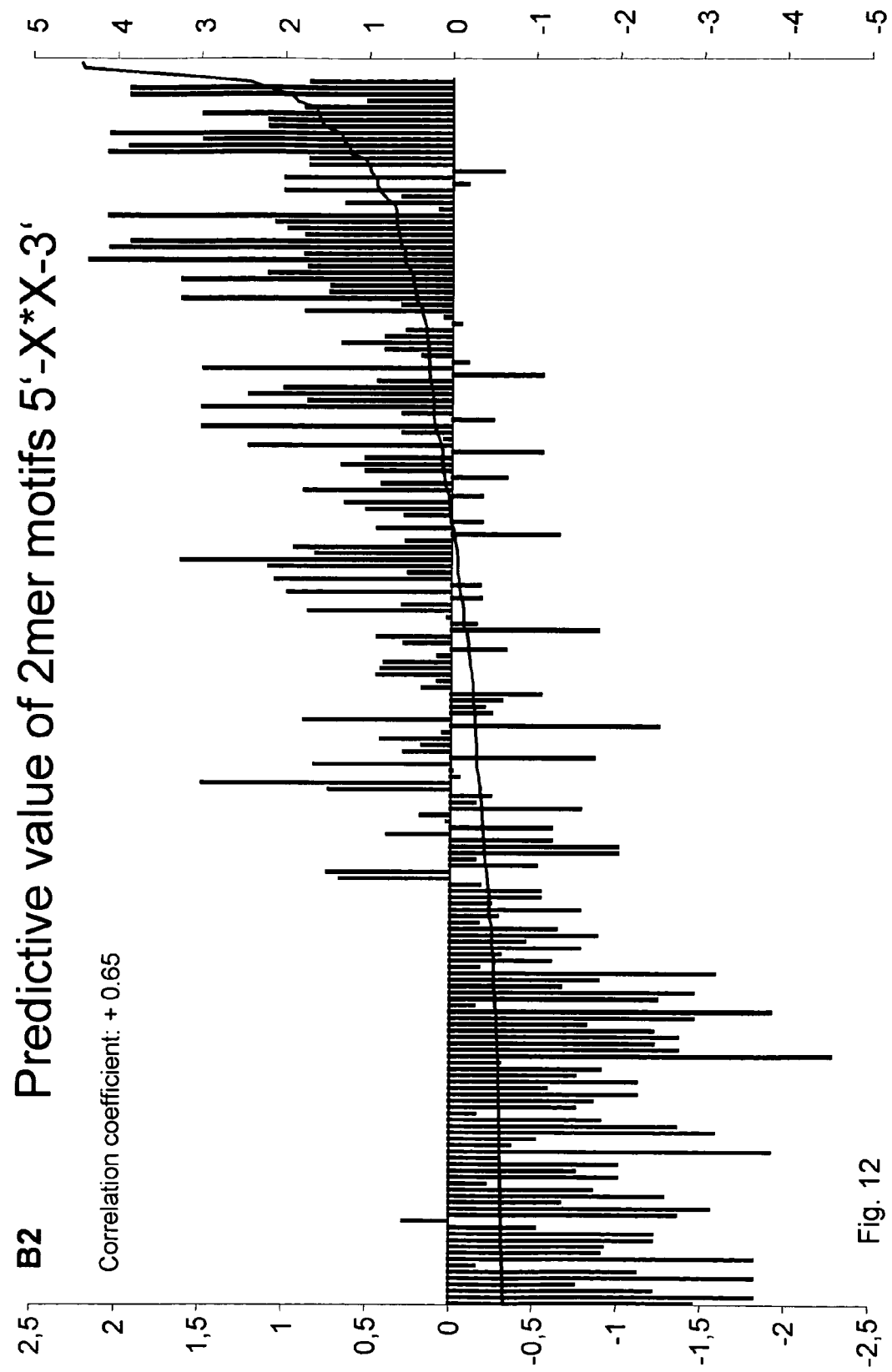
Figure 12:
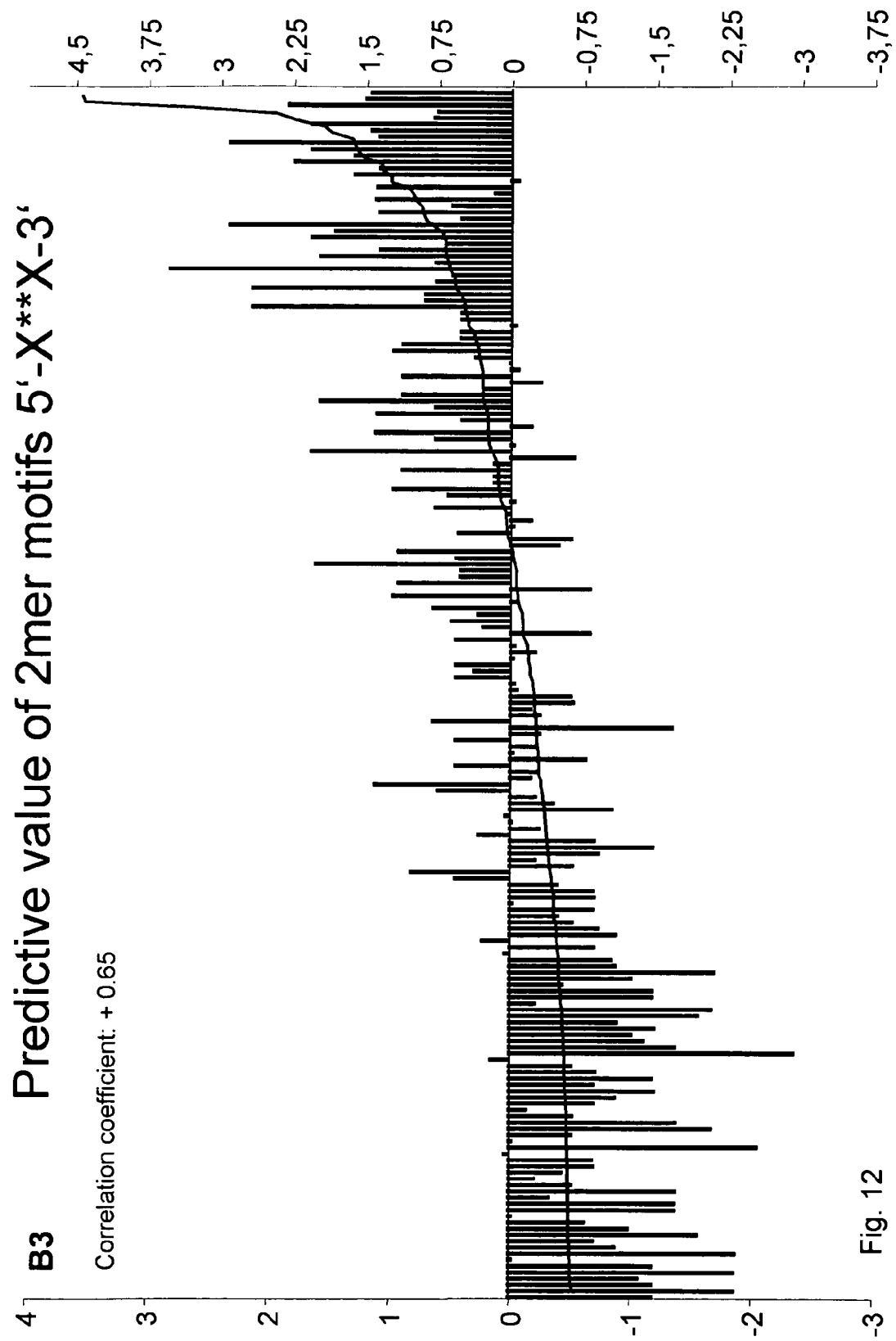
Figure 12:
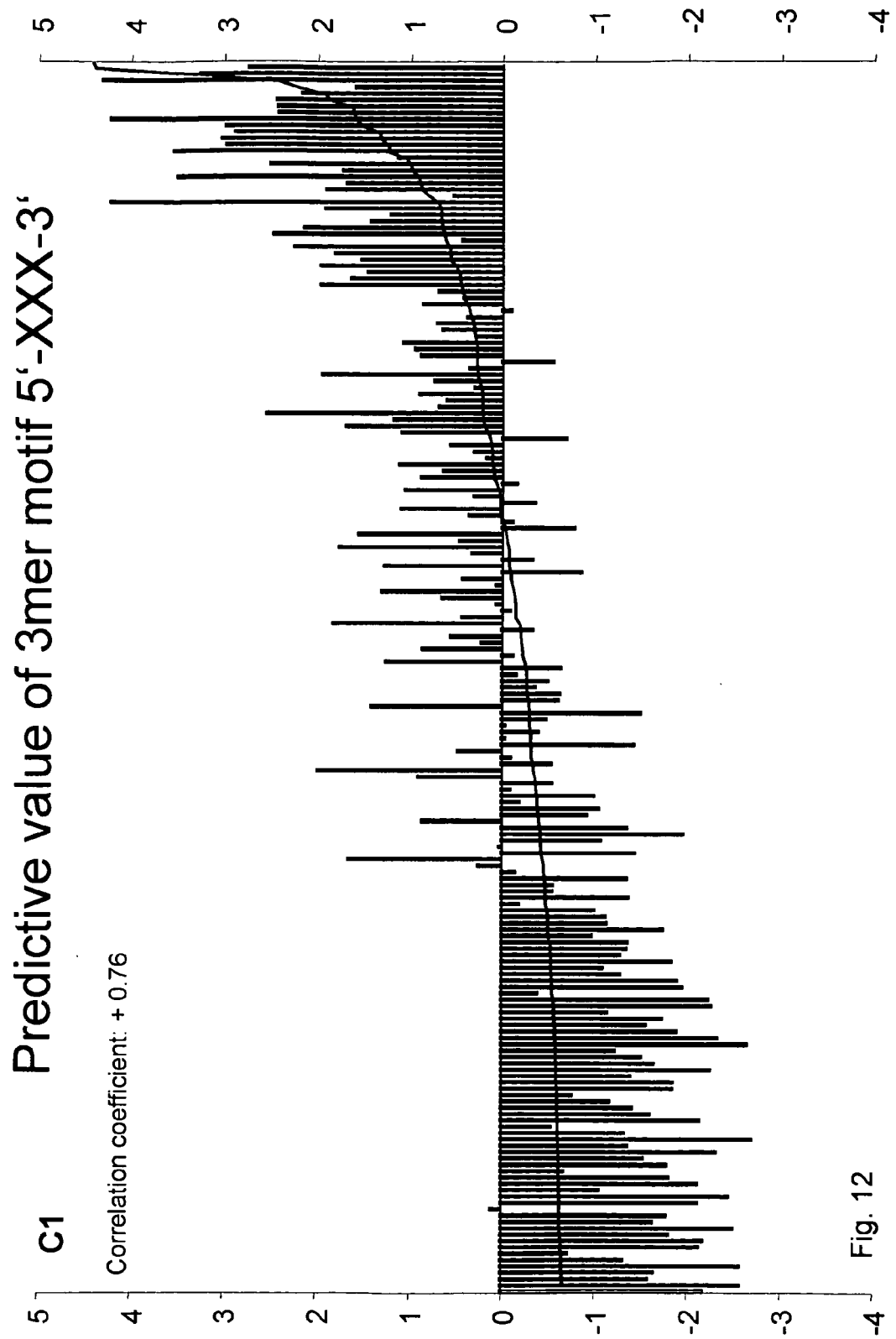
Figure 12:
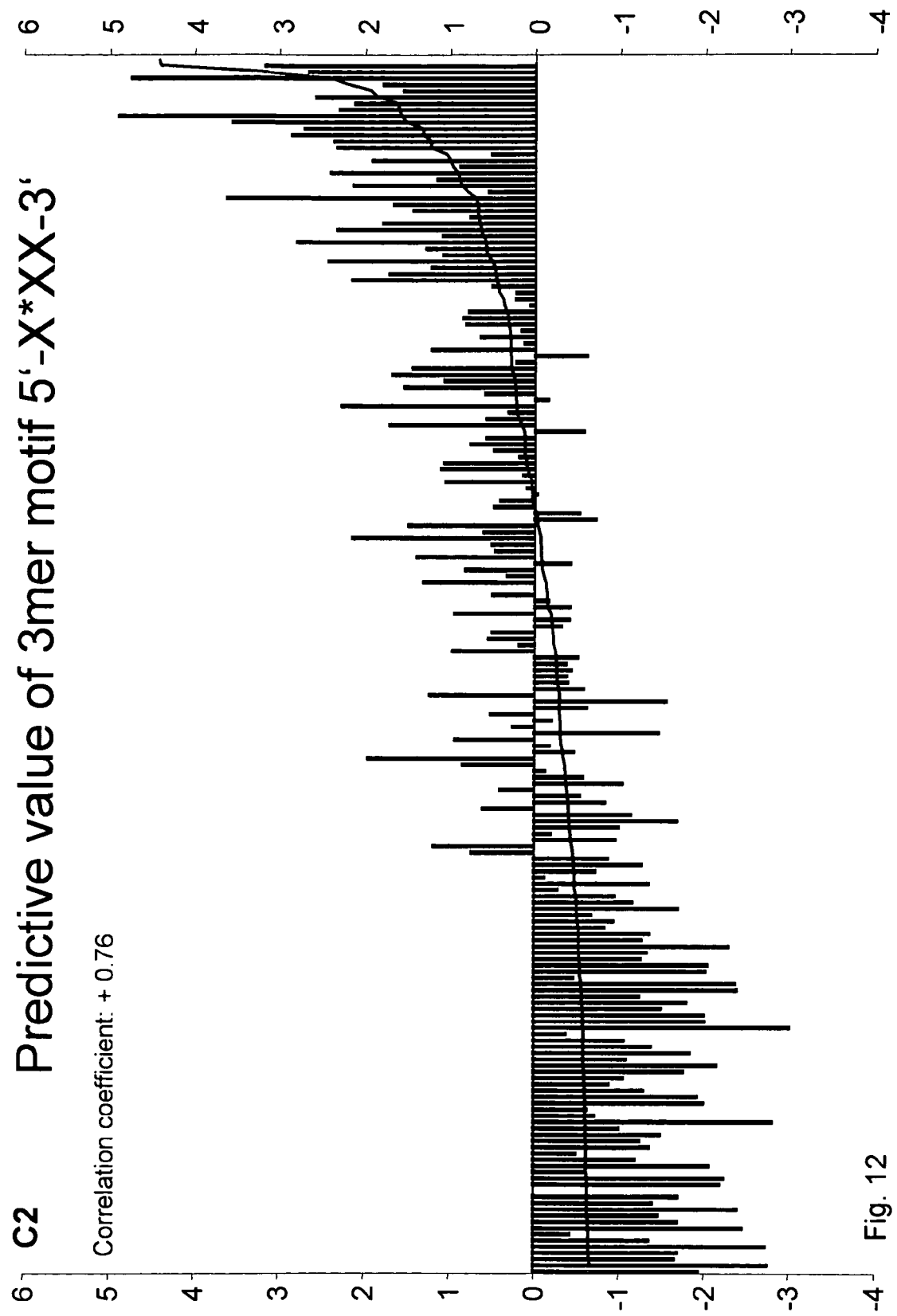
Figure 12:
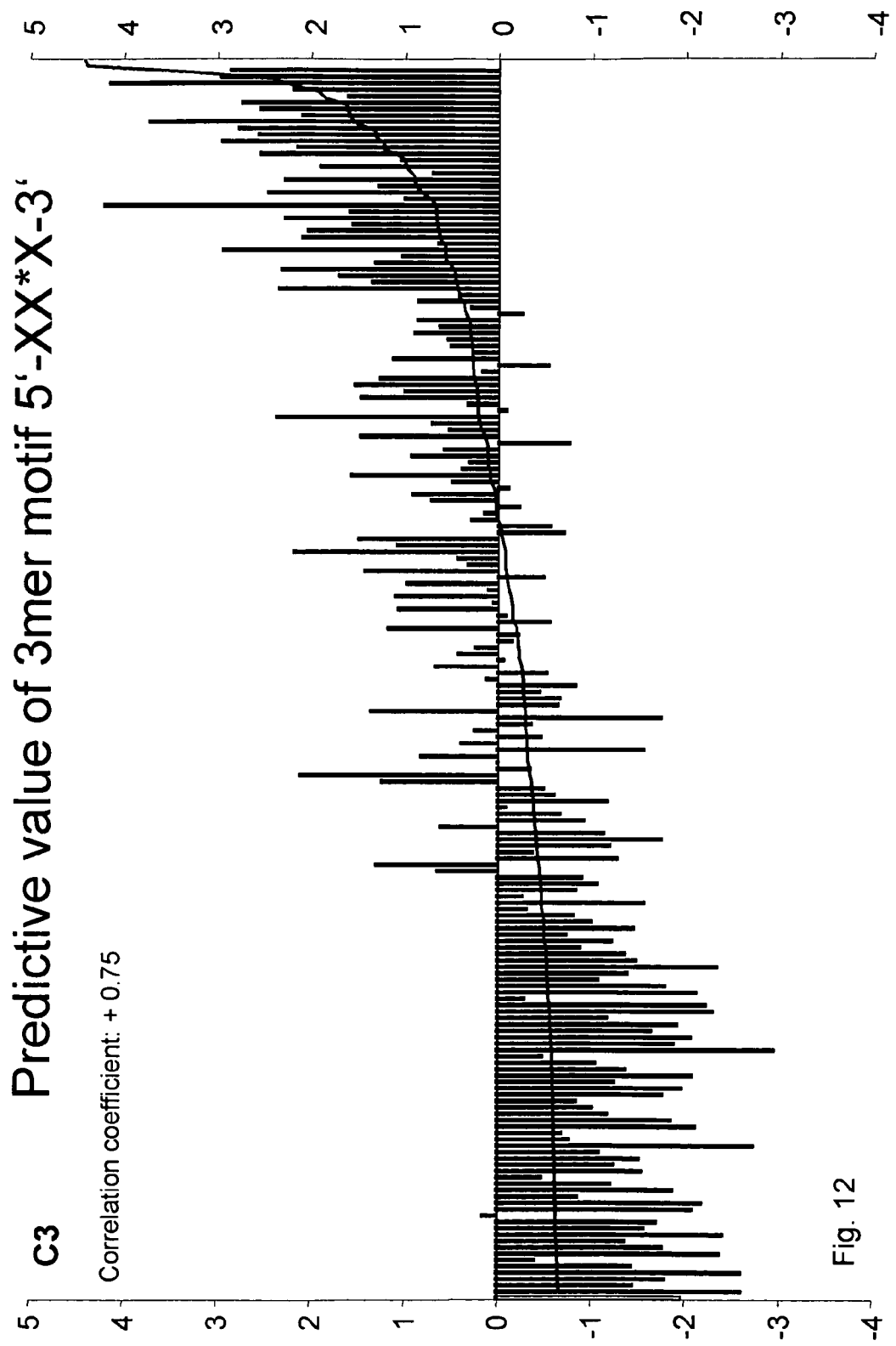
Figure 12:
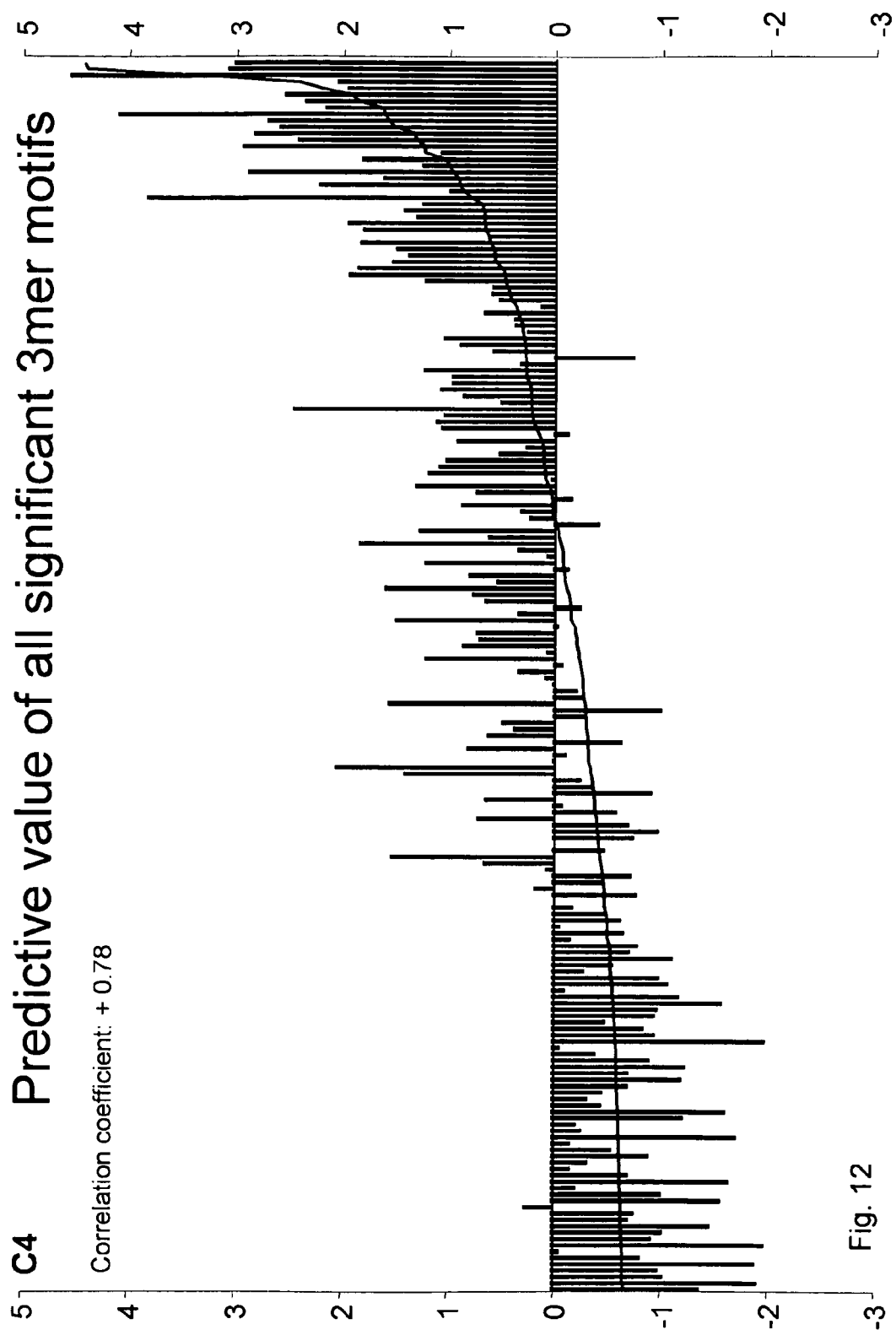

XXX-3',5'-XX*X-3',5'-X*XX-3') a mean IL-12 index was assigned by calculating a mean IL-12 index of all ssRNA oligonucleotides containing the corresponding motifs (=IL-12 score of a given motif). The IL-12 score of all possible motifs is depicted in FIG. 11 ±SEM: 1mer motifs 5'-X-3' (FIG. 11A); 2mer motifs 5'-XX-3' (FIG. 11B1), 5'-X*X-3' FIG. (11B2), 5'-X**X-3' (FIG. 11B3) and 3mer motifs 5'-XXX-3' (FIG. 11C1-11C4), 5'-XX*X-3' (FIG. 11C5-11C8), 5'-X*XX-3' (FIG. 11C9-11C12). A two-tailed Student's t-test for unpaired samples was used to analyze a putative significant difference between the respective motifs. A p-value >0.01 and <0.05 is marked by a "*", whereas a p-value <0.01 is marked by a "**".

FIG. 12: A calculated IL-12 index was assigned to each oligonucleotide by using the obtained motif-IL-12 scores. For each set of motifs [1mer motifs (5'-X-3'), 2mer motifs (5'-XX-3',5'-X*X-3',5'-X**X-3') or 3mer motifs (5'-XXX-3',5'-XX*X-3',5'-X*XX-3'] a predicted IL-12 index was calculated for each ssRNA oligonucleotide. Next, the obtained predicted IL-12 indices were compared to the actual adjusted IL-12 indices. Data are depicted the following way: For all ssRNA oligonucleotides the predicted IL-12 indices are shown as a black bars, whereas data are sorted in ascending order according to the actual IL-12 score that is depicted as a red index line. The y-axis on the left side depicts the scale for the predicted IL-12 score, while the y-axis on the right side depicts the scale for the actual IL-12 score.

DETAILED DESCRIPTION OF THE INVENTION

Definitions

As used herein, "a" and "an" refers to a group or species of entities, rather than one single individual.

Oligonucleotide

As used herein, the term "oligonucleotide" refers to a polynucleotide formed from a plurality of linked nucleoside units. Such oligonucleotides can be obtained from existing nucleic acid sources, including genomic or cDNA, but are preferably produced by synthetic methods including chemical synthesis, in vitro and in vivo transcription. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, pyrophosphate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (Rp)— or (Sp)-phosphorothioate, alkylphosphonate, or phosphotriester linkages).

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

As used herein, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

RNA oligonucleotides discussed herein include otherwise unmodified RNA as well as RNA which have been modified (e.g., to improve efficacy), and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. 1994, *Nucleic Acids Res* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

All nucleic acid sequences listed herein are in the 5' to 3' direction unless otherwise indicated.

The RNA oligonucleotide of the invention is single-stranded. Furthermore, the ssRNA oligonucleotide of the invention does not contain any palindromic or otherwise self-complementary sequences which allow for the formation of a hairpin (or stem-loop) secondary structure with double-stranded characteristics.

The length of a ssRNA oligonucleotide is the number of nucleotides it contains. A ssRNA oligonucleotide containing n nucleotides can also be called a "n-mer" oligonucleotide.

Enhanced Nuclease Resistance

For increased nuclease resistance and/or binding affinity to the target, an oligonucleotide can include, for example, 2'-modified ribose units and/or phosphorothioate linkage(s) and/or pyrophosphate linkage(s). For example, the 2/hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification. "Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2∝-methoxyethyl, 2'-OCH3,2'-O-allyl, 2'-C-allyl, and 2'-fluoro. To maximize nuclease resistance, the 2' modifications can be used in combination with one or more phosphate linker modifications (e.g., phosphorothioate). The so-called "chimeric" oligonucleotides are those that contain two or more different modifications. The inclusion of furanose sugars in the oligonucleotide backbone can also decrease endonucleolytic cleavage. An oligonucleotide agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

Single-stranded RNA oligonucleotides which contain self-complementary sequences and form a hairpin structure have enhanced nuclease resistance compared to single-stranded oligonucleotides which do not.

5-Phosphate Modifications

The oligonucleotides of the present invention can be 5' phosphorylated or can include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

Tethered Ligands

The RNA oligonucleotides of the present invention also include those with tethered ligands. The properties of a RNA oligonucleotide, including its pharmacological properties, can be influenced and tailored by the introduction of ligands, e.g. tethered ligands.

The ligands may be coupled, preferably covalently, either directly or indirectly via an intervening tether, to the RNA oligonucleotide. In preferred embodiments, the ligand is attached to the oligonucleotide via an intervening tether.

In preferred embodiments, a ligand alters the distribution, targeting or lifetime of a RNA oligonucleotide into which it is incorporated. In preferred embodiments a ligand provides an enhanced affinity for a selected target, e.g., molecule, cell or cell type, a cellular or organ compartment, tissue, organ or region of the body.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

A wide variety of ligands may be used. Ligands may include agents that allow for the specific targeting of the oligonucleotide; diagnostic compounds or reporter groups which allow for the monitoring of oligonucletotide distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., tritterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine.

Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB. The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one embodiment, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In another embodiment, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another embodiment, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

In a preferred embodiment, the ligand is an antibody or a fragment thereof which is specific for a moiety present in a cell to be targeted. The moiety may be a protein, a carbohydrate structure, a polynucleotide, or a combination thereof. The moiety may be secreted, associated with the plasma membrane (e.g., on the extracellular or intracellular surface), cytosolic, associated with intracellular organelles (e.g., ER, Golgi complex, mitochondria, endosome, lysosome, secretory vesicle) or nuclear. The antibody may be monoclonal or polyclonal. The antibody may be chemeric or humanized. The antibody may be a single chain antibody. The antibody fragment may be a Fab fragment, a F(ab')$_2$ fragment, or any fragments that retain the antigen-binding specificity of the intact antibody.

Immunostimulatory Activity

As used herein, "immunostimulatory activity" refers to the capability of a molecule or a composition to induce an immune response. In one aspect, the immunostimulatory activity refers to the type I-IFN-inducing activity, in particular, the IFN-α-inducing activity.

As used herein, "inducing an immune response" means initiating or causing an increase in one or more of B-cell activation, T-cell activation, natural killer cell activation, activation of antigen presenting cells (e.g., B cells, dendritic cells, monocytes and macrophages), cytokine production, chemokine production, specific cell surface marker expression, in particular, expression of co-stimulatory molecules. In one aspect, such an immune response involves the production of IL-12, in cells such as monocytes and myeloid dendritic cells (MDC).

As used herein, "IL-12-inducing activity" refers to the capability of a molecule or composition to induce IL-12 production from a cell capable of producing IL-12. Cells capable of producing IL-12 include, but are not limited to, activated B cells, activated T cells, myeloid dendritic cells, monocytes, macrophages, and various cell lines (e.g., B cell lines; monocyte cell lines; cells transfected with expression vectors for TLR-8 such as CHO cells, COS cells, HEK293 cells). Cells capable of producing IL-12 include those that express TLR8.

Gene Silencing Activity

As used herein, "gene silencing" refers to the downregulation or the abolition of the expression of a target gene. Gene silencing as used herein, occurs at the post-transcriptional level. Gene silencing may be directly or indirectly mediated by siRNA, shRNA and antisense RNA.

Both the antisense-strand of the siRNA and the antisense RNA have complementary to the target mRNA and are the effector strand of the gene silencing activity. The term complementary is well understood by those skilled in the art. For example, A is complementary to T, G is complementary to C, 5'-AG-3' is complementary to 5'-CT-3'.

The degree of complementarity between two oligonucleotides is the percentage of complementary bases in the overlapping region of the two oligonucleotides. The degree of complementarily can be determined manually or automatically by various engines such as BLAST. For example, ATCG has 100% complementarity to CGAT and CGATGG, and 75% complementarity to CGTT and CGTTGG. Furthermore, the degree of complementarity between a RNA oligonucleotide and any sequences present in the public databases (e.g., EMBL, GeneBank) can be determined by the BLAST program.

The degree of complementarity between the antisense strand of the siRNA or the antisense RNA and the target mRNA is at least 80% 81%, 82%, 83%, preferably at least 84%, 85%, 86%, 87%, 88%, more preferably at least 89%, 90%, 91%, 92%, 93%, even more preferably at least 94%, 95%, 96%, 97%, 98%, 99%, and most preferably 100%.

The gene silencing activity of a RNA oligonucleotide can be determined experimentally by methods well known in the art. For Example, the RNA oligonucleotide may be introduced into a cell by a method known in the art such as transfection and transduction; the mRNA level of the target gene can be determined by routine methods such as Northern blot analysis, quantitative PCR, RNase protection assay, and branching DNA; and the protein expression level can be determined by routine methods such as Western blotting, ELISA, and biological activity assays specific to the target protein. Furthermore, the mRNA level of all known and hypothetical genes can be determined at the global level using the microarray technology. Technologies in the field of proteonomics allow for the protein levels of a large number of genes to be determined at the global level as well.

Naked RNA oligonceotide may be transfected into a cell via electroporation. RNA oligonucleotide may be complexed with a complexation agent which facilitates the uptake of the oligonucletide into a cell. Such complexation agents include, but are not limited to cationic lipids (e.g., Lipofectamine, Oligofectamine, DOTAP), cationic peptides, and calcium phosphate.

Antisense RNA

As used herein, "antisense RNA" has the same definition as that established in the art. Antisense RNA is complementary to target mRNA and it thought to interfere with the translation of the target mRNA. Antisense RNA molecules are usually 18-50 nucleotides in length. Antisense RNA may be modified to have enhanced stability, nuclease resistance, target specificity and improved pharmacological properties.

Antisense RNA can be chemically synthesized, produced by in vitro transcription from linear (e.g. PCR products) or circular templates (e.g., viral or non-viral vectors), or produced by in vivo transcription from viral or non-viral vectors.

Disorder/Disease-Related Gene and Antigen

As used herein, "disorder/disease-related gene" refers to a gene that is expressed or overexpressed in a disease/disorder and that is not expressed or expressed in reduced amount under normal condition. For example, a mutant CF gene is expressed in cystic fibrosis patient but not in an individual without cystic fibrosis; ErbB2 (or Her2) is overexpressed in breast cancer cells compared to normal breast cells; a viral gene is expressed in infected cells but not in uninfected cells. The gene product of the disorder/disease-related gene is referred to herein as the "disorder/disease-related antigen".

Mammal

As used herein, the term "mammal" includes, without limitation, rats, mice, cats, dogs, horses, sheep, cattle, cows, pigs, rabbits, non-human primates, and humans.

Technology Platform

IL-12 and IFN-α are the two key cytokines to drive strong Th1 responses desired for effective immunotherapy of viral infection and cancer. While plasmacytoid dendritic cells (PDC) are responsible for the production of IFN-α, the major source for IL-12 are myeloid cells including monocytes, macrophages and myeloid dendritic cells. In several recent studies, RNA molecules were reported to induce IL-12 production in human immune cells, but the RNA sequence motif and the cellular subset responsible for IL-12 production has not been defined in these studies. Here we used a systematic approach to identify potent RNA motifs for IL-12 induction in TLR8-expressing cells.

We made use of the distinct expression pattern of TLR7 and TLR8 in human PDC (TLR7+TLR8−) and human monocytes (TLR7−TLR8+) [8]. A technology platform was developed that allowed screening of RNA oligonucleotides on a large scale. We designed a RNA oligonucleotide library that contained all possible 4-nucleotide (4-mer) motifs. By applying this library to our experimental system we were able to identify potent sequence motifs for inducing IL-12 production in human monocytes.

Our systematic approach (i.e., technological platform) is based on the following key features: i) the use of poly-L-Arg for complexation and transfection of RNA oligonucleotides; ii) identification of monocytes as the major source for IL-12 within PBMC and analysis of IL-12 production in supernatant of PBMC culture; iii) the generation of a 4mer library in the center of poly adenosine (poly A) RNA oligonucleotides; iv) the development of algorithms that use the 4mer library data matrix for prediction of IL-12-inducing activity of a RNA oligonucleotide. Our technical platform addresses the following key issues that are essential for successful analysis of IL-12-inducing activity of RNA oligonucleotides in PBMC:

The first key issue is the type of RNA transfection in PBMC. In the literature, cationic lipids such as lipofectamine or DOTAP are routinely used for the transfection of RNA oligonucleotides. However, RNA-cationic lipid complexes lead to rapid cell death especially of myeloid cells. Since myeloid cells represent the cellular source of IL-12 within PBMC (the source of IFN-α are PDC), cationic lipids are not useful in this setting. Searching for alternative techniques we compared the use of the cationic lipid lipofectamine with different types of cationic peptides (poly-His, poly-L-Lys, poly-L-Arg) for complexation of RNA. Only poly-L-Arg, but none of the other cationic polymers, potently supported the IL-12-inducing activity of the RNA oligonucleotides. By changing the length of the poly cationic peptide and the incubation time (i.e., the length of complex formation), a protocol could be established that allowed well-controlled and highly reproducible complex formation. Complex formation was validated by monitoring the size of complexes and the functional activity over a range of concentrations. It was found that poly-L-Arg which contain at least 24 amino acids are effective in introducing a RNA oligonucleotides into myeloid cells. Furthermore, complex formation between a RNA oligonucleotide and poly-L-Arg is achieved after 20 min of incubation. This type of RNA transfection did not affect the viability of myeloid cells and thus could be applied to PBMC without restrictions.

The second key issue of our technological platform was the in vitro system for testing the biological activity of RNA oligonucleotides. Primary monocytes were identified as the cellular source of IL-12 production within PBMC and where found to be stimulated by RNA oligonucleotides directly. Since primary monocytes exclusively express TLR8 but not TLR3, TLR7 or TLR9, a monocyte-based motif search is focused on motifs for TLR8. The use of primary immune cells was preferred over the use of TLR-transfected cell lines for several reasons: a) cell lines such as 293 cells may lack yet undefined adaptor proteins for oligonucleotide recognition by TLR or may lack downstream signaling molecules [11, 16]; b) reporter assays may not reflect the correct type of activity; c) internalization and intracellular distribution of oligonucleotides in cell lines may differ from primary immune cells. Therefore, the value of such cell line-based systems for screening the activity of RNA oligonucleotides is limited.

The third key issue of our technology platform was the generation of an oligonucleotide library. We demonstrate that a minimal length of 19 bases was required for optimal IL-12-inducing activity of RNA oligonucleotides; furthermore, we show that poly adenosine RNA oligonucleotides were completely inactive in terms of IL-12 induction in PBMC. Therefore, the search for the optimal motif for IL-12 induction was performed with a 19mer oligonucleotide on a poly adenosine sequence background. By adding increasing numbers of uridine (U) in the center of such an oligonucleotide we found that a 4mer motif in the center is sufficient to confer marked immunostimulatory activity (data not shown). The library of 193 RNA oligonucleotides used covered all 256 possible 4mer motifs. The reduction from 256 to 193 was possible because of redundant motifs caused by the poly adenosine flanking regions.

The fourth key feature of the technology platform was the generation of a data matrix and its mathematical analysis. Algorithms were developed that allowed the prediction of the IL-12 inducing activity of RNA oligonucleotides. The frequency of a given 4mer motif at a certain site within an oligonucleotide is only 1:256. Although the identification of the most active 4mer motifs can be used to generate potent immunostimulatory oligonucleotides, based on their low frequency of 1:256, the IL-12 indices of the 4mer motifs are less useful to predict the activity of a given oligonucleotide. Therefore, algorithms were established that are based on parts of the 4mer motif, namely 1, 2 or 3 bases either in a row (XXX) or with spacing (X*XX; XX*X). The highest predictive value was obtained by combining the information based on 3 bases (XXX, X*XX, XX*X). This algorithm described in the results section allowed a valuable prediction (r=0.78) of the IL-12 inducing activity of the 4mer motif library.

There is a number of applications for the information generated by using the technology platform: a) the 4mer motif data matrix can be used to design oligonucleotides with high IL-12-inducing activity; b) 4mer motifs with minimal/low IL-12-inducing activity can be used as preselection of potential inhibitory sequence motifs; c) the 3mer-based algorithm can be used to predict the IL-12-inducing activity of a given single-stranded RNA oligonucleotide; d) the 3mer-based algorithm can be used to maximize/optimize the immunostimulatory activity of single-stranded RNA oligonucleotides with other sequence requirements (such as antisense activity); e) use of 3mer-based algorithm to minimize (avoid) the IL-12-inducing activity of single-stranded RNA oligonucleotides with other sequence requirements (such as antisense activity).

In general, two major strategies for the therapeutic development of RNA oligonucleotides can be distinguished: i) gene silencing employing siRNA, shRNA or antisense RNA, and ii) inducing an immune response using immunostimulatory RNA (is RNA).

As shown in an earlier study of ours [10], double-stranded RNA oligonucleotides (including siRNA) are completely inactive in inducing IL-12, although they can be potent inducers of IFN-α. Therefore, only the avoidance of IFN-α-inducing activity is relevant for siRNA design as detailed in our co-pending application. On the other hand, in the preparation of IL-12-inducing single-stranded RNA oligonucleotides, the formation of double-stranded secondary structure via self-complementary sequence (including palindromic sequence) is to be avoided. Indeed, we show in our study that a single-strand 19mer RNA oligonucleotide lost its activity to induce IL-12 when a 12mer or a 16mer complementary strand is attached; furthermore, a palindromic RNA oligonucleotide was inactive in inducing IL-12. This aspect can be mathematically integrated in the algorithm used for the prediction and the design of IL-12-inducing oligonucleotides. On the other hand, the incorporation of a palindromic sequence into an immunostimulatory oligonucleotide can be used to direct the activity of the RNA oligonucleotide to the IFN-α-inducing activity.

It is important to note that a poly adenosine RNA oligonucleotide containing the best 4mer motif (UCGU) is 5-fold more active in inducing IL-12 than one of the most active immunostimulatory oligonucleotides in the literature, RNA9.2sense ([10]). This motif was found to be weak at inducing IFN-α in PDC. On the other hand, the most potent 4mer motif for IFN-α induction identified in our co-pending application, GUUC, shows only weak IL-12-inducing activity. The existence of two distinct optimal motifs for IFN-α and IL-12 induction together with the selective presence of TLR7 (but not TLR8) in PDC and TLR8 (but not TLR7) in monocytes strongly support the concept that two distinct receptors, TLR7 and TLR8, are responsible for IFN-α and IL-12 production, respectively, and that the two receptors have different ligand preference. However, we were able to identified 4mer motifs that are relatively potent at inducing both IFN-α and IL-12 production, suggesting that there are some common structural features that are recognized by both TLR7 and TLR8.

Of note, in a 19mer oligonucleotide, these two types of sequence motifs can be combined for eliciting optimal IFN-α and IL-12 responses at the same time.

The 4mer motifs that are more potent at inducing IFN-α than IL-12 include GCUC, GUCA, GUUC, GGUC, GUCC, GUCU, GUUU, CGUC, GCUU, GUGU.

The 4mer motifs that are more potent at inducing IL-12 than IFN-α include UCGU, GAUA, UGGC, UGCU, UGGU, UGCC, UUGC, UGAC, UAAU, UUAU.

The 4mer motifs that are potent at inducing both IL-12 than IFN-α include GUUG, GGUU, UUGU, GGUA, CUGU, UGUC, UGUA, UGUU, UGUG, UAGU.

Furthermore, one can hypothesize that distinct inhibitory sequence motifs exist for TLR7 and TLR8, and that by combining inhibitory motifs for TLR7 and active motifs for TLR8 or vice versa, the activity of a RNA oligonucleotide can be directed to exclusive TLR7 or TLR8 activity. Combining inhibitory motifs for TLR7 and TLR8 would lead to minimized immunostimulatory activity of a RNA oligonucleotide, which may be desired in the preparation of certain gene silencing oligonucleotides.

Distinct sequence motifs for TLR7 and TLR8 activation have not been previously reported. To date, there are only two publications describing the identification of specific sequence motifs responsible for the immunological activity of RNA [10, 17]. However, in both publications, the sequence motif was identified based on the IFN-α- but not IL-12-inducing activity. In one publication, Judge and colleagues propose that a sequence motif, UGUGU, is responsible for the IFN-α-inducing activity of a RNA oligonucleotide [17]. In our own publication we identified a 9mer sequence motif to be responsible for the immunological activity of the ssRNA oligonucleotide RNA9.2 sense (5"-AGC UUA ACC UGU CCU UCA A-3" (SEQ ID NO: 194), 9mer motif underlined). Heil and colleagues did not claim a specific sequence motif but attributed the immmunological activity of RNA oligonucleotides to a high content of G and U within the sequence [11]. Sioud and colleagues tested a large panel of RNA oligonucleotides for TNF-α and IL-6 production in PBMC, but only one sequence was tested for IFN-a induction [18]. In mice, two publications report IFN-a induction by RNA oligonucleotides [12, 19].

In the six studies described above, IL-12 was examined by Heil [11] in human PBMC and by Heil, by Diebold and by Barchet in murine dendritic cells [11, 12, 19] without disclosing any specific sequence motifs. In one other study, sequence-specific induction of IL-12 in primary monocytes by RNA oligonucleotide was reported [16]. In this study, the authors report that the induction of IL-12 by RNA oligonucleotides is CpG specific. Inversion of CG to GC within the sequence motif used (5"-GGUGCAUCGAUG-CAGGGGGG-3" (SEQ ID NO: 195); CpG motif underlined, palindrome in bold) abolished the activity of the oligonucleotide. Furthermore, methylation of the C abrogated the activity. The sequence context was defined as an AU dinucleotide at the 5" of the CG and a poly G sequence at the 3"end of the RNA oligonucleotide. RNA oligonucleotides with a complete phosphorothioate modification for stabilization against nucleases did not require complexation or transfection; in contrast, unmodified RNA oligonucleotides were only active when transfected with cationic lipids. In addition to the phosphorothioate backbone, RNA oligonucleotides were protected by 2-bis(acetoxyethoxy)-methyl ether. Our own results do not confirm the strict CG dependence of this effect. The best single prediction formula of active motifs in our study is UXGU, in which the X is preferentially C, G or U. Even the motif UGCU (which in their study was an inactive sequence) is among the most active sequence motifs in our study. In contrast to their study, the presence of palindromic sequences in our hands abolish the IL-12 inducing activity. Furthermore, poly G is not necessary in our approach. Together, in their study [16] a number of additional factors (phosphorothioate backbone, palindromic sequence, protection by 2-bis(acetoxyethoxy)-methyl ether) seem to affect the immunological activity of their oligonucleotides in a way that the pure sequence specificity seems to be obscured and can obviously not be separated correctly from other influencing factors.

Several studies report that long single-stranded RNA such as mRNA is immunologically active. Koski and colleagues showed that RNA derived from bacterial but not eukaryotic sources, when transfected into human monocyte-derived dendritic cell precursors, induced IL-12 secretion, and that lack of activity of vertebrate mRNA depends on the presence of a poly(A) tail. Furthermore they report that in vitro-transcribed mRNA mimics the structure of bacterial mRNA in the lack of a long 3'-poly(A) tail [20]. Scheel and colleagues demonstrated that monocytes are activated by protamine-condensed mRNA (long single-stranded RNA) [21, 22].

Protamine used in the study of Scheel and colleagues for complexation of long single-stranded RNA [21, 22] is a long cationic protein. In the literature, also short cationic peptides were described to complex long nucleic acids resulting for example in enhanced delivery of plasmid DNA [23]. The cationic peptide poly-L-Arg is known to be effectively internalized into the endosomal compartment [24], which facilitates cellular delivery of oligonucleotides complexed to poly-L-Arg [25]. However, poly-L-Arg has never been described for the delivery of RNA oligonucleotides.

In conclusion, the use of poly-L-Arg for the delivery of RNA oligonucleotides to myeloid cells without inducing cell death for the first time allowed a valid search for RNA motif(s) recognized by TLR8-positive (and TLR7-negative) monocytes. The availability of distinct motifs for IL-12 and IFN-α (co-pending application) induction allows for the first time selective and/or combined induction of these two key Th1 cytokines in the human immune system, thereby filling the gap left by CpG DNA oligonucleotides which fail to induce IL-12 in human immune cells. Our results may have great impact on the design, the understanding and the clinical development of immunostimulatory RNA (is RNA).

Method for Determining the Immunostimulatory Activity of an RNA Oligonucleotide

The present invention provides a method for determining the immunostimulatory activity, in particular, the IL-12-inducing activity, of a RNA oligonucleotide, comprising the steps of:
  (a) complexing the RNA oligonucleotide with a complexation agent;
  (b) contacting a cell with the complexed RNA oligonucleotide, wherein the cell expresses TLR8; and
  (c) determining the amount of IL-12 produced by the cell of step (b), an increase of IL-12 production indicating immunostimulatory activity of the RNA oligonucleotide.

In one embodiment of the invention, the complexation agent is a polycationic peptide, preferably poly-L-arginine (poly-L-Arg). In one embodiment, the polycationic peptide, in particular, poly-L-Arg, is at least 24 amino acids in length (SEQ ID NO: 447). The polycationic peptide, in particular, poly-L Arg, may be a heterogeneous mixture of peptides of different lengths.

The cells expressing TLR8 include, but are not limited to, peripheral blood mononuclear cells (PBMC), myeloid dendritic cells (MDC), macrophages, monocytes, B cells, and cells containing exogenous DNA which directs the expression of TLR8 such as transfected CHO, HEK293, and COS cells.

In one embodiment of the invention, the cell is a mammalian cell, preferably a human cell or a cell of human origin.

Method for Predicting the Immunostimulatory Activity of a RNA Oligonucleotide

The present invention provides a method for predicting the immunostimulatory activity, in particular, the IL-12-inducing activity, of a single-stranded RNA oligonucleotide, comprising the steps of:
  (a) identifying all possible 3-nucleotide (3mer) motifs contained in the oligonucleotide
    (i) for a 3mer motif which appears in Table 5, assing an IL-12 point score according to Table 5;
    (ii) for a 3mer motif which does not appear in Table 5, assign an IL-12 point score of 0;
  (b) assigning an IL-12 point score for each individual 3mer motif;
  (c) assigning the sum of the IL-12 point scores of individual 3mer motifs as the IL-12 score of the oligonucleotide; and
  (d) assigning to the oligonucleotide a high immunostimulatory activity if the IL-12 score is at least 93.53, an intermediate immunostimulatory activity if the IL-12 score is between −28 and 93.53, and a low immunostimulatory activity if the IL-12 score is at most −28, when n=6;
    assigning to the oligonucleotide a high immunostimulatory activity if the IL-12 score is at least 107.77, an intermediate immunostimulatory activity if the IL-12 score is between −31 and 107.77, and a low immunostimulatory activity if the IL-12 score is at most −31, when n=7;
    assigning to the oligonucleotide a high immunostimulatory activity if the IL-12 score is at least 121, an intermediate immunostimulatory activity if the IL-12 score is between −34 and 121, and a low immunostimulatory activity if the IL-12 score is at most −34, when n=8;
    assigning to the oligonucleotide a high immunostimulatory activity if the IL-12 score is at least 121.98, an intermediate immunostimulatory activity if the IL-12 score is between −36 and 121.98, and a low immunostimulatory activity if the IL-12 score is at most −36, when n=9;

assigning to the oligonucleotide a high immunostimulatory activity if the IL-12 score is at least 8.4064×n+66.958, an intermediate immunostimulatory activity if the IL-12 score is between 0.0468×n$^2$-2.3103×n−23.244 and 8.4064×n+66.958, and a low immunostimulatory activity if the IL-12 score is at most 0.0468×n$^2$-2.3103×n−23.244, when n is greater than 9, wherein n is the length of the oligonucleotide.

The present invention also provides a method of assigning an IL-12 score to a RNA oligonucleotide comprising steps (a)-(c) described above.

A single-stranded RNA oligonucleotide of the length n is broken up into all possible 3mer motifs of the following configuration. XXX, X*XX, XX*X. This will result in a total number of (3*n)−4 possible 3mer motifs.

For example, the 20mer ssRNA oligonucleotide 5'-AACGCCCGGCUCAUUACGUC-3'SEQ ID NO: 196 can be broken up into the following 18 3mer motifs 5'-XXX-3': AAC, ACG, CGC, GCC, CCC, CCG, CGG, GGC, GCU, CUC, UCA, CAU, AUU, UUA, UAC, ACG, CGU, GUC; the following 17 3mer motifs 5'-X*XX-3': A*AG, A*CC, C*GC, G*CC, C*CG, C*CG, C*GC, G*GU, G*CC, C*UA, U*CU, C*AU, A*UA, U*UC, U*AG, A*CU, C*GC; and the following 17 3mer motifs 5'-XX-*X-3': AC*G, AG*C, CC*C, GC*C, CC*G, CG*G, CG*C, GC*U, GU*C, CC*A, UA*U, CU*U, AU*A, UA*C, UC*G, AG*U, CU*C Subsequently all of the obtained 3mer motifs are compared to the IL-12 point score matrix (Table 5).

TABLE 5

IL-12 point score matrix for 3mer motifs. * can be any one of the nucleotides A, U, G and C.

| Sequence 5'→ 3' | IL-12 Point score |
|---|---|
| AAC | −4 |
| AAU | 4 |
| ACA | −4 |
| ACC | −5 |
| ACG | −4 |
| AGA | −3 |
| AGU | 7 |
| AUG | 8 |
| CAA | −2 |
| CCA | −4 |
| CGA | −4 |
| CGU | 6 |
| GAA | −2 |
| GGU | 11 |
| GUA | 10 |
| GUG | 6 |
| GUU | 13 |
| UAA | 4 |
| UGA | 4 |
| UGC | 9 |
| UGG | 8 |
| UGU | 11 |
| UUG | 12 |
| AA*C | −3 |
| AA*U | 4 |
| AC*A | −4 |
| AC*C | −5 |
| AG*U | 6 |
| AU*G | 9 |
| AU*U | 5 |
| CA*A | −2 |
| CC*A | −4 |
| GU*A | 8 |

TABLE 5-continued

IL-12 point score matrix for 3mer motifs. * can be any one of the nucleotides A, U, G and C.

| Sequence 5'→ 3' | IL-12 Point score |
|---|---|
| GU*G | 14 |
| GU*U | 9 |
| UA*A | 4 |
| UC*U | 13 |
| UG*A | 5 |
| UG*C | 13 |
| UG*U | 20 |
| UU*A | 4 |
| A*AC | −4 |
| A*AU | 3 |
| A*CA | −4 |
| A*CC | −5 |
| A*GU | 7 |
| A*UG | 8 |
| A*UU | 4 |
| C*AA | −2 |
| C*CA | −5 |
| C*GA | −5 |
| G*UA | 8 |
| G*UG | 11 |
| G*UU | 8 |
| U*AA | 3 |
| U*AU | 8 |
| U*GC | 11 |
| U*GU | 27 |
| U*UA | 5 |

Whenever a 3mer motif is present in the IL-12 point score matrix, the listed point score is added to the so-called predicted IL-12 score of the oligonucleotide analyzed. Whenever a 3mer motif is absent from the IL-12 point score matrix, the motif get s point score of 0. Therefore, the predicted IL-12 score of a given ssRNA oligonucleotide is the sum of IL-12 points scores of all 3mer motifs that are present in the IL-12 point score matrix.

For example, for the 20mer ssRNA oligonucleotide 5'-AACGCCCGGCUCAUUACGUC-3' (SEQ ID NO: 196) a predicted IL-12 score can be calculated as follows:

| 3mer motifs in the 20mer ssRNA oligonucleotide 5'-AACGCCCGGCUCA-UUACGUC-3' (SEQ ID NO: 196) | presence (✓) or absence (Ø) in the IL-12 point score matrix | predicted IL-12 score |
|---|---|---|
| AAC | ✓ | −4 |
| AAU | Ø | 0 |
| ACA | Ø | 0 |
| ACC | Ø | 0 |
| ACG | ✓ | −8 |
| AGA | Ø | 0 |
| AGU | Ø | 0 |
| AUG | Ø | 0 |
| CAA | Ø | 0 |
| CCA | Ø | 0 |
| CGA | Ø | 0 |
| CGU | ✓ | 6 |
| GAA | Ø | 0 |
| GGU | Ø | 0 |
| GUA | Ø | 0 |
| GUG | Ø | 0 |
| GUU | Ø | 0 |
| UAA | Ø | 0 |
| UGA | Ø | 0 |
| UGC | Ø | 0 |
| UGG | Ø | 0 |
| UGU | Ø | 0 |
| UUG | Ø | 0 |
| AA*C | Ø | 0 |

-continued

| 3mer motifs in the 20mer ssRNA oligonucleotide 5'-AACGCCCGGCUCA-UUACGUC-3' (SEQ ID NO: 196) | presence (✓) or absence (Ø) in the IL-12 point score matrix | predicted IL-12 score |
|---|---|---|
| AA*U | Ø | 0 |
| AC*A | Ø | 0 |
| AC*C | ✓ | −5 |
| AG*U | Ø | 0 |
| AU*G | Ø | 0 |
| AU*U | Ø | 0 |
| CA*A | Ø | 0 |
| CC*A | Ø | 0 |
| GU*A | Ø | 0 |
| GU*G | Ø | 0 |
| GU*U | Ø | 0 |
| UA*A | Ø | 0 |
| UC*U | ✓ | 13 |
| UG*A | Ø | 0 |
| UG*C | Ø | 0 |
| UG*U | Ø | 0 |
| UU*A | Ø | 0 |
| A*AC | Ø | 0 |
| A*AU | Ø | 0 |
| A*CA | Ø | 0 |
| A*CC | Ø | 0 |
| A*GU | ✓ | 7 |
| A*UG | Ø | 0 |
| A*UU | Ø | 0 |
| C*AA | Ø | 0 |
| C*CA | ✓ | −5 |
| C*GA | Ø | 0 |
| G*UA | Ø | 0 |
| G*UG | Ø | 0 |
| G*UU | Ø | 0 |
| U*AA | Ø | 0 |
| U*AU | ✓ | 8 |
| U*GC | Ø | 0 |
| U*GU | Ø | 0 |
| U*UA | Ø | 0 |
| overall | | 12 |

Method for Designing and Preparing RNA Oligonucleotides

The present application provides a method for preparing an ssRNA oligonucleotide having immunostimulatory activity, in particular, high IL-12-inducing activity, comprising the steps of:
(a) providing candidate oligonucleotide sequence(s);
(b) identifying oligonucleotide sequence(s) with high immunostimulatory activity predicted according to the method of prediction described in the previous section;
(c) preparing the RNA oligonucleotide(s) identified for high immunostimulatory activity in step (b); and
(d) optionally testing the immunostimulatory activity of the RNA oligonucleotide(s) prepared in step (c) according to the method of determination described previously; and
(e) further optionally modifying the oligonucleotide(s) to optimize the immunostimulatory activity.

The present application also provides a method for preparing an ssRNA oligonucleotide having low immunostimulatory activity, in particular, low IL-12-inducing activity, comprising the steps of:
(a) providing candidate oligonucleotide sequence(s);
(b) identifying oligonucleotide sequence(s) with low immunostimulatory activity predicted according to the method of prediction described in the previous section;
(c) preparing the RNA oligonucleotide(s) identified for low immunostimulatory activity in step (b); and
(d) optionally testing the RNA oligonucleotide(s) prepared in step (c) for the lack of immunostimulatory activity according to the method of determination described previously; and
(e) further optionally modifying the oligonucleotide(s) to minimize the immunostimulatory activity.

The present application further provides a method for preparing a single-stranded RNA oligonucleotide having high immunostimulatory activity, in particular, high IL-12-inducing activity, comprising the steps of:
(a) providing an oligonucleotide sequence which comprises at least one, preferably at least two, more preferably at least three, even more preferably at least four, of the 4-nucleotide (4-mer) motifs selected from the group consisting of:

UCGU (No. 1), GUUG (No. 2), UGGU (No. 3),

UGGC (No. 4), GGUA (No. 5), UGAU (No. 6),

UGCU (No. 7), UUGC (No. 8), UUGU (No. 9),

UAGU (No. 10), GGUU (No. 11), GUUU (No. 12),

UGUG (No. 13), GUGU (No. 14), UGCC (No. 15),

GUAU (No. 16), GUGC (No. 17), UGUA (No. 18),

UGUC (No. 19), CUGU (No. 20), UGAC (No. 21),

UGUU (No. 22), UAAU (No. 23), GUAG (No. 24),

UCUU (No. 25), UUGG (No. 26), UUUG (No. 27),

GGAU (No. 28), UUUU (No. 29), CGUU (No. 30),

UUAU (No. 31), GUUC (No. 32), GUGG (No. 33),

GGUG (No. 34), UAUU (No. 35), UCUG (No. 36),

GUAC (No. 37), UAGG (No. 38), UCUC (No. 39),

UAGC (No. 40), UAUC (No. 41), CUAU (No. 42),

UACU (No. 43), CGGU (No. 44), UGCG (No. 45),

UUUC (No. 46), UAUG (No. 47), UAAG (No. 48),

UACC (No. 49), UUAG (No. 50), GCUU (No. 51),

CAGU (No. 52), UGAG (No. 53), GAUU (No. 54),

GAGU (No. 55), GUUA (No. 56), UGCA (No. 57),

UUCU (No. 58), GCCU (No. 59), GGUC (No. 60),

GGCU (No. 61), UUAC (No. 62), UCAU (No. 63),

GCGU (No. 64), GCAU (No. 65), GAUG (No. 66),

GUCU (No. 67), CGUA (No. 68), CGAU (No. 69), wherein the nucleotide sequences of the motifs are 5'→3',
wherein the oligonucleotide is between 6 and 64, preferably between 12 and 50, more preferably between 14 and 40, even more preferably between 16 and 36, and most preferably between 18 and 30 nucleotides in length,
wherein the oligonucleotide has an IL-12 score of at least 93.53 when n=6; at least 107.77 when n=7; at least 121 when n=8; at least 121.98 when n=9; at least 8.4064×n+ 66.985 when n is greater than 9, wherein the IL-12 score is assigned according to the method described above, wherein n is the length of the oligonucleotide;
(b) preparing the RNA oligonucleotide of step (a); and
(c) optionally testing the immunostimulatory activity of the RNA oligonucleotide prepared in step (b) according to the method of determination described previously; and (d) further optionally modifying the oligonucleotide to optimize the immunostimulatory activity.

The ssRNA oligonucleotide can have other functionalities such as the gene silencing activity. The ssRNA oligonucleotide may be an antisense RNA.

The methods provided by the present application can be used to prepare immunostimulatory RNA oligonucleotides and antisense RNA with high or low immunostimulatory activity.

Some of the RNA oligonucleotides which have low immunostimulatory activity, i.e., the non-immunostimulatory oligonucleotides, may in fact have inhibitory activity against immune activation. Such an immunoinhibitory oligonucleotide may be able to prevent immune activation induced by an immunostimulatory oligonucleotide when used in combination.

RNA oligonucleotides can be prepared by methods including, but are not limited to, chemical synthesis, in vitro and in vivo transcription from linear templates (e.g., PCR product) and circular templates (e.g., viral or non-viral vectors).

Method for Preparing Antisense RNA Having High or Low Immunostimulatory Activity The present invention provides a method for preparing an antisense RNA having gene silencing activity for a target gene and having immunostimulatory activity, in particular, IL-12-inducing activity, comprising the steps of:
  (a) identifying all potential antisense sequences for a target mRNA;
  (b) identifying antisense sequences that have gene silencing activity;
  (c) predicting the immunostimulatory activity for the antisense sequences identified in step (b);
  (d) identifying antisense RNA sequences which have an IL-12 score of at least $8.4064 \times n + 66.958$, wherein the IL-12 score is assigned according to the method described above, and wherein n is the length of the sequence and n is between 18 and 50;
  (e) decreasing the IL-12 score threshold by 1 if no antisense sequence is identified in step (d), until at least one antisense sequence is identified;
  (f) preparing the antisense RNA identified in step (d) or (e);
  (g) optionally testing the gene silencing and/or the immunostimulatory activity of the antisense prepared in (f);
  (h) further optionally modify the antisense RNA prepared in (f) to optimize the gene silencing and/or immunostimulatory activity.

The present invention also provides an alternative method for preparing an antisense RNA with gene silencing activity and immunostimulatory activity, comprising the steps of:
  (a) identifying all potential antisense sequences for a target mRNA;
  (b) predicting the immunostimulatory activity for all of the potential antisense sequences identified in (a);
  (c) identifying 10 potential antisense sequences with the highest IL-12 scores;
  (d) identifying antisense sequences with gene silencing activity among the 10 potential antisense sequences identified in step (c);
  (e) identifying 10 potential antisense sequences with the next highest IL-12 scores if no antisense sequence can be identified in step (d); repeat steps (d) and (e) until at least one antisense sequence is identified;
  (f) preparing the antisense RNA identified in step (d) or (e);
  (g) optionally testing the gene silencing and/or the immunostimulatory activity of the antisense RNA prepared in (f);
  (h) further optionally modify the antisense RNA prepared in (f) to optimize the gene silencing and/or immunostimulatory activity.

The present invention further provides a method for preparing an antisense RNA having gene silencing activity for a target gene and having low (or minimal) immunostimulatory activity, in particular, IL-12-inducing activity, comprising the steps of:
  (a) identifying all potential antisense sequences for a target mRNA;
  (b) identifying antisense sequences that have gene silencing activity;
  (c) predicting the immunostimulatory activity for the antisense sequences identified in step (b);
  (d) identifying antisense sequences which have an IL-12 score of at most $1.9763 \times n - 30.643$, wherein the IL-12 score is assigned according to the method described above, and wherein n is the length of the sequence and n is between 18 and 50;
  (e) increasing the IL-12 score threshold by 1 if no antisense sequence is identified in step (b), until at least one antisense sequence is identified;
  (f) preparing the antisense RNA identified in step (d) or (e);
  (g) optionally testing the gene silencing and/or the immunostimulatory activity of the antisense RNA prepared in (f);
  (h) further optionally modify the antisense RNA prepared in (f) to optimize the gene silencing activity and/or to minimize the immunostimulatory activity.

The present invention also provide an alternative method for preparing an antisense RNA with gene silencing activity and low (or minimal) immunostimulatory activity, comprising the steps of:
  (a) identifying all potential antisense sequences for a target mRNA;
  (b) predicting the immunostimulatory activity for all of the potential antisense sequences identified in (a);
  (c) identifying 10 potential antisense sequences with the lowest IL-12 scores;
  (d) identifying antisense sequences with gene silencing activity among the 10 potential antisense sequences identified in step (c);
  (e) identifying 10 potential antisense sequences with the next lowest IL-12 scores if no antisense sequence can be identified in step (d); repeat steps (d) and (e) until at least one antisense sequence is identified;
  (f) preparing the antisense RNA identified in step (d) or (e);
  (g) optionally testing the gene silencing and/or the immunostimulatory activity of the antisense RNA prepared in (f);
  (h) further optionally modify the antisense RNA prepared in (f) to optimize the gene silencing activity and/or to minimize the immunostimulatory activity.

Candidate (potential) antisense sequences with gene silencing activity for a given gene can be identified using methods known to those skilled in the art. Furthermore, the gene silencing activity of an antisense RNA may be determined experimentally.

The gene silencing activity of an antisense can be determined experimentally by methods well known in the art. For Example, the antisense RNA oligonucleotide may be introduced into a cell by a method known in the art such as transfection and transduction; the mRNA level of the target gene can be determined by routine methods such as Northern blot analysis, quantitative PCR, RNase protection assay, and branching DNA; and the protein expression level can be determined by routine methods such as Western blotting, ELISA, and biological activity assays specific to the target protein. Furthermore, the mRNA level of all known and hypothetical genes can be determined at the global level using the microarray technology. Technologies in the field of proteonomics allow for the protein levels of a large number of genes to be determined at the global level as well.

The antisense RNA can be prepared by methods including, but are not limited to, chemical synthesis, in vitro and in vivo transcription from PCR products and viral or non-viral vectors.

Immunostimulatory RNA Oligonucleotides

The present invention provides an immunostimulatory RNA oligonucleotide having immunostimulatory activity, in particular, IL-12-inducing activity, comprising at least one, preferably at least two, more preferably at least three, even more preferably at least four, even more preferably at least five, and most preferably at least six, of the 4-nucleotide (4mer) motifs selected from the group consisting of:

```
UCGU (No. 1), GUUG (No. 2), UGGU (No. 3),

UGGC (No. 4), GGUA (No. 5), UGAU (No. 6),

UGCU (No. 7), UUGC (No. 8), UUGU (No. 9),

UAGU (No. 10), GGUU (No. 11), GUUU (No. 12),

UGUG (No. 13), GUGU (No. 14), UGCC (No. 15),

GUAU (No. 16), GUGC (No. 17), UGUA (No. 18),

UGUC (No. 19), CUGU (No. 20), UGAC (No. 21),

UGUU (No. 22), UAAU (No. 23), GUAG (No. 24),

UCUU (No. 25), UUGG (No. 26), UUUG (No. 27),

GGAU (No. 28), UUUU (No. 29), CGUU (No. 30),

UUAU (No. 31), GUUC (No. 32), GUGG (No. 33),

GGUG (No. 34), UAUU (No. 35), UCUG (No. 36),

GUAC (No. 37), UAGG (No. 38), UCUC (No. 39),

UAGC (No. 40), UAUC (No. 41), CUAU (No. 42),

UACU (No. 43), CGGU (No. 44), UGCG (No. 45),

UUUC (No. 46), UAUG (No. 47), UAAG (No. 48),

UACC (No. 49), UUAG (No. 50), GCUU (No. 51),

CAGU (No. 52), UGAG (No. 53), GAUU (No. 54),

GAGU (No. 55), GUUA (No. 56), UGCA (No. 57),

UUCU (No. 58), GCCU (No. 59), GGUC (No. 60),

GGCU (No. 61), UUAC (No. 62), UCAU (No. 63),

GCGU (No. 64), GCAU (No. 65), GAUG (No. 66),

GUCU (No. 67), CGUA (No. 68), CGAU (No. 69),
``` wherein the nucleotide sequences of the motifs are 5'→3', wherein the oligonucleotide is between 6 and 64, preferably between 12 and 50, more preferably between 14 and 40, even more preferably between 16 and 36, and most preferably between 18 and 30 nucleotides in length, wherein the oligonucleotide has an IL-12 score of at least 93.53 when n=6; at least 107.77 when n=7; at least 121 when n=8; at least 121.98 when n=9; at least 8.4064×n+66.985 when n is greater than 9, wherein the IL-12 score is assigned according to the method described above, wherein n is the length of the oligonucleotide, and wherein the oligonucleotide is not 5'-UUGAUGUGU-UUAGUCGCUA-3' SEQ ID NO: 197) ([17]), 5'-GCAC-CACUAGUUGGUUGUC-3' (SEQ ID NO: 198) ([18]), 5'-UGCUAUUGGUGAUUGCCUC-3' (SEQ ID NO: 199) ([18]), 5'-GUUGUAGUUGUACUCCAGC-3' (SEQ ID NO: 200) ([18]), 5'-UGGUUG-3' (WO 03/086280), 5'-GUU-GUGGUUGUGGUUGUG-3' (SEQ ID NO: 201) (WO 03/086280).

In one embodiment, the 4mer motifs are selected from the group consisting of No. 1-11, preferably No. 1-10, No. 1-9, No. 1-8, more preferably No. 1-7, No. 1-6, No. 1-5, No. 1-4, even more preferably No. 1-3, No. 1-2 of the above-listed 4mer motifs, most preferably, the 4mer motif is UCGU.

The immunostimulatory RNA oligonucleotide of the invention may comprise one or more copies of the same 4mer motif, or one or more copies of different 4mer motifs.

The present invention also provide an immunostimulatory RNA oligonucleotide having immunostimulatory, in particular, IL-12-inducing activity, comprising at least one, preferably at least two, more preferably at least three, even more preferably at least four, even more preferably at least five, most preferably at least six, of the 4mer motifs selected from the group consisting of No. 1-11 of the 4mer motifs, wherein the spacer nucleotides which are not part of any of the 4mer motif(s) are identical, and wherein the spacer nucleotide is selected from the group consisting of A, T, C, G and variants and derivatives thereof.

In one embodiment, the spacer nucleotide is A or a derivative thereof.

The immunostimulatory RNA oligonucleotide of the invention can comprise one or more copies of one type of 4mer motif (e.g., UCGU) on a poly A backbone. Examples of such an oligonucleotide includes, but are not limited to:

AAAAAAAUCGUAAAAAAAA (SEQ ID NO: 202)

AAAUCGUAAAAAAAAAAAA (SEQ ID NO: 203)

AAAAAAAAAAAAUCGUAAA (SEQ ID NO: 204)

AAAUCGUAAAAAUCGUAAA (SEQ ID NO: 205)

UCGUAAAUCGUAAAUCGUA (SEQ ID NO: 206)

In another embodiment, the immunostimulatory RNA oligonucleotide of the invention can comprise one or more copies of more than one type of 4mer motif (e.g., UGAU, GGUA, UGGC, UGGU, GUUG, UCGU) on a poly A backbone. Examples of such an oligonucleotide includes, but are not limited to:

AUGGUAAAGUUGAAAUCGU (SEQ ID NO: 207)

AUGGUAAUGGUAAAGUUGA (SEQ ID NO: 208)

AAAUGAUAAAGGUAAAAUGGCAAAUGGUAAAGUUGAAAUCGUAAA (SEQ ID NO: 209)

The more than one 4mer motifs in an immunostimulatory RNA oligonucleotide may overlap. For example, AAAUGAUGGCAAAAAA (SEQ ID NO: 210).

Examples of the immunostimulatory RNA olignucleotide of the invention include, but are not limited to:

```
aaagguuaaaaaagguuaaa       (SEQ ID NO: 246)
aaauuguaaaaaagguuaaa       (SEQ ID NO: 247)
aaauugcaaaaaagguuaaa       (SEQ ID NO: 248)
aaaugcuaaaaaagguuaaa       (SEQ ID NO: 249)
aaaugauaaaaaagguuaaa       (SEQ ID NO: 250)
aaagguaaaaaagguuaaa        (SEQ ID NO: 251)
aaauggcaaaaaagguuaaa       (SEQ ID NO: 252)
aaaugguaaaaaagguuaaa       (SEQ ID NO: 253)
aaaguugaaaaaagguuaaa       (SEQ ID NO: 254)
aaaucguaaaaaagguuaaa       (SEQ ID NO: 255)
aaagguuaaaaaauuguaaa       (SEQ ID NO: 256)
aaauuguaaaaaauuguaaa       (SEQ ID NO: 257)
aaauugcaaaaaauuguaaa       (SEQ ID NO: 258)
aaaugcuaaaaaauuguaaa       (SEQ ID NO: 259)
aaaugauaaaaaauuguaaa       (SEQ ID NO: 260)
aaagguaaaaaauuguaaa        (SEQ ID NO: 261)
aaauggcaaaaaauuguaaa       (SEQ ID NO: 262)
aaaugguaaaaaauuguaaa       (SEQ ID NO: 263)
aaaguugaaaaaauuguaaa       (SEQ ID NO: 264)
aaaucguaaaaaauuguaaa       (SEQ ID NO: 265)
aaagguuaaaaaauugcaaa       (SEQ ID NO: 266)
aaauuguaaaaaauugcaaa       (SEQ ID NO: 267)
aaauugcaaaaaauugcaaa       (SEQ ID NO: 268)
aaaugcuaaaaaauugcaaa       (SEQ ID NO: 269)
aaaugauaaaaaauugcaaa       (SEQ ID NO: 270)
aaagguaaaaaauugcaaa        (SEQ ID NO: 271)
aaauggcaaaaaauugcaaa       (SEQ ID NO: 272)
aaauggu aaaaaauugcaaa      (SEQ ID NO: 273)
aaaguugaaaaaauugcaaa       (SEQ ID NO: 274)
aaaucguaaaaaauugcaaa       (SEQ ID NO: 275)
aaagguuaaaaaaugcuaaa       (SEQ ID NO: 276)
aaauuguaaaaaaugcuaaa       (SEQ ID NO: 277)
aaauugcaaaaaaugcuaaa       (SEQ ID NO: 278)
aaaugcuaaaaaaugcuaaa       (SEQ ID NO: 279)
aaaugauaaaaaaugcuaaa       (SEQ ID NO: 280)
aaagguaaaaaaugcuaaa        (SEQ ID NO: 281)
aaauggcaaaaaaugcuaaa       (SEQ ID NO: 282)
aaaugguaaaaaaugcuaaa       (SEQ ID NO: 283)
aaaguugaaaaaaugcuaaa       (SEQ ID NO: 284)
aaaucguaaaaaaugcuaaa       (SEQ ID NO: 285)
aaagguuaaaaaaugauaaa       (SEQ ID NO: 286)
aaauuguaaaaaaugauaaa       (SEQ ID NO: 287)
aaauugcaaaaaaugauaaa       (SEQ ID NO: 288)
aaaugcuaaaaaaugauaaa       (SEQ ID NO: 289)
aaaugauaaaaaaugauaaa       (SEQ ID NO: 290)
aaagguaaaaaaugauaaa        (SEQ ID NO: 291)
aaauggcaaaaaaugauaaa       (SEQ ID NO: 292)
aaaugguaaaaaaugauaaa       (SEQ ID NO: 293)
aaaguugaaaaaaugauaaa       (SEQ ID NO: 294)
aaaucguaaaaaaugauaaa       (SEQ ID NO: 295)
aaagguuaaaaaagguaaa        (SEQ ID NO: 296)
aaauuguaaaaaagguaaa        (SEQ ID NO: 297)
aaauugcaaaaaagguaaa        (SEQ ID NO: 298)
aaaugcuaaaaaagguaaa        (SEQ ID NO: 299)
aaaugauaaaaaagguaaa        (SEQ ID NO: 300)
aaagguaaaaaagguaaa         (SEQ ID NO: 301)
aaauggcaaaaaagguaaa        (SEQ ID NO: 302)
aaauggu aaaaaagguaaa       (SEQ ID NO: 303)
aaaguugaaaaaagguaaa        (SEQ ID NO: 304)
aaaucguaaaaaagguaaa        (SEQ ID NO: 305)
aaagguuaaaaaauggcaaa       (SEQ ID NO: 306)
aaauuguaaaaaauggcaaa       (SEQ ID NO: 307)
aaauugcaaaaaauggcaaa       (SEQ ID NO: 308)
aaaugcuaaaaaauggcaaa       (SEQ ID NO: 309)
aaaugauaaaaaauggcaaa       (SEQ ID NO: 310)
aaagguaaaaaauggcaaa        (SEQ ID NO: 311)
aaauggcaaaaaauggcaaa       (SEQ ID NO: 312)
aaauggu aaaaaauggcaaa      (SEQ ID NO: 313)
aaaguugaaaaaauggcaaa       (SEQ ID NO: 314)
aaaucguaaaaaauggcaaa       (SEQ ID NO: 315)
aaagguuaaaaaaugguaaa       (SEQ ID NO: 316)
aaauuguaaaaaaugguaaa       (SEQ ID NO: 317)
aaauugcaaaaaaugguaaa       (SEQ ID NO: 318)
aaaugcuaaaaaaugguaaa       (SEQ ID NO: 319)
aaaugauaaaaaaugguaaa       (SEQ ID NO: 320)
aaagguaaaaaaugguaaa        (SEQ ID NO: 321)
aaauggcaaaaaaugguaaa       (SEQ ID NO: 322)
aaaugguaaaaaaugguaaa       (SEQ ID NO: 323)
```

-continued aaaguugaaaaaaugguaaa (SEQ ID NO: 324)

aaaucguaaaaaaugguaaa (SEQ ID NO: 325)

aaagguuaaaaaaguugaaa (SEQ ID NO: 326)

aaauuguaaaaaaguugaaa (SEQ ID NO: 327)

aaauugcaaaaaaguugaaa (SEQ ID NO: 328)

aaaugcuaaaaaaguugaaa (SEQ ID NO: 329)

aaaugauaaaaaaguugaaa (SEQ ID NO: 330)

aaagguaaaaaaaguugaaa (SEQ ID NO: 331)

aaauggcaaaaaaguugaaa (SEQ ID NO: 332)

aaaugguaaaaaaguugaaa (SEQ ID NO: 333)

aaaguugaaaaaaguugaaa (SEQ ID NO: 334)

aaaucguaaaaaaguugaaa (SEQ ID NO: 335)

aaagguuaaaaaaucguaaa (SEQ ID NO: 336)

aaauuguaaaaaaucguaaa (SEQ ID NO: 337)

aaauugcaaaaaaucguaaa (SEQ ID NO: 338)

aaaugcuaaaaaaucguaaa (SEQ ID NO: 339)

aaaugauaaaaaaucguaaa (SEQ ID NO: 340)

aaagguaaaaaaaucguaaa (SEQ ID NO: 341)

aaauggcaaaaaaucguaaa (SEQ ID NO: 342)

aaaugguaaaaaaucguaaa (SEQ ID NO: 343)

aaaguugaaaaaaucguaaa (SEQ ID NO: 344)

aaaucguaaaaaaucguaaa (SEQ ID NO: 345)

aaaguucaaaaaagguuaaa (SEQ ID NO: 346)

aaagucaaaaaaagguuaaa (SEQ ID NO: 347)

aaagcucaaaaaagguuaaa (SEQ ID NO: 348)

aaaguugaaaaaagguuaaa (SEQ ID NO: 349)

aaaguuuaaaaaagguuaaa (SEQ ID NO: 350)

aaagguuaaaaaagguuaaa (SEQ ID NO: 351)

aaaguguaaaaaagguuaaa (SEQ ID NO: 352)

aaaggucaaaaaagguuaaa (SEQ ID NO: 353)

aaagucuaaaaaagguuaaa (SEQ ID NO: 354)

aaaguccaaaaaagguuaaa (SEQ ID NO: 355)

aaaguucaaaaaauuguaaa (SEQ ID NO: 356)

aaagucaaaaaaauuguaaa (SEQ ID NO: 357)

aaagcucaaaaaauuguaaa (SEQ ID NO: 358)

aaaguugaaaaaauuguaaa (SEQ ID NO: 359)

aaaguuuaaaaaauuguaaa (SEQ ID NO: 360)

aaagguuaaaaaauuguaaa (SEQ ID NO: 361)

aaaguguaaaaaauuguaaa (SEQ ID NO: 362)

aaaggucaaaaaauuguaaa (SEQ ID NO: 363)

aaagucuaaaaaauuguaaa (SEQ ID NO: 364)

aaaguccaaaaaauuguaaa (SEQ ID NO: 365)

aaaguucaaaaaauugcaaa (SEQ ID NO: 366)

aaagucaaaaaaauugcaaa (SEQ ID NO: 367)

aaagcucaaaaaauugcaaa (SEQ ID NO: 368)

aaaguugaaaaaauugcaaa (SEQ ID NO: 369)

aaaguuuaaaaaauugcaaa (SEQ ID NO: 370)

aaagguuaaaaaauugcaaa (SEQ ID NO: 371)

aaaguguaaaaaauugcaaa (SEQ ID NO: 372)

aaaggucaaaaaauugcaaa (SEQ ID NO: 373)

aaagucuaaaaaauugcaaa (SEQ ID NO: 374)

aaaguccaaaaaauugcaaa (SEQ ID NO: 375)

aaaguucaaaaaaugcuaaa (SEQ ID NO: 376)

aaagucaaaaaaaugcuaaa (SEQ ID NO: 377)

aaagcucaaaaaaugcuaaa (SEQ ID NO: 378)

aaaguugaaaaaaugcuaaa (SEQ ID NO: 379)

aaaguuuaaaaaaugcuaaa (SEQ ID NO: 380)

aaagguuaaaaaaugcuaaa (SEQ ID NO: 381)

aaaguguaaaaaaugcuaaa (SEQ ID NO: 382)

aaaggucaaaaaaugcuaaa (SEQ ID NO: 383)

aaagucuaaaaaaugcuaaa (SEQ ID NO: 384)

aaaguccaaaaaaugcuaaa (SEQ ID NO: 385)

aaaguucaaaaaaugauaaa (SEQ ID NO: 386)

aaagucaaaaaaaugauaaa (SEQ ID NO: 387)

aaagcucaaaaaaugauaaa (SEQ ID NO: 388)

aaaguugaaaaaaugauaaa (SEQ ID NO: 389)

aaaguuuaaaaaaugauaaa (SEQ ID NO: 390)

aaagguuaaaaaaugauaaa (SEQ ID NO: 391)

aaaguguaaaaaaugauaaa (SEQ ID NO: 392)

aaaggucaaaaaaugauaaa (SEQ ID NO: 393)

aaagucuaaaaaaugauaaa (SEQ ID NO: 394)

aaaguccaaaaaaugauaaa (SEQ ID NO: 395)

aaaguucaaaaaaagguaaaa (SEQ ID NO: 396)

aaagucaaaaaaaagguaaa (SEQ ID NO: 397)

aaagcucaaaaaaagguaaa (SEQ ID NO: 398)

aaaguugaaaaaaagguaaa (SEQ ID NO: 399)

aaaguuuaaaaaaagguaaa (SEQ ID NO: 400)

aaagguuaaaaaaagguaaa (SEQ ID NO: 401)

aaaguguaaaaaaagguaaa (SEQ ID NO: 402)

aaaggucaaaaaaagguaaa (SEQ ID NO: 403)

```
aaagucuaaaaaagguaaaa
                          (SEQ ID NO: 404)
aaaguccaaaaaagguaaaa
                          (SEQ ID NO: 405)
aaaguucaaaaaauggcaaa
                          (SEQ ID NO: 406)
aaagucaaaaaauggcaaa
                          (SEQ ID NO: 407)
aaagcucaaaaaauggcaaa
                          (SEQ ID NO: 408)
aaaguugaaaaaauggcaaa
                          (SEQ ID NO: 409)
aaaguuuaaaaaauggcaaa
                          (SEQ ID NO: 410)
aaagguuaaaaaauggcaaa
                          (SEQ ID NO: 411)
aaaguguaaaaaauggcaaa
                          (SEQ ID NO: 412)
aaaggucaaaaaauggcaaa
                          (SEQ ID NO: 413)
aaagucuaaaaaauggcaaa
                          (SEQ ID NO: 414)
aaaguccaaaaaauggcaaa
                          (SEQ ID NO: 415)
aaaguucaaaaaaugguaaa
                          (SEQ ID NO: 416)
aaagucaaaaaaugguaaa
                          (SEQ ID NO: 417)
aaagcucaaaaaaugguaaa
                          (SEQ ID NO: 418)
aaaguugaaaaaaugguaaa
                          (SEQ ID NO: 419)
aaaguuuaaaaaaugguaaa
                          (SEQ ID NO: 420)
aaagguuaaaaaaugguaaa
                          (SEQ ID NO: 421)
aaaguguaaaaaaugguaaa
                          (SEQ ID NO: 422)
aaaggucaaaaaaugguaaa
                          (SEQ ID NO: 423)
aaagucuaaaaaaugguaaa
                          (SEQ ID NO: 424)
aaaguccaaaaaaugguaaa
                          (SEQ ID NO: 425)
aaaguucaaaaaaguugaaa
                          (SEQ ID NO: 426)
aaagucaaaaaaguugaaa
                          (SEQ ID NO: 427)
aaagcucaaaaaaguugaaa
                          (SEQ ID NO: 428)
aaaguugaaaaaaguugaaa
                          (SEQ ID NO: 429)
aaaguuuaaaaaaguugaaa
                          (SEQ ID NO: 430)
aaagguuaaaaaaguugaaa
                          (SEQ ID NO: 431)
aaaguguaaaaaaguugaaa
                          (SEQ ID NO: 432)
aaaggucaaaaaaguugaaa
                          (SEQ ID NO: 433)
aaagucuaaaaaaguugaaa
                          (SEQ ID NO: 434)
aaaguccaaaaaaguugaaa
                          (SEQ ID NO: 435)
aaaguucaaaaaaucguaaa
                          (SEQ ID NO: 436)
aaagucaaaaaaucguaaa
                          (SEQ ID NO: 437)
aaagcucaaaaaaucguaaa
                          (SEQ ID NO: 438)
aaaguugaaaaaaucguaaa
                          (SEQ ID NO: 439)
aaaguuuaaaaaaucguaaa
                          (SEQ ID NO: 440)
aaagguuaaaaaaucguaaa
                          (SEQ ID NO: 441)
aaaguguaaaaaaucguaaa
                          (SEQ ID NO: 442)
aaaggucaaaaaaucguaaa
                          (SEQ ID NO: 443)
aaagucuaaaaaaucguaaa
                          (SEQ ID NO: 444)
aaaguccaaaaaaucguaaa
                          (SEQ ID NO: 445)
```

In one embodiment, immunostimulatory RNA oligonucleotide of the invention does not have gene silencing activity for any known mammalian gene.

The present invention provides a single-stranded RNA oligonucleotide having IFN-α-inducing activity and low IL-12-inducing activity, comprising at least one, preferably at least two, more preferably at least three, even more preferably at least four, of the 4-nucleotide (4-mer) motifs selected from the group consisting of:

GCUC, GUCA, GUUC, GGUC, GUCC, GUCU, GUUU, CGUC, GCUU, GUGU, wherein the nucleotide sequences of the motifs are 5'→3', wherein the oligonucleotide has an IFN-α score of at least $1.4909 \times n + 22.014$ and an IL-12 score of at most $2.4194 \times n - 31.914$, wherein the IFN-α score is assigned according to the "addition method" described in the co-pending application and the IL-12 score is assigned according to the method described above;

or wherein the oligonucleotide has an IFN-α score of at least 0.58 and an IL-12 score of at most $2.4194 \times n - 31.914$, wherein the IFN-α score is assigned according to the "simplified method" described in the co-pending application and the IL-12 score is assigned according to the method described above;

wherein the oligonucleotide is between 6 and 64, preferably between 12 and 50, more preferably between 14 and 40, even more preferably between 16 and 36, and most preferably between 18 and 30 nucleotides in length.

The present application also provides a single-stranded RNA oligonucleotide having IL-12-inducing activity and low IFN-α-inducing activity, comprising at least one, preferably at least two, more preferably at least three, even more preferably at least four, of the 4-nucleotide (4-mer) motifs selected from the group consisting of:

UCGU, GAUA, UGGC, UGCU, UGGU, UGCC, UUGC, UGAC, UAAU, UUAU, wherein the nucleotide sequences of the motifs are 5'→3', wherein the oligonucleotide has an IL-12 score of at least $8.4064 \times n + 66.958$ and an IFN-α score of at most $0.5439 \times n - 8.0234$, wherein the IFN-α score is assigned according to the "addition method" described in the co-pending application and the IL-12 score is assigned according to the method described above;

or wherein the oligonucleotide has an IL-12 score of at least $8.4064 \times n + 66.958$ and an IFN-α score of at most 0.11, wherein the IFN-α score is assigned according to the "simplified method" described in the co-pending application and the IL-12 score is assigned according to the method described above;

wherein the oligonucleotide is between 6 and 64, preferably between 12 and 50, more preferably between 14 and 40, even more preferably between 16 and 36, and most preferably between 18 and 30 nucleotides in length.

The present application further provides a single-stranded RNA oligonucleotide having both IL-12-inducing activity and IFN-α-inducing activity, comprising at least one, preferably at least two, more preferably at least three, even more preferably at least four, of the 4-nucleotide (4-mer) motifs selected from the group consisting of:

GUUG, GGUU, UUGU, GGUA, CUGU, UGUC, UGUA, UGUU, UGUG, UAGU, wherein the nucleotide sequences of the motifs are 5'→3', wherein the oligonucleotide has an IL-12 score of at least $8.4064 \times n + 66.958$ and an IFN-α score of at least $1.4909 \times n + 22.014$, wherein the IFN-α score is assigned according to the "addition method" described in the co-pending application and the IL-12 score is assigned according to the method described above;

or wherein the oligonucleotide has an IL-12 score of at least $8.4064 \times n + 66.958$ and an IFN-α score of at least 0.58, wherein the IFN-α score is assigned according to the "simplified method" described in the co-pending application and the IL-12 score is assigned according to the method described above;

wherein the oligonucleotide is between 6 and 64, preferably between 12 and 50, more preferably between 14 and 40, even more preferably between 16 and 36, and most preferably between 18 and 30 nucleotides in length.

Briefly, the "addition method" for assigning the IFN-α score of an oligonucleotide and thereby predicting its immunostimulatory activity comprises the steps of:

(a) identifying all possible 3-nucleotide (3mer) motifs contained in the oligonucleotide;

(b) assigning an IFN-α point score for each individual 3mer motif:

(i) for a 3mer motif which appears in Table A, assign an IFN-α point score according to Table A;

(ii) for a 3mer motif which does not appear in Table A, assign an IFN-α point score of 0;

(c) assigning the sum of the IFN-α point scores of individual 3mer motifs as the IFN-α score of the oligonucleotide; and (d) assigning to the oligonucleotide a high immunostimulatory activity if the IFN-α score is at least 23, an intermediate immunostimulatory activity if the IFN-α score is between −4 and 23, and a low immunostimulatory activity if the IFN-α score is at most −4, when n=6;

assigning to the oligonucleotide a high immunostimulatory activity if the IFN-α score is at least 26, an intermediate immunostimulatory activity if the IFN-α score is between −4 and 26, and a low immunostimulatory activity if the IFN-α score is at most −4, when n=7;

assigning to the oligonucleotide a high immunostimulatory activity if the IFN-α score is at least 28, an intermediate immunostimulatory activity if the IFN-α score is between −5 and 28, and a low immunostimulatory activity if the IFN-α score is at most −5, when n=8;

assigning to the oligonucleotide a high immunostimulatory activity if the IFN-α score is at least 30, an intermediate immunostimulatory activity if the IFN-α score is between −5 and 30, and a low immunostimulatory activity if the IFN-α score is at most −5, when n=9;

assigning to the oligonucleotide a high immunostimulatory activity if the IFN-α score is at least $1.4909 \times n + 22.014$, an intermediate immunostimulatory activity if the IFN-α score is between $0.005 \times n^2 - 0.2671 \times n - 3.5531$ and $1.4909 \times n + 22.014$, and a low immunostimulatory activity if the IFN-α score is at most $0.005 \times n^2 - 0.2671 \times n - 3.5531$, when n is greater than 9, wherein n is the length of the oligonucleotide.

TABLE A

| 3mer motif (5'→3') | IFN-α point score |
| --- | --- |
| ACA | −2 |
| ACC | −2 |
| AGA | −2 |
| AAC | −1 |
| AUA | −1 |
| UGG | +1 |
| GUA | +3 |
| GUG | +3 |
| GGU | +4 |
| UCA | +4 |
| UUC | +4 |
| UUU | +5 |
| AGU | +6 |
| UUG | +6 |
| GUC | +8 |
| UGU | +8 |
| GUU | +9 |

The "simplified method" for assigning the IFN-α score of an oligonucleotide and thereby predicting its immunostimulatory activity comprises the steps of:

(a) identifying all possible 3-nucleotide (3mer) motifs contained in the oligonucleotide;

(b) assigning an IFN-α point score for each individual 3mer motif according to Table B;

(c) assigning the highest individual IFN-α point score as the IFN-α score of the oligonucleotide; and (d) assigning to the oligonucleotide a high immunostimulatory activity if the IFN-α score is at least 0.58, an intermediate immunostimulatory activity if the IFN-α score is between 0.11 and 0.58, and a low immunostimulatory activity if the IFN-α score is at most 0.11.

TABLE B

| Motif | Occurrences | Mean (IFN-α point score) | Sem | p-value |
| --- | --- | --- | --- | --- |
| AAA | 2192 | 0.00 | 0.01 | 0.389 |
| AAC | 67 | −0.14 | 0.02 | **0.001 |
| AAG | 67 | 0.11 | 0.06 | **0.009 |
| AAU | 67 | 0.01 | 0.03 | 0.841 |
| ACA | 31 | −0.17 | 0.02 | **0.007 |
| ACC | 19 | −0.19 | 0.01 | *0.017 |
| ACG | 19 | −0.12 | 0.05 | 0.128 |
| ACU | 19 | −0.07 | 0.05 | 0.407 |
| AGA | 31 | −0.14 | 0.02 | *0.021 |
| AGC | 19 | −0.05 | 0.09 | 0.508 |
| AGG | 19 | −0.01 | 0.09 | 0.877 |
| AGU | 19 | 0.59 | 0.10 | **<0.001 |
| AUA | 31 | −0.10 | 0.02 | 0.118 |
| AUC | 19 | −0.11 | 0.03 | 0.176 |
| AUG | 19 | 0.08 | 0.07 | 0.318 |
| AUU | 19 | 0.09 | 0.06 | 0.253 |
| CAA | 67 | 0.00 | 0.05 | 0.913 |
| CAC | 7 | −0.21 | 0.01 | 0.11 |
| CAG | 7 | −0.13 | 0.06 | 0.313 |
| CAU | 7 | −0.19 | 0.01 | 0.143 |
| CCA | 19 | −0.14 | 0.05 | 0.077 |
| CCC | 7 | −0.21 | 0.01 | 0.102 |
| CCG | 7 | −0.21 | 0.01 | 0.11 |
| CCU | 7 | −0.15 | 0.03 | 0.252 |
| CGA | 19 | −0.14 | 0.04 | 0.082 |
| CGC | 7 | −0.19 | 0.02 | 0.155 |
| CGG | 7 | −0.18 | 0.03 | 0.172 |

TABLE B-continued

| Motif | Occurrences | Mean (IFN-α point score) | Sem | p-value |
|---|---|---|---|---|
| CGU | 7 | 0.05 | 0.11 | 0.678 |
| CUA | 19 | −0.09 | 0.05 | 0.251 |
| CUC | 7 | 0.16 | 0.19 | 0.229 |
| CUG | 7 | 0.00 | 0.12 | 0.979 |
| CUU | 7 | 0.08 | 0.12 | 0.529 |
| GAA | 67 | −0.08 | 0.03 | *0.044 |
| GAC | 7 | −0.19 | 0.02 | 0.153 |
| GAG | 7 | −0.13 | 0.06 | 0.306 |
| GAU | 7 | −0.11 | 0.01 | 0.385 |
| GCA | 19 | −0.12 | 0.04 | 0.114 |
| GCC | 7 | −0.19 | 0.03 | 0.149 |
| GCG | 7 | −0.17 | 0.03 | 0.184 |
| GCU | 7 | 0.22 | 0.21 | 0.094 |
| GGA | 19 | −0.13 | 0.04 | 0.111 |
| GGC | 7 | −0.17 | 0.04 | 0.194 |
| GGG | 7 | −0.22 | 0.00 | 0.095 |
| GGU | 7 | 0.40 | 0.18 | **0.002 |
| GUA | 19 | 0.27 | 0.08 | **<0.001 |
| GUC | 7 | 0.82 | 0.10 | **<0.001 |
| GUG | 7 | 0.32 | 0.13 | *0.014 |
| GUU | 7 | 0.87 | 0.18 | **<0.001 |
| UAA | 67 | 0.06 | 0.04 | 0.135 |
| UAC | 7 | −0.06 | 0.08 | 0.647 |
| UAG | 7 | 0.01 | 0.08 | 0.94 |
| UAU | 7 | −0.03 | 0.07 | 0.793 |
| UCA | 19 | 0.35 | 0.12 | **<0.001 |
| UCC | 7 | −0.03 | 0.14 | 0.794 |
| UCG | 7 | 0.02 | 0.09 | 0.848 |
| UCU | 7 | 0.10 | 0.13 | 0.421 |
| UGA | 19 | 0.04 | 0.08 | 0.611 |
| UGC | 7 | 0.01 | 0.07 | 0.91 |
| UGG | 7 | 0.10 | 0.09 | 0.448 |
| UGU | 7 | 0.69 | 0.06 | **<0.001 |
| UUA | 19 | 0.17 | 0.10 | *0.036 |
| UUC | 7 | 0.37 | 0.18 | **0.005 |
| UUG | 7 | 0.38 | 0.18 | **0.004 |
| UUU | 7 | 0.32 | 0.17 | *0.013 |

The immunostimulatory RNA oligonucleotide of the invention may be covalently linked to one or more lipophilic groups which enhance the stability and the activity and facilitate the delivery of the RNA oligonucleotides.

As used herein, the term "lipophilic" or "lipophilic group" broadly refers to any compound or chemical moiety having an affinity for lipids. Lipophilic groups encompass compounds of many different types, including those having aromatic, aliphatic or alicyclic characteristics, and combinations thereof.

In specific embodiments, the lipophilic group is an aliphatic, alicyclic, or polyalicyclic substance, such as a steroid (e.g., sterol) or a branched aliphatic hydrocarbon. The lipophilic group generally comprises a hydrocarbon chain, which may be cyclic or acyclic. The hydrocarbon chain may comprise various substituents and/or at least one heteroatom, such as an oxygen atom. Such lipophilic aliphatic moieties include, without limitation, saturated or unsataratated fatty acids, waxes (e.g., monohydric alcohol esters of fatty acids and fatty diamides), terpenes (e.g., the $C_{10}$ terpenes, $C_{15}$ sesquiterpenes, $C_{20}$ diterpenes, $C_{30}$ triterpenes, and $C_{40}$ tetraterpenes), and other polyalicyclic hydrocarbons.

The lipophilic group may be attached by any method known in the art, including via a functional grouping present in or introduced into the RNA oligonucleotide, such as a hydroxy group (e.g., —CO—$CH_2$—OH). Conjugation of the RNA oligonucleotide and the lipophilic group may occur, for example, through formation of an ether or a carboxylic or carbamoyl ester linkage between the hydroxy and an alkyl group R—, an alkanoyl group RCO— or a substituted carbamoyl group KNHCO—. The alkyl group R may be cyclic (e.g., cyclohexyl) or acyclic (e.g., straight-chained or branched; and saturated or unsaturated). Alkyl group R may be a butyl, pentyl, hexyl, heptyl, octyl, nonyl, decyl, undecyl, dodecyl, tridecyl, tetradecyl, pentadecyl, hexadecyl, heptadecyl or octadecyl group, or the like. Preferably, the lipophilic group is conjugated to the 5'-hydroxyl group of the terminal nucleotide. In a preferred embodiment, the liphophilic group is 12-hydroxydodeconoic acid bisdecylamide.

In another embodiment, the lipophilic group is a steroid, such as sterol. Steroids are polycyclic compounds containing a perhydro-1,2-cyclopentanophenanthrene ring system. Steroids include, without limitation, bile acids (e.g., cholic acid, deoxycholic acid and dehydrocholic acid), cortisone, digoxigenin, testosterone, cholesterol and cationic steroids, such as cortisone.

In a preferred embodiment, the lipophilic group is cholesterol or a derivative thereof. A "cholesterol derivative" refers to a compound derived from cholesterol, for example by substitution, addition or removal of substituents. The steroid may be attached to the RNA oligonucleotide by any method known in the art. In a preferred embodiment, the liphophilic group is cholesteryl (6-hydroxyhexyl) carbamate.

In another embodiment, the lipophilic group is an aromatic moiety. In this context, the term "aromatic" refers broadly to mono- and polyaromatic hydrocarbons. Aromatic groups include, without limitation, $C_6$-$C_{14}$ aryl moieties comprising one to three aromatic rings, which may be optionally substituted; "aralkyl" or "arylalkyl" groups comprising an aryl group covalently linked to an alkyl group, either of which may independently be optionally substituted or unsubstituted; and "heteroaryl" groups. As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, between one and about three heteroatoms selected from the group consisting of nitrogen (N), oxygen (O), and sulfur (S).

As used herein, a "substituted" alkyl, cycloalkyl, aryl, heteroaryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The lipophilic group can be covalently linked directly or indirectly via a linker to the RNA oligonucleotide. The covalent linkage may or may not comprise a phosphodiester group. And the linker may be of various lengths. The preferred lengths of the linker are known to those skilled in the art and may be determined experimentally.

In one embodiment, the lipophilic group is covalently linked to the 5' end of the RNA oligonucleotide.

In addition, the immunostimulatory oligonucleotide of the invention may be coupled to a solid support. By "coupled" it is meant that the oligonucleotide is covalently or non-covalently, directly or indirectly, linked to the solid support. Suitable solid supports include, but are not limited to, silicon wafers, synthetic polymer support such as polystyrene, polypropylene, polyglycidylmethacrylate, substituted polystyrene (e.g., aminated or carboxylated polystyrene, polyacrlamides, polyamides, polyvinylchlorides, etc.), glass, agarose, nitrocellulose, nylon and gelatin nanoparticles. Solid support may enhance the stability and the activity of the oligonucleotide, especially short oligonucleotides less than 16 nucleotides in length.

Immunostimulatory RNA Oligonucleotide Conjugates

The present invention also provides immunomodulatory RNA oligonucleotide conjugates, comprising an immunomodulatory RNA oligonucleotide and an antigen conjugated to the oligonucleotide. In some embodiments, the antigen is conjugated to the oligonucleotide at a position other than its 3' end. In some embodiments, the antigen produces a vaccine effect.

The antigen is preferably selected from the group consisting of disease/disorder-related antigens. The disorder may be a cancer, a dermatological disorder, an immune disorder, a metabolic disorder, a neurological disorder, an ocular disease, an infection, or other hereditary and non-hereditary disorders. The antigen may be a protein, a polypeptide, a peptide, a carbohydrate, or a combination thereof.

The immunostimulatory RNA oligonucleotide may be covalently linked to the antigen, or it is otherwise operatively associated with the antigen. As used herein, the term "operatively associated with" refers to any association that maintains the activity of both the oligonucleotide and the antigen. Non-limiting examples of such operative associations include being part of the same liposome or other such delivery vehicle or reagent. In embodiments wherein the oligonucleotide agent is covalently linked to the antigen, such covalent linkage preferably is at any position on the oligonucleotide that does not interfere with the immunostimulatory activity of the oligonucleotide.

Antisense RNA Oligonucleotide with High or Low Immunostimulatory Activity

The present invention provides an antisense RNA oligonucleotide with gene silencing activity.

In one embodiment, the antisense RNA oligonucleotide has both gene silencing activity and immunostimulatory activity, wherein the oligonucleotide has an IL-12 score of at least $8.4064 \times n$ 66.958, wherein the IL-12 score is assigned according to the method describe above, wherein n is the length of the oligonucleotide and n is between 14 and 50, and wherein the oligonucleotide is not 5'-GCACCACUAGUUG-GUUGUC-3' (SEQ ID NO: 198) ([18]), 5'-UGCUAUUG-GUGAUUGCCUC-3' (SEQ ID NO: 199) ([18]), 5'-GUU-GUAGUUGUACUCCAGC-3' (SEQ ID NO: 200) ([18]).

In another embodiment, the antisense RNA oligonucleotide has gene silencing activity and low/minimal immunostimulatory activity, wherein the oligonucleotide has an IL-12 score of at most $1.9763 \times n - 30.643$, wherein the IL-12 score is assigned according to the method describe above, wherein n is the length of the oligonucleotide and n is between 14 and 50, and wherein the oligonucleotide is not 5'-UACCUAAC-CGGACAUAAUC-3' (SEQ ID NO: 214) ([17]), 5'-UAAAC-CUUCGAUUCCGACC-3' (SEQ ID NO: 215) ([17]), 5'-UAGCGACUAAACGCAUCAA-3' (SEQ ID NO: 216) ([17]), 5'-AUACGCUCAGACAAAGCUG-3' (SEQ ID NO: 217) ([17]), 5'-AUACGCUCACACAAAGCUG-3' (SEQ ID NO: 218) ([17]), 5'-CUAAUACAGGCCAAUACAU-3' (SEQ ID NO: 219) ([17]), 5'-UAGCGACUAAACACAU-CAA-3' (SEQ ID NO: 220) ([17]), 5'-UAAACCU-UUAGCUCCGACC-3' (SEQ ID NO: 221) ([17]), 5'-AUAC-CAGGCUCCAAAGCUG-3' (SEQ ID NO: 222) ([17]), 5'-UAGCGACUAAGCGCAUCAA-3' (SEQ ID NO: 223) ([17]), 5'-AUACGCUCAGCCAAAGCUG-3' (SEQ ID NO: 224) ([17]), 5'-AAGGCAGCACGACUUCUUC-3' (SEQ ID NO: 225) ([18]).

The antisense RNA oligonucleotide of the invention may be covalently linked to one or more lipophilic groups which enhance the stability and the activity and facilitate the delivery of the RNA oligonucleotides.

Pharmaceutical Compositions

The present invention provides pharmaceutical compositions comprising one or more of the ssRNA oligonucleotides of the invention and a pharmaceutically acceptable carrier. The more than one RNA oligonucleotides may have the same, similar, or different functionalities including, but are not limited to immunostimulatory activity and gene silencing activity.

For example, an ssRNA oligonucleotide having immunostimulatory activity but lacking gene silencing activity may be combined with an ssRNA oligonucleotide having gene silencing activity and low immunostimulatory activity in a pharmaceutical composition to achieve both immune activation and gene silencing. Such a combination composition may be useful for treating disorders such as cancers and viral infections. Such a combination composition may be necessary when the two activities cannot be optimized on a single RNA oligonucleotide.

In one embodiment, the pharmaceutical composition further comprises a RNA complexation agent. In a preferred embodiment, the complexation agent is a polycationic peptide, preferably poly-L-arginine (poly-L-Arg). In a preferred embodiment, the polycationic peptide, in particular, poly-L-Arg, is at least 24 amino acids in length (SEQ ID NO: 447). The polycationic peptide, in particular, poly-L Arg, may be a heterogeneous mixture of peptides of different lengths.

The pharmaceutical composition of the invention may further comprises another agent such as an agent that stabilizes the RNA oligonucleotide(s), e.g., a protein that complexes with the oligonucleotide agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

The pharmaceutical composition of the present invention may further comprise one or more additional pharmaceutically active (or therapeutic) agents which are selected from the group consisting of agents that are used for the treatment of cancer, dermatological disorders, immune disorders, metabolic disorders, neurological disorders, ocular diseases, infections, and other hereditary and non-hereditary disorders in a mammal.

In certain embodiments, the additional pharmaceutically active agent is selected from the group consisting of immunostimulatory RNA oligonucleotides, immunostimulatory DNA oligonucleotides, cytokines, chemokines, growth factors, antibiotics, anti-angiogenic factors, chemotherapeutic agents, anti-viral agents, anti-fungal agents, anti-parasitic agents, and antibodies. In one embodiment, the additional pharmaceutically active agent is natural or recombinant IL-12, or a CpG-containing RNA oligonucleotide capable inducing IL-12 (see e.g., Sugiyama et al. 2005, *J Immunol* 174:2273-2279). In another embodiment, the additional pharmaceutically active agent is natural or recombinant IFN-α polypeptide, an immunostimulatory RNA oligonucleotide capable of inducing IFN-α (see e.g., our co-pending application), or a CpG-containing or non-CpG-containing DNA oligonucleotide capable of inducing IFN-α (see e.g., WO 01/22990, WO 03/101375). In yet another embodiment, the additional pharmaceutically active agent is natural or recombinant IL-2. In another embodiment, the additional pharmaceutically active agent is an anti-angiogenic factor such as vasostatin or an anti-VEGF antibody. In certain embodiments, the additional pharmaceutically active agent is a cancer-specific agent such as Herceptin, Rituxan, Gleevec, Iressa.

A formulated oligonucleotide composition can assume a variety of states. In some examples, the composition is at least partially crystalline, uniformly crystalline, and/or anhydrous (e.g., less than 80, 50, 30, 20, or 10% water). In another example, the oligonucleotide agent is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the oligonucleotide composition is formulated in a manner that is compatible with the intended method of administration.

The pharmaceutical compositions encompassed by the invention may be administered by any means known in the art including, but not limited to, oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

For oral administration, the oligonucleotide agent useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of oligonucleotide agent in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce oligonucleotide agent into cell cultures, surprisingly these methods and agents are not necessary for uptake of oligonucleotide agent in vivo. The oligonucleotide agent of the present invention are particularly advantageous in that they do not require the use of an auxiliary agent to mediate uptake of the oligonucleotide agent into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions can also include encapsulated formulations to protect the oligonucleotide agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075.

In general, a suitable dose of a RNA oligonucleotide will be in the range of 0.001 to 500 milligrams per kilogram body weight of the recipient per day (e.g., about 1 microgram per kilogram to about 500 milligrams per kilogram, about 100 micrograms per kilogram to about 100 milligrams per kilogram, about 1 milligrams per kilogram to about 75 milligrams per kilogram, about 10 micrograms per kilogram to about 50 milligrams per kilogram, or about 1 microgram per kilogram to about 50 micrograms per kilogram). The pharmaceutical composition may be administered once per day, or the oligonucleotide agent may be administered as two, three, four, five, six or more sub-doses at appropriate intervals throughout the day. In that case, the oligonucleotide agent contained in each sub-dose must be correspondingly smaller in order to achieve the total daily dosage. The dosage unit can also be compounded for delivery over several days, e.g., using a conventional sustained release formulation which provides sustained release of the oligonucleotide agent over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease/disorder, previous treatments, the general health and/or age of the subject, and other diseases/disorders present. Moreover, treatment of a subject with a therapeutically effective amount of a composition can include a single treatment or a series of treatments. Estimates of effective dosages and in vivo half-lives for the individual RNA oligonucleotide agent encompassed by the invention can be made using conventional methodologies or on the basis of in vivo testing using an appropriate animal model, as described elsewhere herein.

Toxicity and therapeutic efficacy of the RNA oligonucleotide and the pharmaceutical composition of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. oligonucleotide agents that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any oligonucleotide agent used in the method of the invention, the therapeutically effective dose can be estimated initially from cell culture assays. A dose may be formulated in animal models to achieve a circulating plasma concentration range of the oligonucleotide agent or, when appropriate, of the polypeptide product of a target sequence (e.g., achieving a decreased concentration of the polypeptide) that includes the IC50 (i.e., the concentration of the test oligonucleotide agent which achieves a half-maximal inhibition of symptoms) as determined in cell culture. Such information can be used to more accurately determine useful doses in humans. Levels in plasma may be measured, for example, by high performance liquid chromatography.

The administering physician can adjust the amount and timing of the administration of the pharmaceutical composition of the invention on the basis of results observed using standard measures of efficacy known in the art or described herein.

Use of the ssRNA Oligonucleotide for Inducing an Immune Response

The present application provides the use of the immunostimulatory ssRNA oligonucleotide of the invention for the preparation of a pharmaceutical composition for inducing an immune response in a mammal.

Inducing an immune response means initiating or causing an increase in one or more of B-cell activation, T-cell activation, natural killer cell activation, activation of antigen presenting cells (e.g., B cells, dendritic cells, monocytes and macrophages), cytokine production, chemokine production, specific cell surface marker expression, in particular, expression of co-stimulatory molecules. In one aspect, such an immune response involves the production of type IL-12 in cells such as monocytes, macrophages, and myeloid dendritic cells.

Use of the RNA Oligonucleotide for Treating Diseases/Disorders

The present invention provides the use of the immunostimulatory ssRNA oligonucleotide of the invention for the preparation of a pharmaceutical composition for preventing and/or treating a disorder selected from immune disorders, infections, and cancers in a mammal, wherein the induction of an immune response is beneficial to the mammal.

The present invention also provides the use of the antisense RNA oligonucleotide of the invention which has both immunostimulatory activity and gene silencing activity for the preparation of a pharmaceutical composition for preventing and/or treating a disorder selected from infections and cancers in a mammal, wherein the induction of an immune response together with the downregulation of a disorder-related gene are beneficial to the mammal.

The present invention further provides the use of the antisense RNA oligonucleotide of the invention which has gene silencing activity and low/minimal immunostimulatory activity for the preparation of a pharmaceutical composition for preventing and/or treating a disorder in a mammal caused by the expression or overexpression of a disorder-related gene, wherein the induction of an immune disorder it to be avoided. The disorder may be selected from cancer, dermatological disorders, immune disorders, metabolic disorders, neurological disorders, ocular diseases, infections, and other hereditary and non-hereditary disorders.

The immune disorders include, but are not limited to, allergy, autoimmune disorders, inflammatory disorders, and immunodeficiency.

Allergies include, but are not limited to, food allergies and respiratory allergies.

Autoimmune diseases include, but are not limited to, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Inflammatory disorders include, without limitation, airway inflammation which includes, without limitation, asthma.

Immunodeficiencies include, but are not limited to, spontaneous immunodeficiency, acquired immunodeficiency (including AIDS), drug-induced immunodeficiency (such as that induced by immunosuppressants used in transplantation and chemotherapeutic agents used for treating cancer).

In one embodiment, the immune disorders include those caused by pathological Th2 responses.

The infections include, but are not limited to viral infections, bacterial infections, anthrax, parasitic infections, fungal infections and prion infection.

Viral infections include, but are not limited to, infection by hepatitis C, hepatitis B, herpes simplex virus (HSV), HIV-AIDS, measles virus, poliovirus, and smallpox virus. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus 0), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus).

In certain embodiments, the viral infections are selected from chornic hepatitis B, chornic hepatitis C, HIV infection, RSV infection, HSV infection, VSV infection, CMV infection, measles virus infection, and influenza infection.

In certain embodiments, the parasitic infections include, but are not limited to, Lesihmania infection and Toxoplasma infection.

In one embodiment, the bacterial infection is *M. tuberculosis* infection.

Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, cancers are selected from hairy cell leukemia, chronic myelogenous leukemia, cutaneous T-cell leukemia, chronic myeloid leukemia, non-Hodgkin's lymphoma, Burkitt lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, malignant glioma and Kaposi's sarcoma (AIDS-related and non-AIDS-related).

Dermatological disorders include, but are not limited to, psoriasis, acne, rosacea, eczema, molluscum contagious, seborrheic keratosis, actinic keratosis, verruca vulgaris.

Metabolic disorders include, but are not limited to, diabetes and obesity.

Ocular diseases include, but are not limited to, age-related macular degeneration.

Neurological disorders include, but are not limited to, Alzeimer' disease, Huntington's disease, Parkinson's disease, and spinal cord injury.

Hereditary diseases include, but are not limited to, cystic fibrosis.

In one embodiment, the pharmaceutical composition is for administration selected from the group consisting of airway, oral, ocular, parenteral (including intravenous, intradermal, intramuscular, intraperitoneal, and subcutaneous), rectal, vaginal and topical (including buccal and sublingual) administration.

In another embodiment, the pharmaceutical composition is for use in combination with one or more treatments of disorders selected from treatments for cancer, dermatological disorders, immune disorders, metabolic disorders, neurological disorders, ocular diseases, infections, and other hereditary and non-hereditary disorders in a mammal. Such treatments include, but are not limited to, surgery, chemotherapy, radiation therapy, and the administration of pharmaceutically active (or therapeutic) agents such as immunostimulatory RNA oligonucleotides, immunostimulatory DNA oligonucleotides, cytokines, chemokines, growth factors, antibiotics, anti-angiogenic factors, chemotherapeutic agents, antiviral agents, anti-fungal agents, anti-parasitic agents, and antibodies.

In one embodiment, the pharmaceutically active agent is natural or recombinant IL-12, or a CpG-containing RNA oligonucleotide capable inducing IL-12 (see e.g., Sugiyama et al. 2005, *J Immunol* 174:2273-2279). In another embodiment, the pharmaceutically active agent is natural or recombinant IFN-α polypeptide, an immunostimulatory RNA oligonucleotide capable of inducing IFN-α (see e.g., our co-pending application), or a CpG-containing or non-CpG-containing DNA oligonucleotide capable of inducing IFN-α (see e.g., WO 01/22990, WO 03/101375). In yet another embodiment, the pharmaceutically active agent is natural or recombinant IL-2. In another embodiment, the pharmaceutically active agent is an anti-angiogenic factor such as vasostatin or an anti-VEGF antibody. In certain embodiments, the pharmaceutically active agent is a cancer-specific agent such as Herceptin, Rituxan, Gleevec, Iressa.

Mammals include, but are not limited to, rats, mice, cats, dogs, horses, sheep, cattle, cows, pigs, rabbits, non-human primates, and humans. In a preferred embodiment, the mammal is human.

In Vitro Method for Inducing IL-12 Production

The present invention provides an in vitro method of inducing IL-12 production in a mammalian cell, comprising the steps of:
  (a) complexing an immunostimulatory RNA oligonucleotide of the invention with a complexation agent; and
  (b) contacting the cell with the complex prepared in step (a).

The mammalian cell is capable of producing IL-12. In one embodiment, the mammalian cell expresses TLR8. The mammalian cells include, but are not limited to, peripheral blood mononuclear cells (PBMC), myeloid dendritic cells (MDC), B cells, macrophages, monocytes, and cells containing exogenous DNA which directs the expression of TLR7 or TLR8 or both TLR7 or TLR8 such as transfected CHO, HEK293 or COS cells.

In one embodiment of the invention, the complexation agent is a polycationic peptide, preferably poly-L-arginine (poly-L-Arg). In one embodiment, the polycationic peptide, in particular, poly-L-Arg, is at least 24 amino acids in length (SEQ ID NO: 447). The polycationic peptide, in particular, poly-L Arg, may be a heterogeneous mixture of peptides of different lengths.

In a preferred embodiment, the mammal is human.

The present invention is illustrated by the following examples.

EXAMPLES

Example 1

Figure 1:
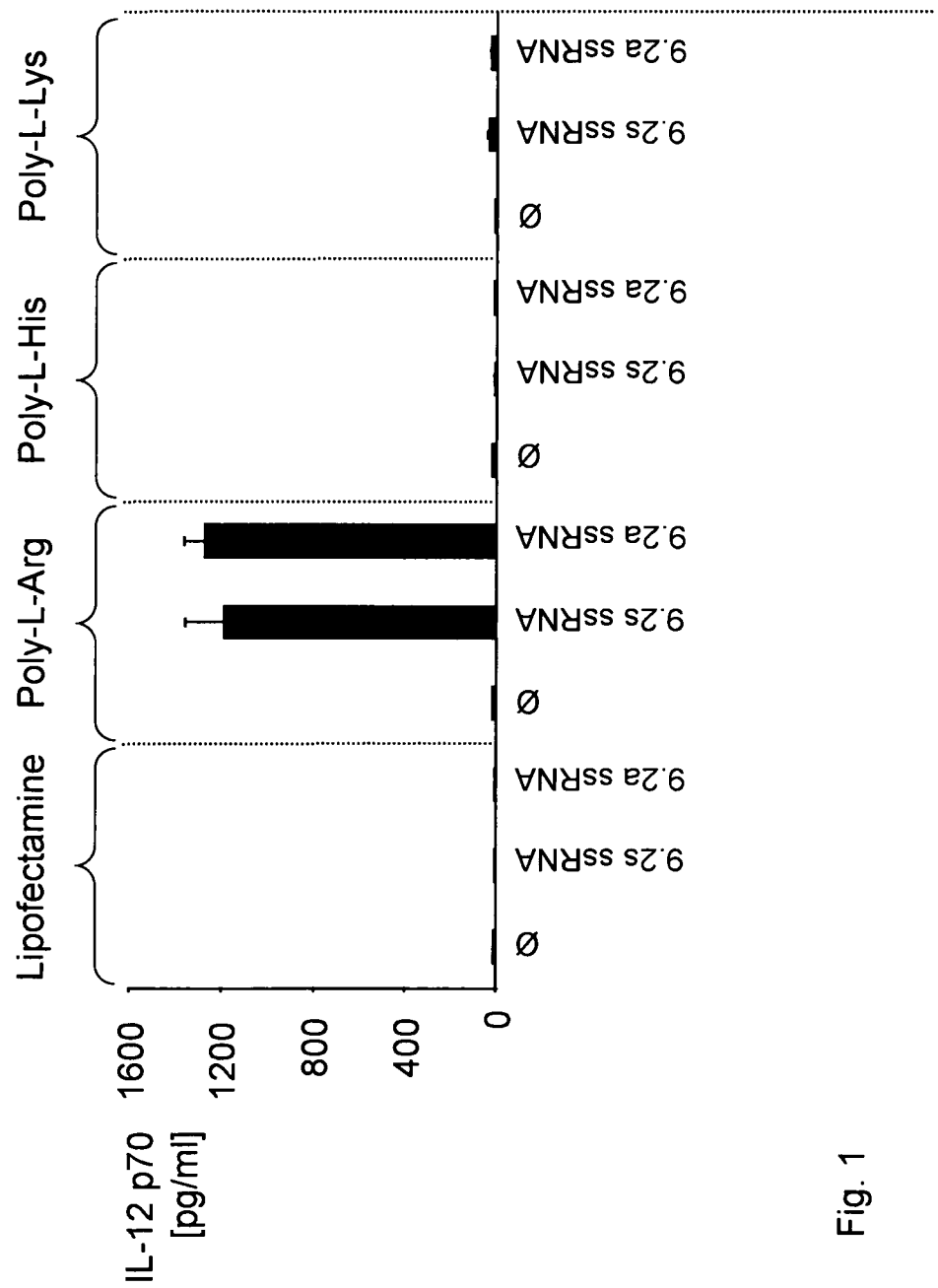
FIG. 1: PBMC of three individual donors were isolated and stimulated with ssRNA-oligonucleotides 9.2sense (5'-AGCUUAACCUGUCCUUCAA-3' (SEQ ID NO: 194)) and 9.2antisense (5'-UUGAAGGACAGGUUAAGCU-3' (SEQ ID NO: 446)) that were complexed with either Lipofectamine, poly-L-arginine, poly-L-histidine or poly-L-lysine in duplicates. 24 hours after stimulation supernatants were harvested and IL-12p70 was assessed by ELISA. Data are presented as mean values ±SEM.

Poly-L-arginine Complexed ssRNA Oligonucleotides are Potent Inductors of IL-12 in PBMC Given the fact that myeloid cells express high levels of TLR8, it is remarkable that so far little has been reported about RNA-mediated activation of cells of the myeloid lineage. We have previously shown that plasmacytoid dendritic cells are highly sensitive to both short double and single stranded RNA molecules, when cationic lipids are employed to complex respective RNA oligonucleotides. Interestingly, when we addressed the activation of cells of the myeloid lineage in the human system via cationic lipid complexed RNA-oligonucleotides, we were unable to document a significant activation. Indeed, when we used cationic lipids to transfect RNA-oligonucleotides, we observed a considerable cytotoxicity, most prominent in the population of myeloid cells (data not shown). This was in marked contrast to the use of the cationic polypetide poly-L-arginine for complexation of RNA-oligonucleotides. Poly-L-arginine complexed single stranded RNA-oligonucleotides were highly active in terms of IL-12 induction within PBMC, whereas no IL-12 was induced when the cationic lipid Lipofectamine 2000 was used to transfect ssRNA-oligonucleotides into PBMC. Other polycationic polypeptides such as poly-L-lysine and poly-L-histidine were not active in terms of IL-12 induction (FIG. 1).

Example 2

Figure 2:
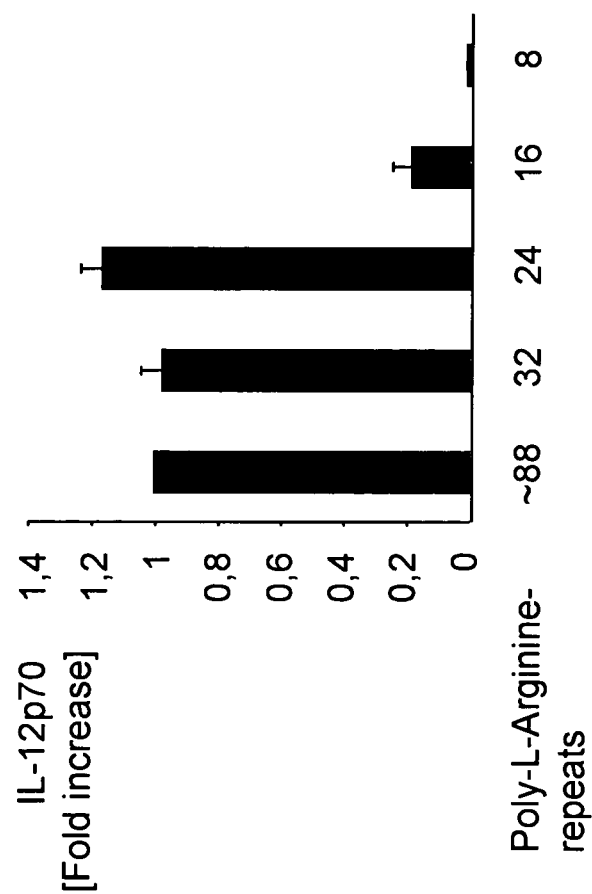
FIG. 2: PBMC of two different healthy donors were isolated and stimulated with poly-L-arginine complexed ssRNA-oligonucleotide 9.2sense (5'-AGCUUAACCUGUC-CUUCAA (SEQ ID NO: 194)) in duplicates. Poly-L-Arginine polymers of different sizes were used as indicated. 24 hours after stimulation supernatants were assessed for IL-12p70 production. Data were normalized to the poly-L-arginine polypetide with an approximate number of 88 amino acids (absolute values were 1390 and 396 pg/ml for donor 1 and donor 2). Data from two different donors were summarized and are presented as mean values ±SEM.

At least 24meric Polypeptides of poly-L-arginine are Required to Achieve Maximal IL-12 Induction in PBMC In our first set of experiments we used poly-L-arginine consisting of an inhomogeneous mixture of polypetides from 5-15 kDa (approx. 44-132 aminoacids). To decipher the minimal length of poly-L-arginine required for IL-12 induction in PBMC, we compared the activity of the ~88 mer poly-L-arginine to defined synthetic 32mer, 24mer, 16mer and 8mer polypetides. As depicted in FIG. 2, at least 24 residues of the cationic amino acid L-arginine were required to elicit a substantial IL-12 response in PBMC. Other polycationic peptides containing poly-L-arginine such as homopolymers derived from the HIV TAT peptide were also able to complex ssRNA oligonucleotides. IL-12 induction in PBMC was also detected, yet to a lesser extent (data not shown). Nevertheless, at least 24meric TAT peptides were needed to induce IL-12 in PBMC.

Example 3

Figure 3:
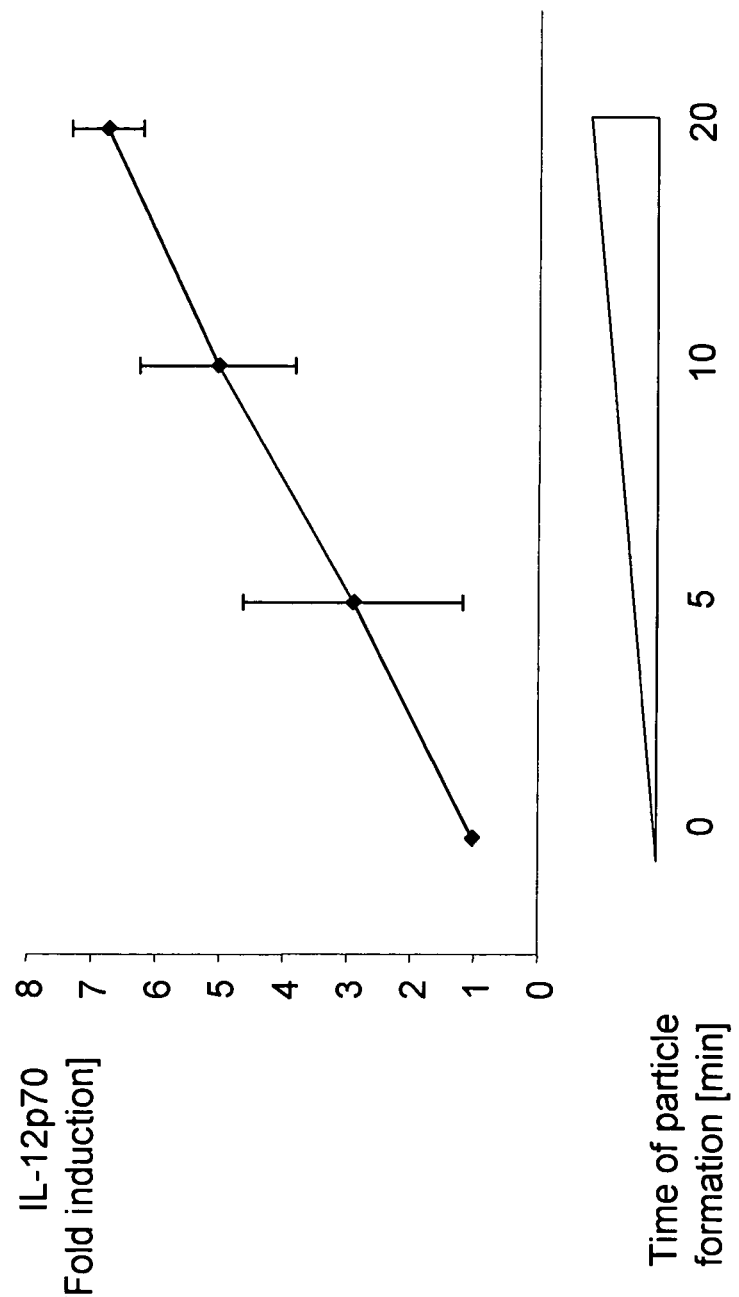
FIG. 3: PBMC from two different healthy donors were isolated and stimulated with poly-L-arginine (~88 AS) complexed ssRNA-oligonucleotide 9.2sense (5'-AGCUUAAC-CUGUCCUUCAA (SEQ ID NO: 194)). Time of complexation was either 0 min, 5 min, 10 min or 20 min. 24 hours after stimulation supernatants were harvested and analyzed for IL-12p70 production. Data from two individual donors were normalized (0 min value set to 1) and depicted as mean values ±SEM.
Figure 4:
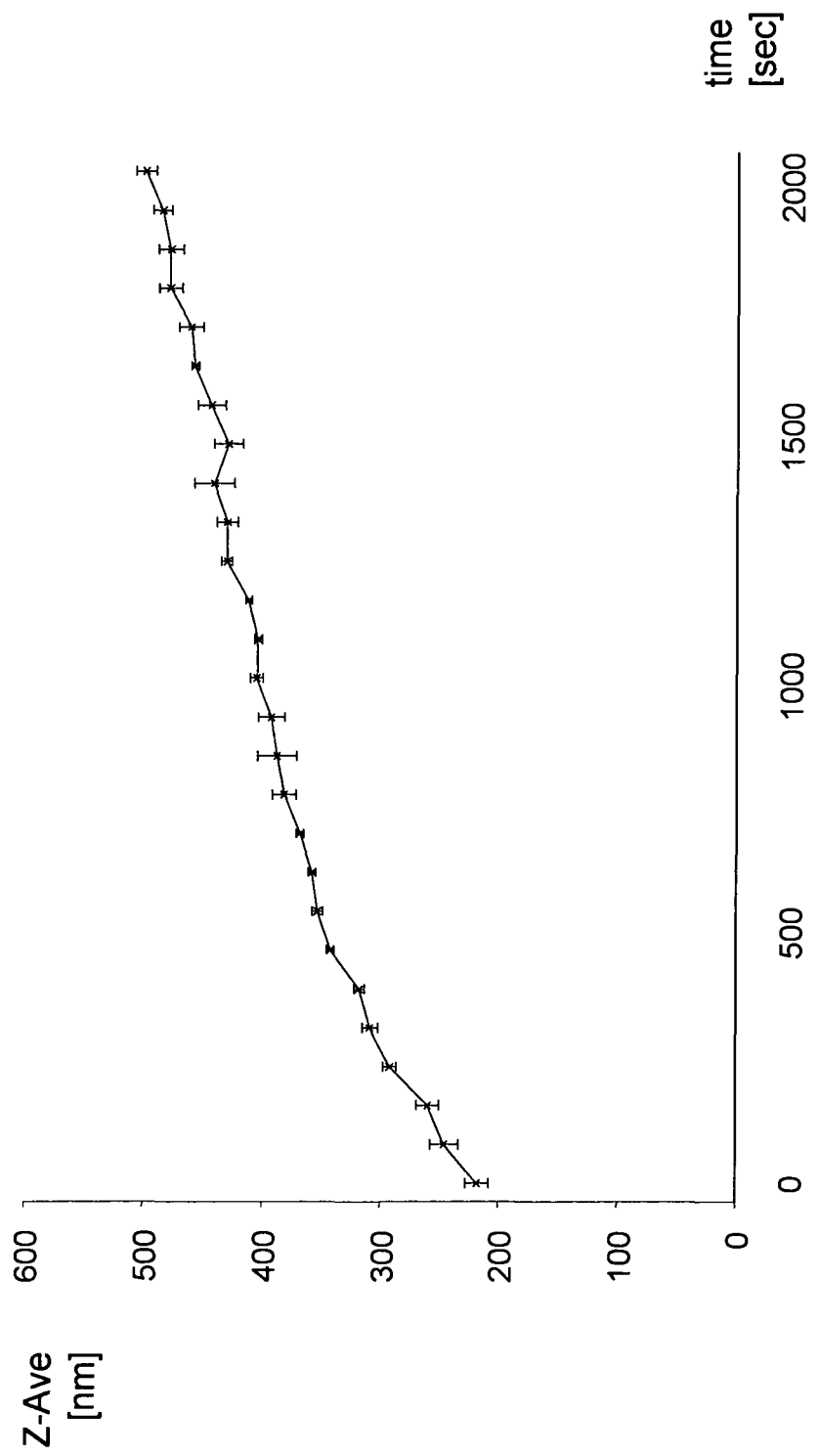
FIG. 4: PCS-measurement
Figure 5:
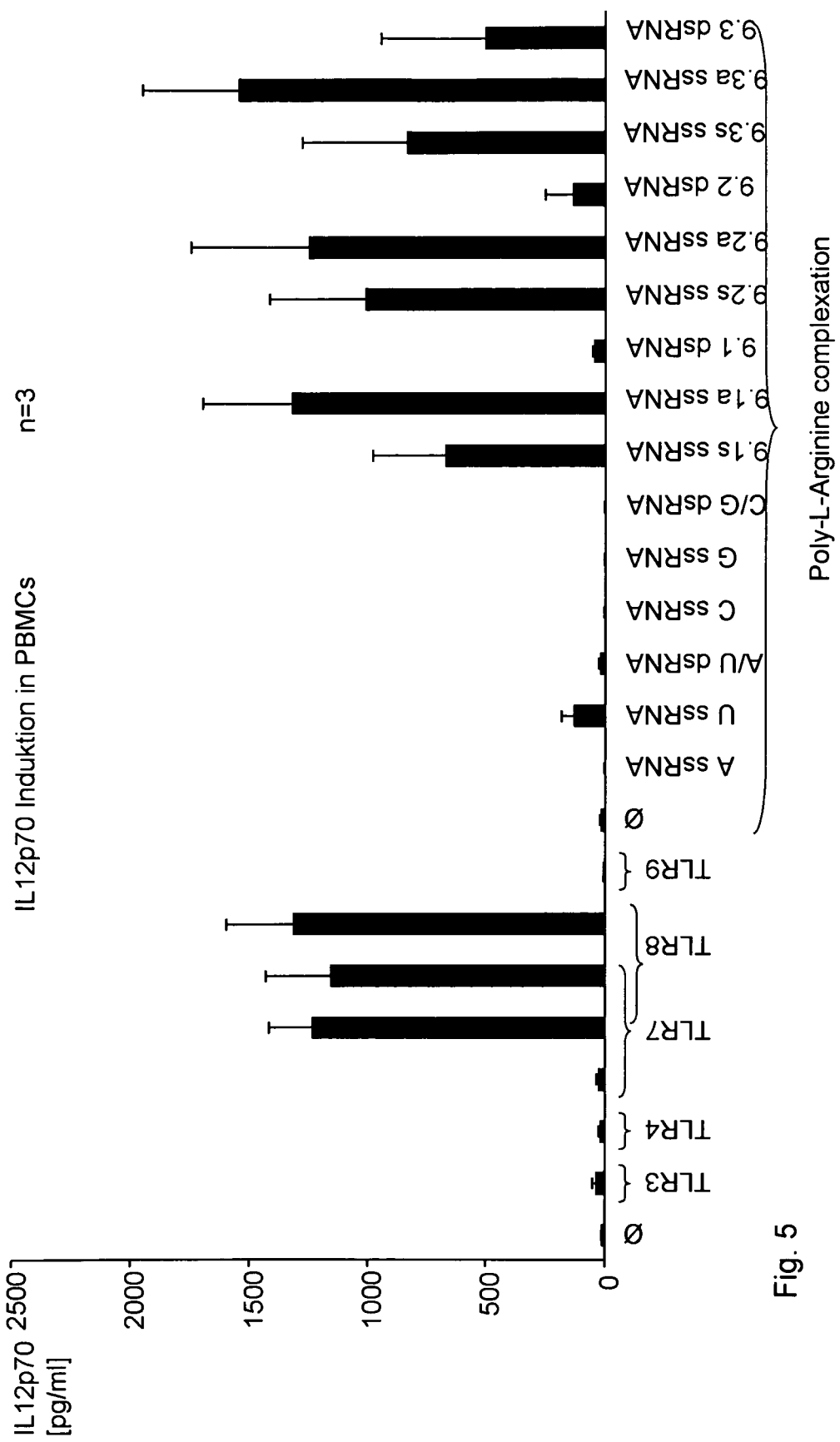
FIG. 5: PBMC from three different healthy donors were isolated and stimulated with the following stimuli (form left to right): medium, Poly I:C (10 µg/ml), LPS (1 µg/ml), 3M-001 (1 µM), 3M-007 (1 µM), R848 (5 µg/ml), 3M-002 (1 µM), CpG ODN2216 (3 µg/ml), (the following stimuli were all complexed using poly-L-arginine 88) medium, polyA ssRNA, poly U ssRNA, polyA/U dsRNA, polyc ssRNA, polyG ssRNA, poly C/G dsRNA, 9.1 sense ssRNA, 9.1antisene ssRNA, 9.1duplex dsRNA, 9.2sense ssRNA, 9.2 antisene ssRNA, 9.2duplex dsRNA, 9.3sense ssRNA, 9.3antisene ssRNA and 9.3duplex dsRNA. 24 hours after stimulation supernatants were harvested and analyzed for IL-12p70 (A) and TNF-a (B) production. Data from three individual donors were summarized and depicted as mean values ±SEM.

Maximal IL-12 Induction is Achieved After 20 Minutes of ssRNA-Complexation with poly-L-Arg In contrast to cationic lipids, for ssRNA-poly-L-Arg complexation little changes in concentrations of both the nucleic acid and the polycationic peptide (range: 50%-200%) had negligible impact on the activity of the complex (data not shown). Yet when we analyzed the time course of a particle formation and the corresponding immunostimulatory activity, a marked change in immunostimulation was observed. A linear increase in IL-12 production was seen with increasing complexation time. When poly-L-arginine was allowed 20 minutes to complex ssRNA oligonucleotides, a seven fold increase in IL-12 production was observed (FIG. 3). This increase in immunostimulatory activity was paralleled with an increase in particle size (FIG. 4). A plateau in immunostimulatory activity was reached after 20 minutes of complexation. Longer time for complexation did not result in higher immunostimulation (data not shown).

Example 4

Comparing poly-L-arginine ssRNA Oligonucleotides to Other TLR-Ligands

Next we compared poly-L-arginine complexed ssRNA oligonucleotides to established TLR-ligands in terms of immunostimulatory activity. For all TLR-ligands optimal concentrations were used that have been previously reported to activate PBMC. Among all established TLR-ligands only TLR8-activating compounds were able to induce IL-12p70 production within PBMC. This was true for the chimeric TLR7/TLR8 ligands R848 and 3M-007 and the TLR8-specific compound 3M-002. In addition all tested ssRNA oligonucleotides induced a marked IL-12p70 response within PBMC. Of note, whenever ssRNA oligonucleotides were tested in double-stranded conformation the IL-12 production was strongly reduced. Homopolymers of either polyA, polyC, polyG showed no activity, whereas polyU was able to elicit a slight yet consistent IL-12 response. These results indicated that ssRNA oligonucleotides harboring complex motifs rather than simple homopolymeric ssRNA oligonucleotides are are required to induce IL-12 production within PBMC.

Example 5

Maximal IL-12 Production Within PBMC Depends on the Presence of CD14+ Monocytes

Figure 6:
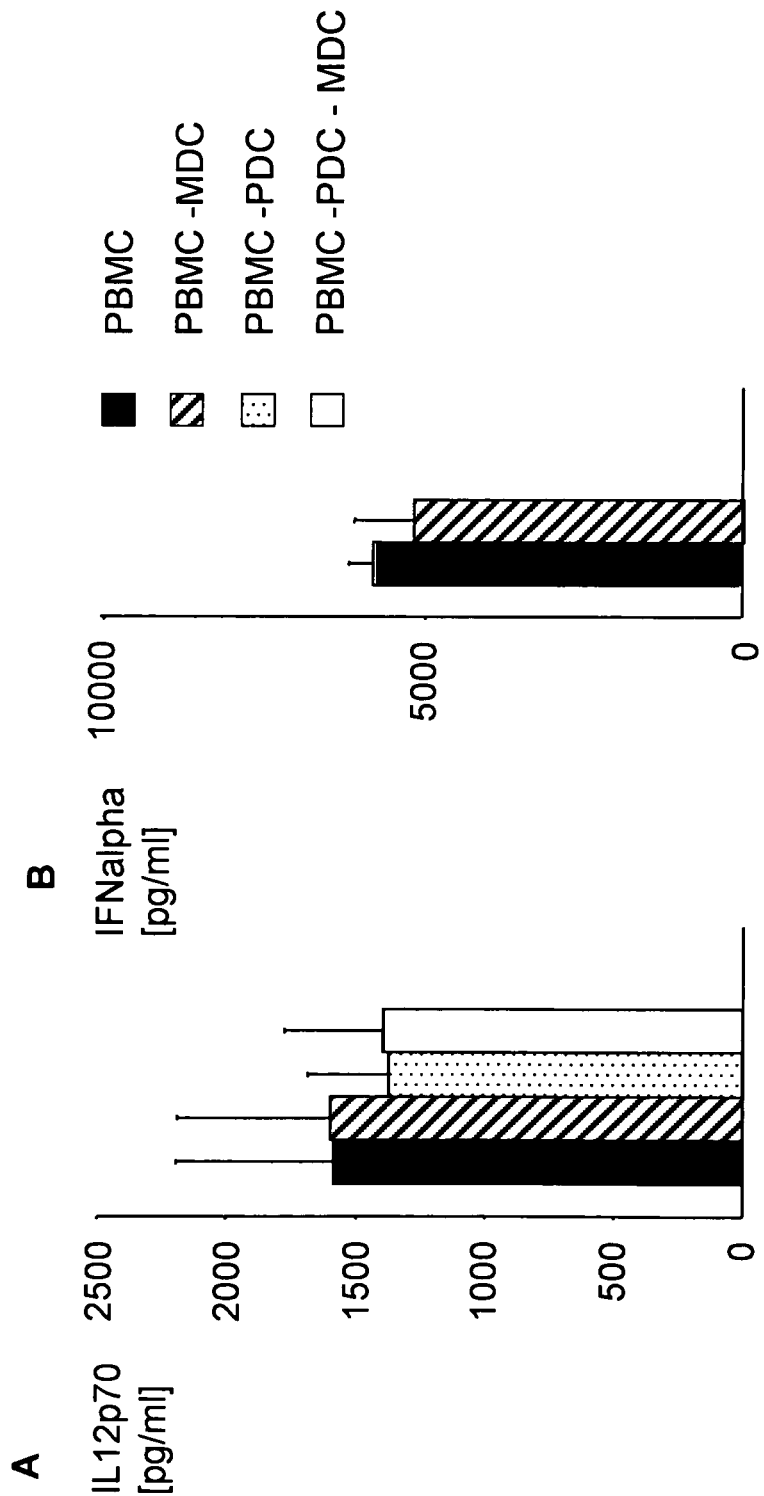
FIG. 6: PBMC from two different healthy donors were isolated. PDC and MDC were depleted from PBMC using MACS. PBMC were reconstituted with either PDC, MDC, MDC and PDC or nothing and subsequently stimulated with poly-L-arginine (~88 AS) complexed ssRNA-oligonucleotide 9.2sense (5'-AGCUUAACCUGUCCUUCAA (SEQ ID NO: 194)). 24 hours after stimulation supernatants were harvested and analyzed for IL-12p70 production (A) and IFN-a production (B). Data from two individual donors were summarized and are depicted as mean values ±SEM.
Figure 7:
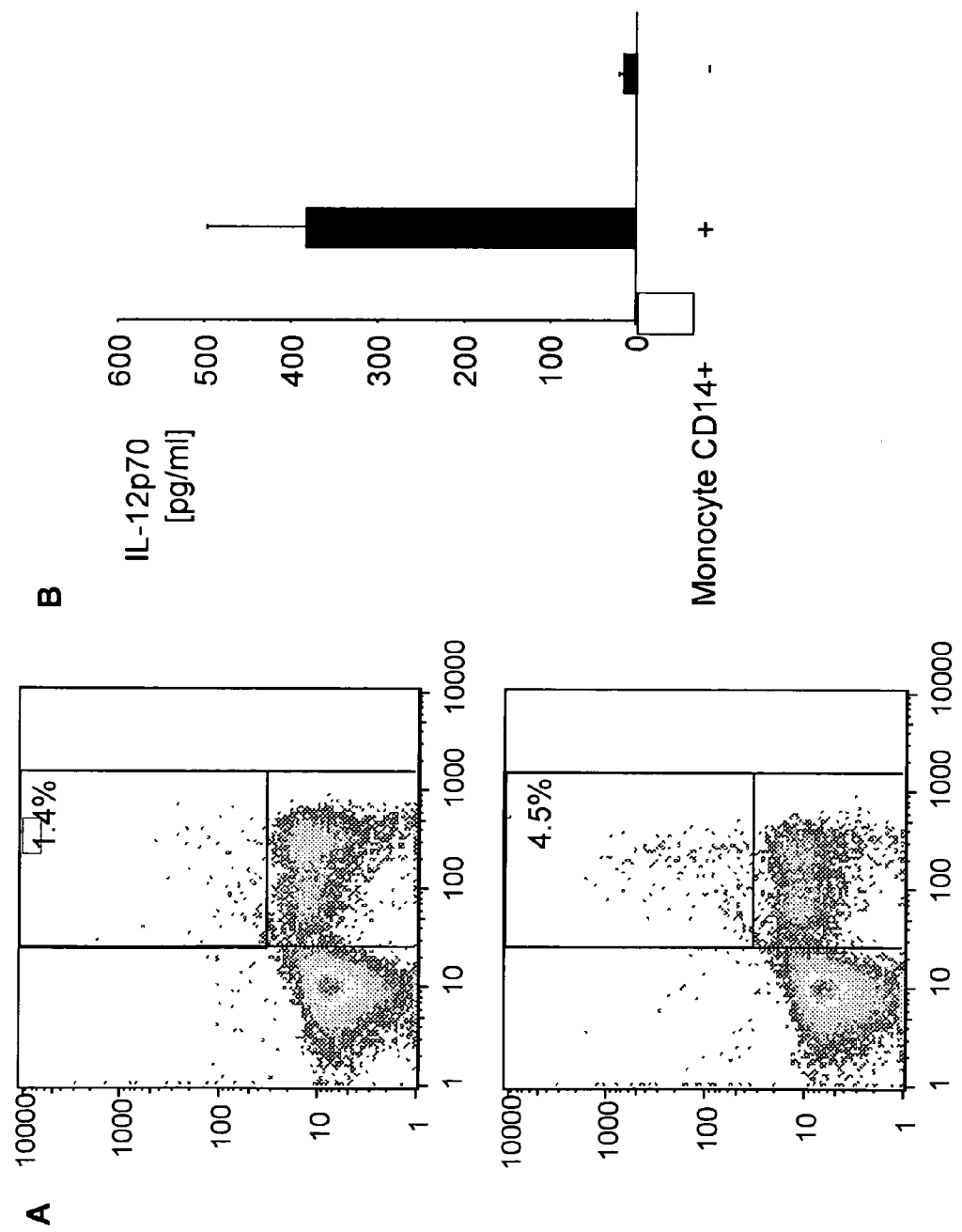
FIG. 7: A: PBMC were stimulated with either poly-L-arginine (~88 AS) complexed ssRNA-oligonucleotide 9.2sense (5'-AGCUUAACCUGUCCUUCAA (SEQ ID NO: 194)) or poly-L-arginine alone. Six hours after stimulation brefeldin A was added and after three more hours cells were harvested and intracellular IL-12 production was analyzed using FACS. Data from two individual donors are shown. In addition, PBMC from two different donors were isolated. CD14 positive cells were depleted via MACS. One fraction (CD14+) was reconstituted with CD14 positive cells, whereas one fraction was left untreated. Subsequently cells were stimulated with poly-L-arginine (~88 AS) complexed ssRNA-oligonucleotide 9.2sense (5'-AGCUUAACCUGUC-CUUCAA (SEQ ID NO: 194)). 24 hours after stimulation supernatants were analyzed for IL-12p70 production. Data from two individual donors were summarized and are depicted as mean values ±SEM (B). Monocytes were isolated from PBMC via depletion using MACS. Monocytes were stimulated with poly-L-arginine (~88 AS) complexed with either RNA-oligonucleotides polyA, polyU, polyA/U, polyC, polyG, polyC/G, 9.1 sense, 9.1 antisense, 9.1duplex, 9.2sense, 9.2antisense, 9.2duplex, 9.3sense, 9.3antisense, 9.3duplex (for a detailed listing see table 1). In addition LPS (1 µg/ml), polyI:C (10 µg/ml), R848 (5 µg/ml) were used to stimulate cells. 24 hours after stimulation supernatants were analyzed for IL-12p70 (C) and TNF-a (D) production. Data from two individual donors were summarized and are depicted as mean values ±SEM.
Figure 7:
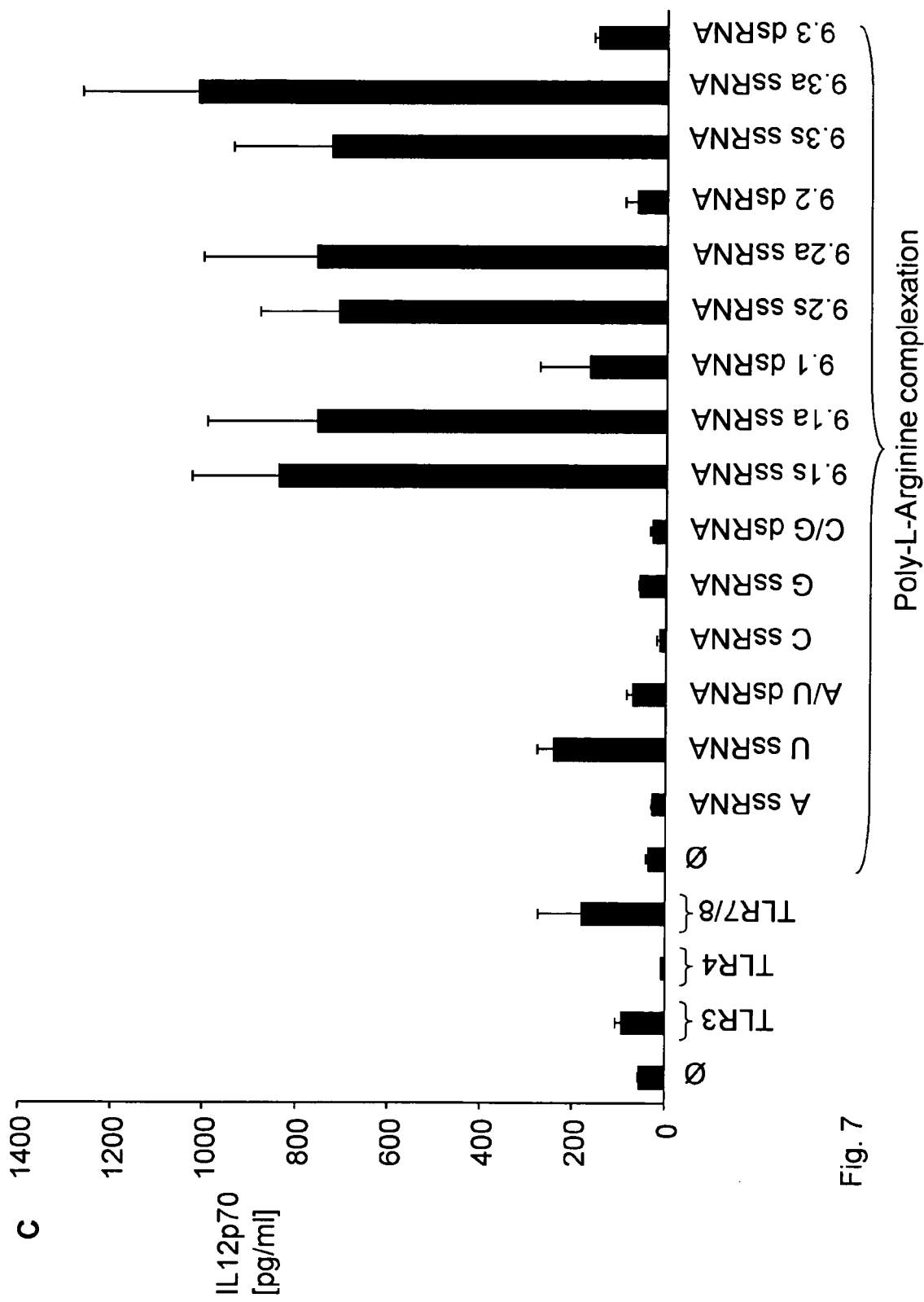

We have previously shown that Lipofectamine-complexed ssRNA mediates IFN-a production only in the presence of plasmacytoid dendritic cells [10]. In analogy, when poly-L-arginine was used to complex ssRNA oligonucleotides, IFN-a production was completely abrogated in the absence of PDC (FIG. 6B). However, when PDC were depleted from PBMC no decrease in the ssRNA oligonucleotide mediated IL-12 induction was seen. Interestingly this was also true for the depletion of myeloid dendritic cells (FIG. 6A), thus indicating that within PBMC other cell types than the two major subsets of dendritic cells are responsible for the production of large amounts of IL-12p70 in response to ssRNA oligonucleotide stimulation. In order to decipher the cell type responsible for the observed IL-12 production, we employed intracellular FACS-staining for IL-12 combined with appropriate antibodies for the classical lineage marker. Using this technique, we were able to identify CD14+ monocytes as the main source of IL-12 production within PBMC (FIG. 7A). Moreover, when CD14+ cells were depleted from PBMC using MACS the ssRNA oligonucleotide mediated IL-12 response was completely abrogated (FIG. 7B). Purification of monocytes confirmed that no other cell type was required for IL-12 production in response to ssRNA oligonucleotide stimulation (FIG. 7C). Interestingly, when we compared the chimeric TLR7/TLR8 ligand R848 to ssRNA oligonucleotides in terms of IL-12 induction, we observed an almost five-fold difference in favor of the complexed ssRNA oligonucleotides.

Example 6

Single-Strand Conformation of RNA-Ligands is Required for Potent IL-12 Induction In above described experiments we had shown that single-strand conformation of RNA oligonucleotides is necessary for maximal IL-12 induction within PBMC. Annealing of the complementary ssRNA oligonucleotide led to a complete abrogation of the IL-12 inducing activity. To address this phenomenon in more detail we performed a set of experiments in which we used shorter versions of a complementary ssRNA oligonucleotide to generate partially double-stranded ssRNA oligonucleotides. For these experiments, the ssRNA oligonucleotide 9.2antisense was used as a standard control oligonucleotide whereas ssRNA oligonucleotides that were complementary to 9.2antisense were designed to achieve partially double stranded compounds (for a detailed listing see table 1). Both within PBMC and in monocytes (FIGS. 8A and B), a marked reduction in IL-12 production was seen with increasing amounts of complementary bases. Already a segment of 12 complementary bases (9.2A/9.2antisense combination) reduced the immunostimulatory activity of 9.2antisense to less than 20% of the original ssRNA oligonucleotide. An almost complete reduction was obtained as soon as a complete dsRNA conformation was reached. Double stranded conformation of ssRNA oligonucleotides can also be obtained when palindromic stretches are contained within a sequence by either hairpin conformation or self hybridization. To address this possibility we designed a panel of ssRNA oligonucleotides starting with a complete palindromic sequence and respective derivates with increasing amounts of mismatches (see table 2). The completely palindromic sequence and its close derivates proved to be double-stranded 20mer RNA oligonucleotides, when analyzed on a gel (data not shown). This indicated that under these conditions palindromic ssRNA oligonucleotides avidly formed dsRNA by self hybridization rather than hairpin conformation. As anticipated from above findings, palindromic RNA oligonucleotides proved to be poor in inducing IL-12 production within PBMC and monocytes (FIGS. 8C and D). In contrast, when mismatches were introduced to avoid self hybridization a strong IL-12 response could be elicited.

Example 7

Figure 8:
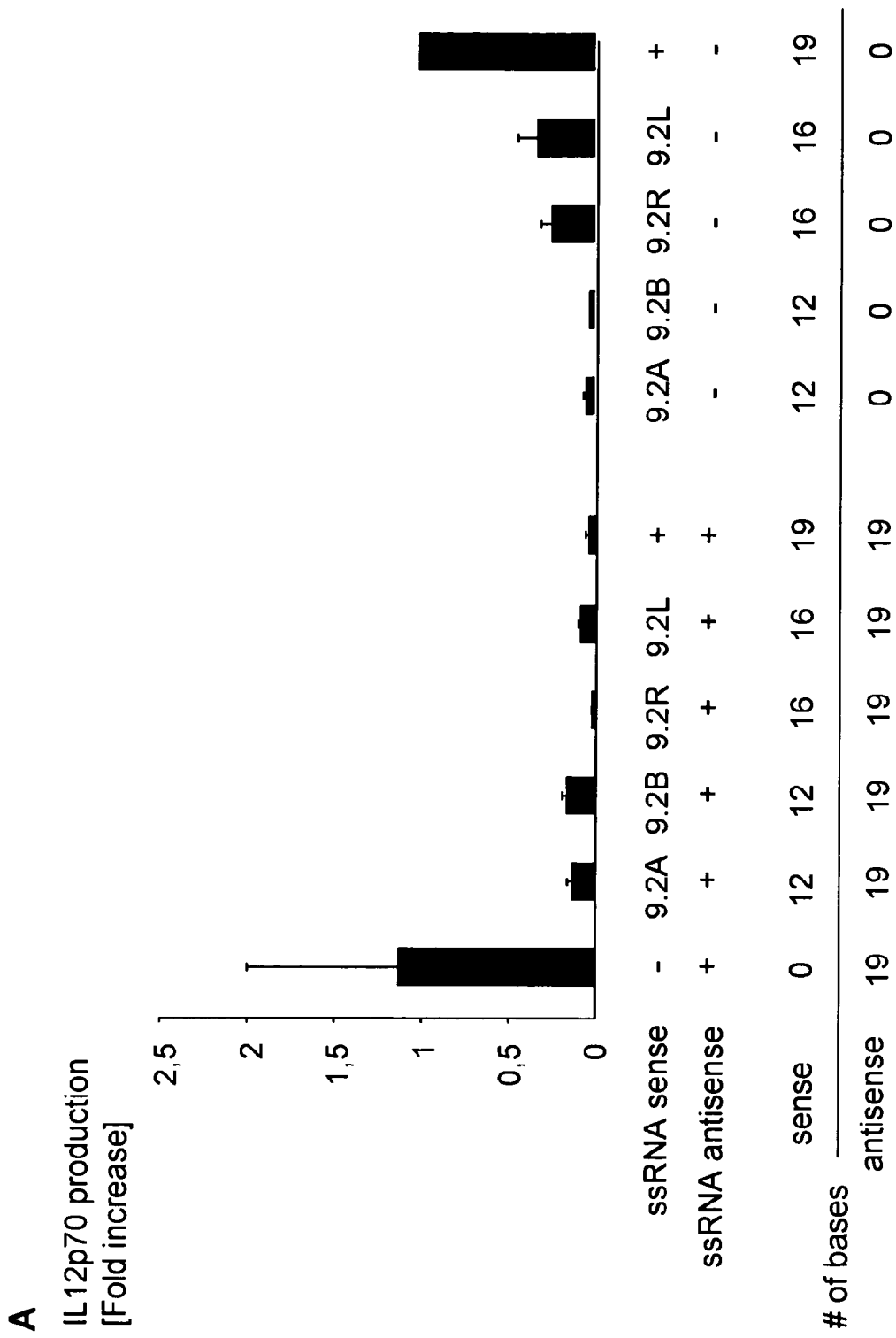
FIG. 8: PBMC or monocytes from three or two different healthy donors were isolated and stimulated with poly-L-arginine complexed ssRNA oligonucleotides (see table 1). Shortened versions of ssRNA oligonucleotides 9.2sense were tested: 9.2L ssRNA (16mer), 9.2R ssRNA (16mer), 9.2A ssRNA (12mer), 9.2B ssRNA (12mer). RNA oligonucleotides were either tested in their ssRNA conformation or after annealing with the corresponding antisense strand 9.2antisense. 24 hours after stimulation supernatants were analyzed for IL-12p70 production. Data were normalized to ssRNA 9.2sense and are depicted as mean values ±SEM for PBMC (A) and monocytes (B). In addition a panel of self complementary ssRNA oligonucleotides (see table 2) were tested on both PBMC (C) and monocytes (D): ssRNA oligonucleotides were complexed using poly-L-arginine and used to stimulate PBMC from three individual donors and monocytes from two individual donors. 24 hours after stimulation supernatants were analyzed for IL-12p70 production. Data were normalized to ssRNA M20 and are depicted as mean values ±SEM for PBMC (C) and Monocytes (D).
Figure 8:
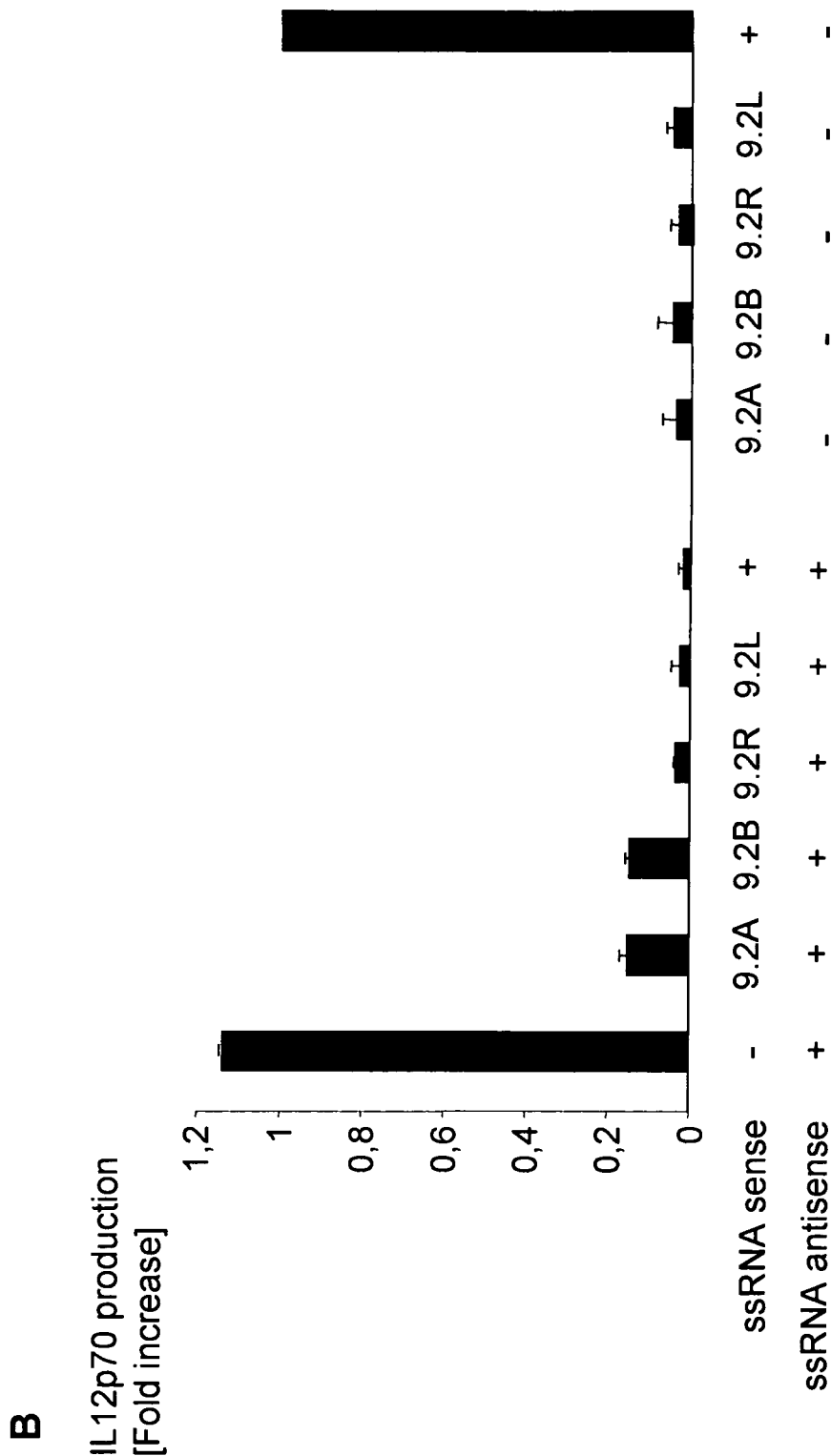
Figure 8:
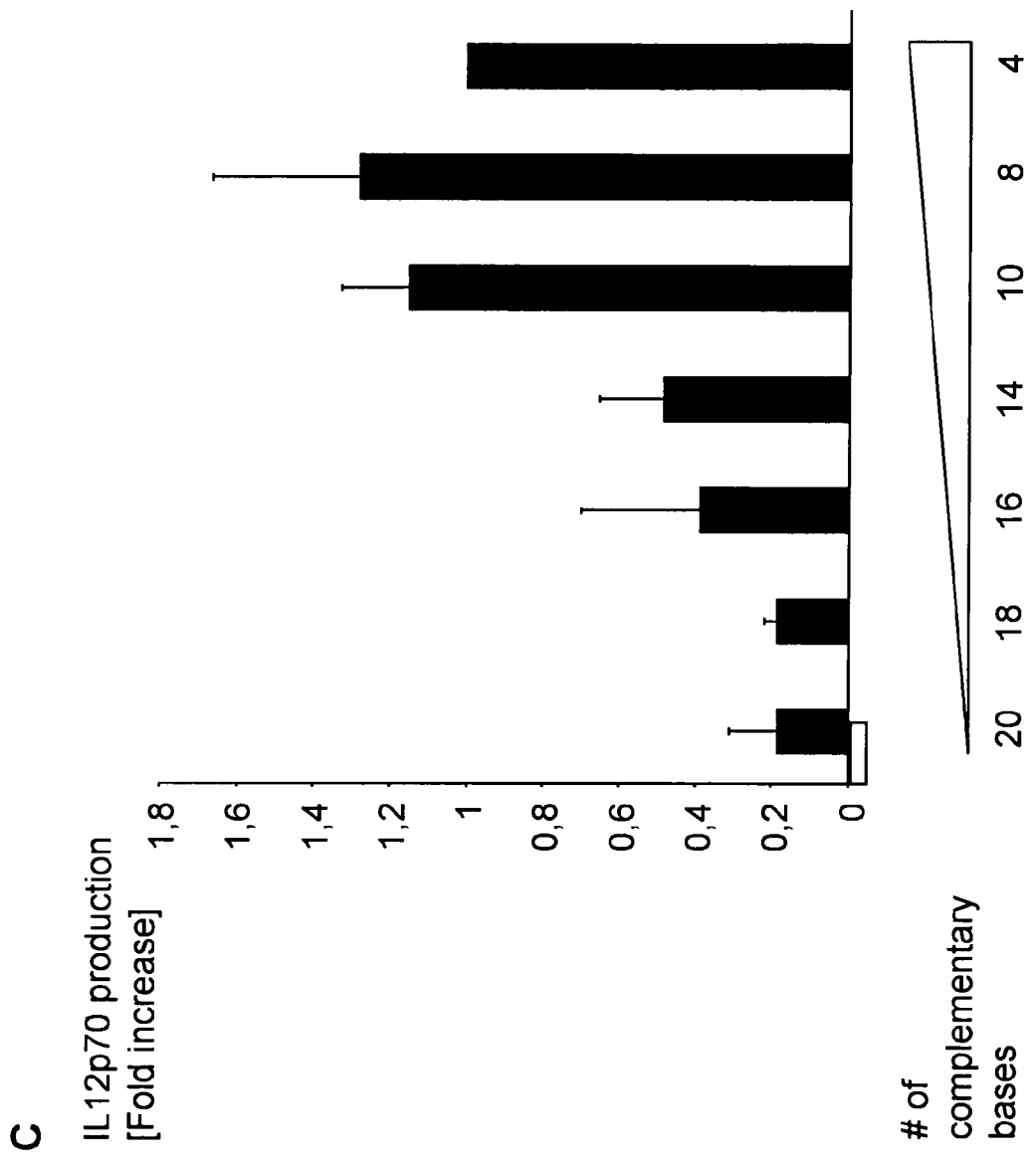
Figure 8:
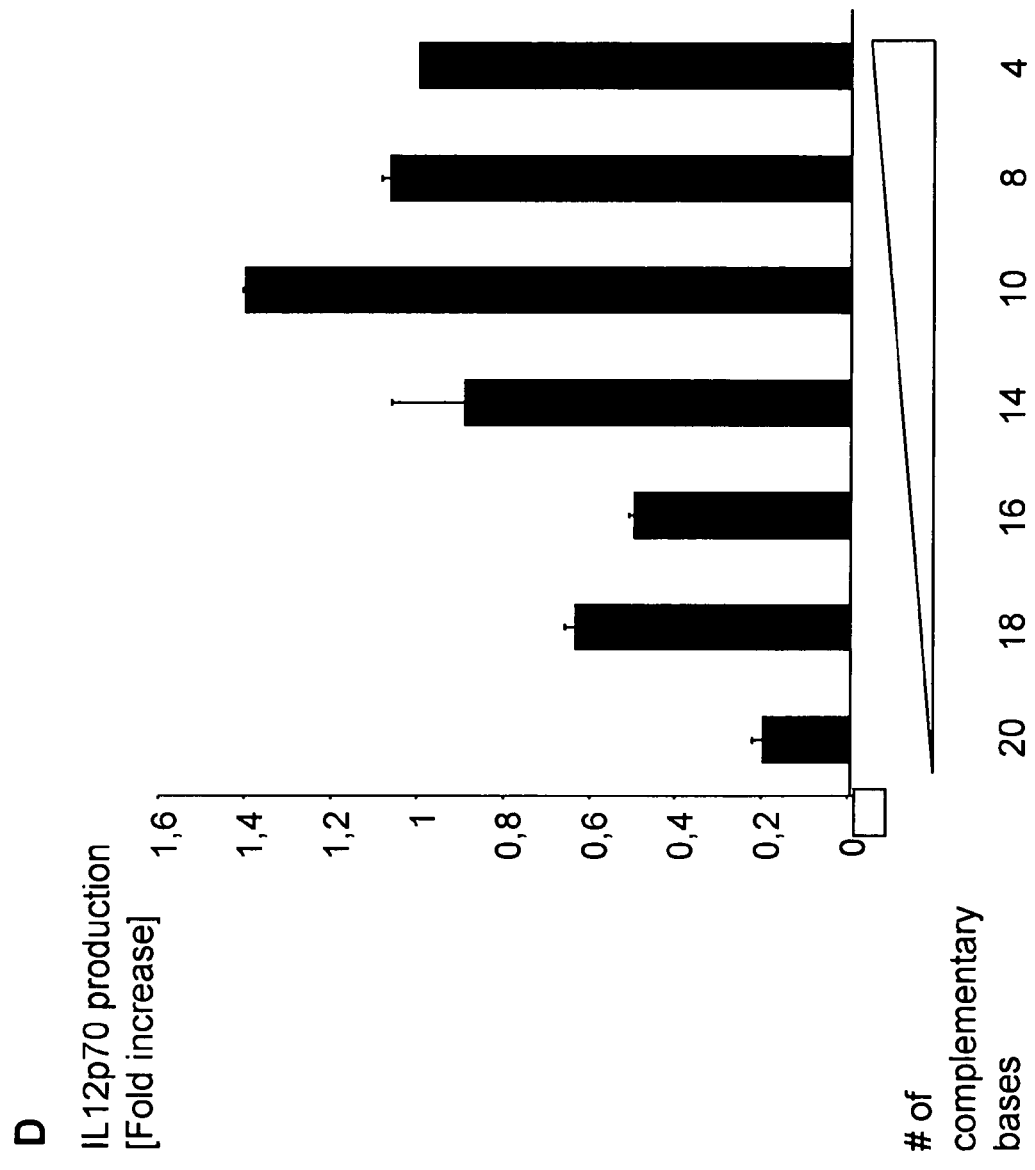
Figure 9:
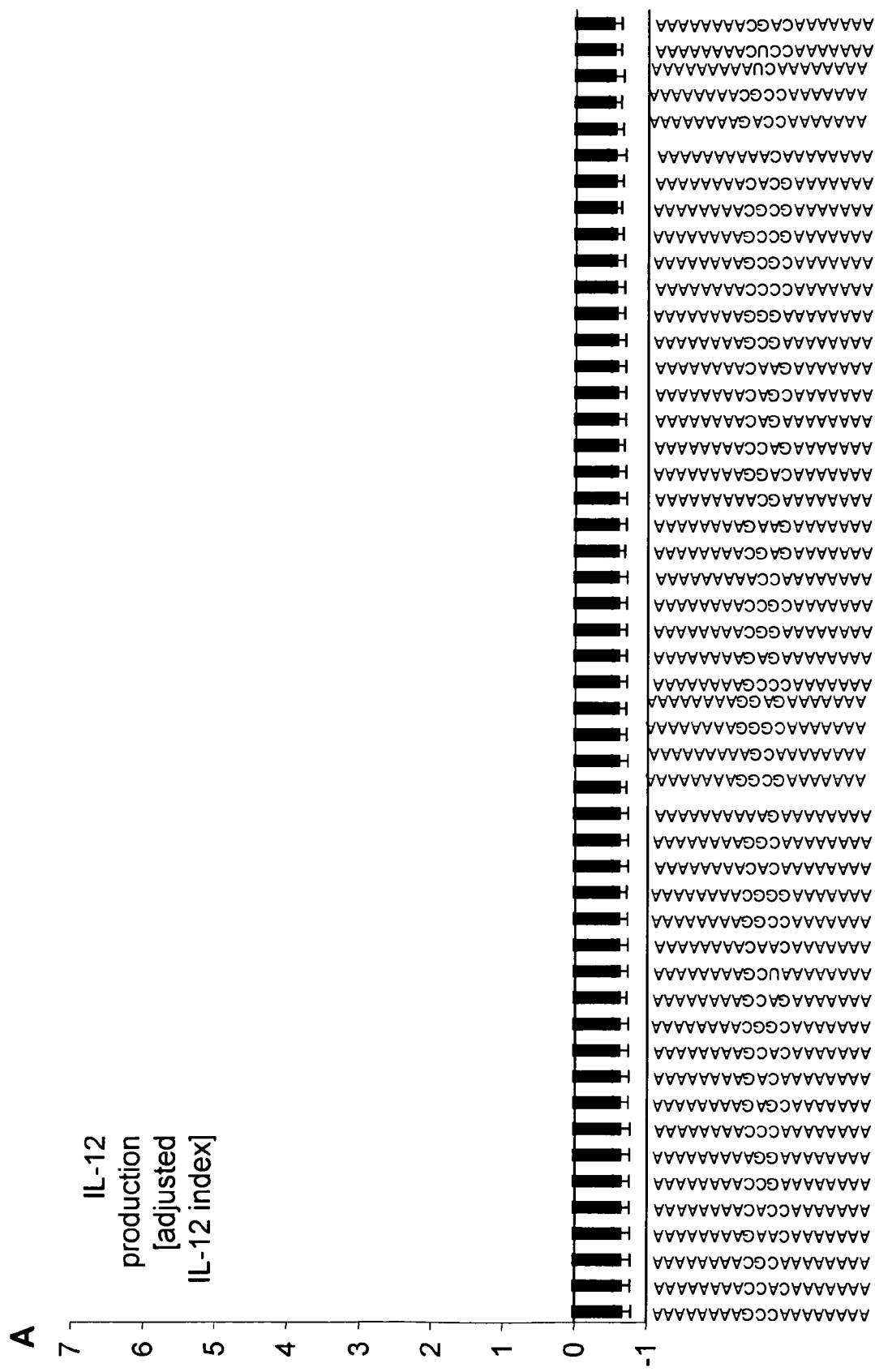
FIG. 9: PBMC of six different healthy donors were isolated and stimulated with poly-L-arginine complexed ssRNA oligonucleotides in duplicates. 44 hours after stimulation IL-12p40 production was assessed in supernatant via ELISA. For all tested ssRNA oligonucleotides (table 3), the mean values of the measured duplicates were normalized to the positive control ssRNA oligonucleotide 9.2sense (5'-AGCU-UAACCUGUCCUUCAA (SEQ ID NO: 194)) by dividing the mean value of tested oligonucleotide by the mean value of 9.2sense (=IL-12 index of a given oligonucleotide). Next, all individual IL-12 indices were adjusted to the mean value of all IL-12 indices by subtracting the mean value of all IL-12 indices from the individual IL-12 index of a given oligonucleotide (=adjusted IL-12 index). Data from six individual donors were summarized and were assorted in ascending order displaying the corresponding SEM (for a complete listing including numerical data see table 4).
Figure 9:
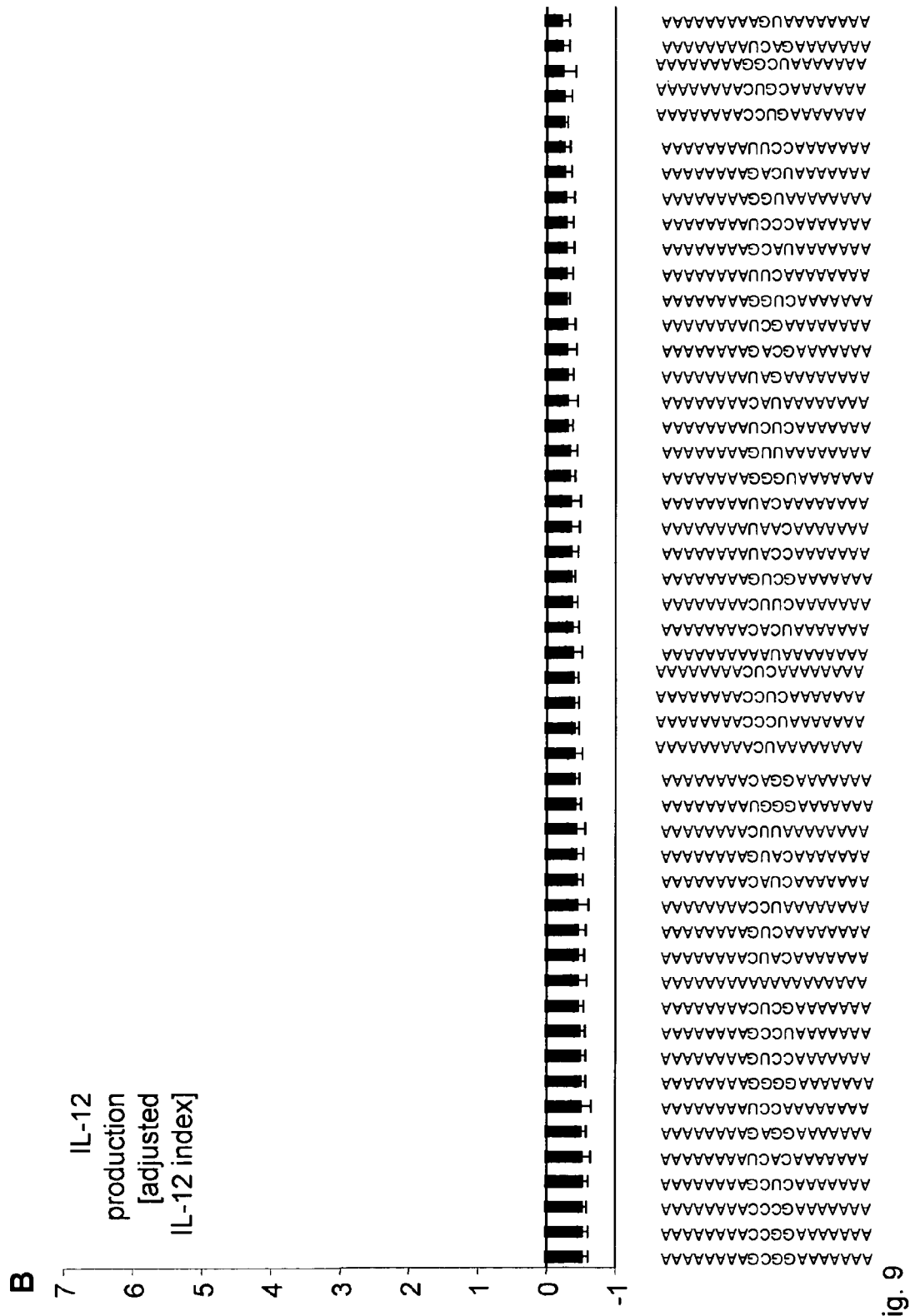
Figure 9:
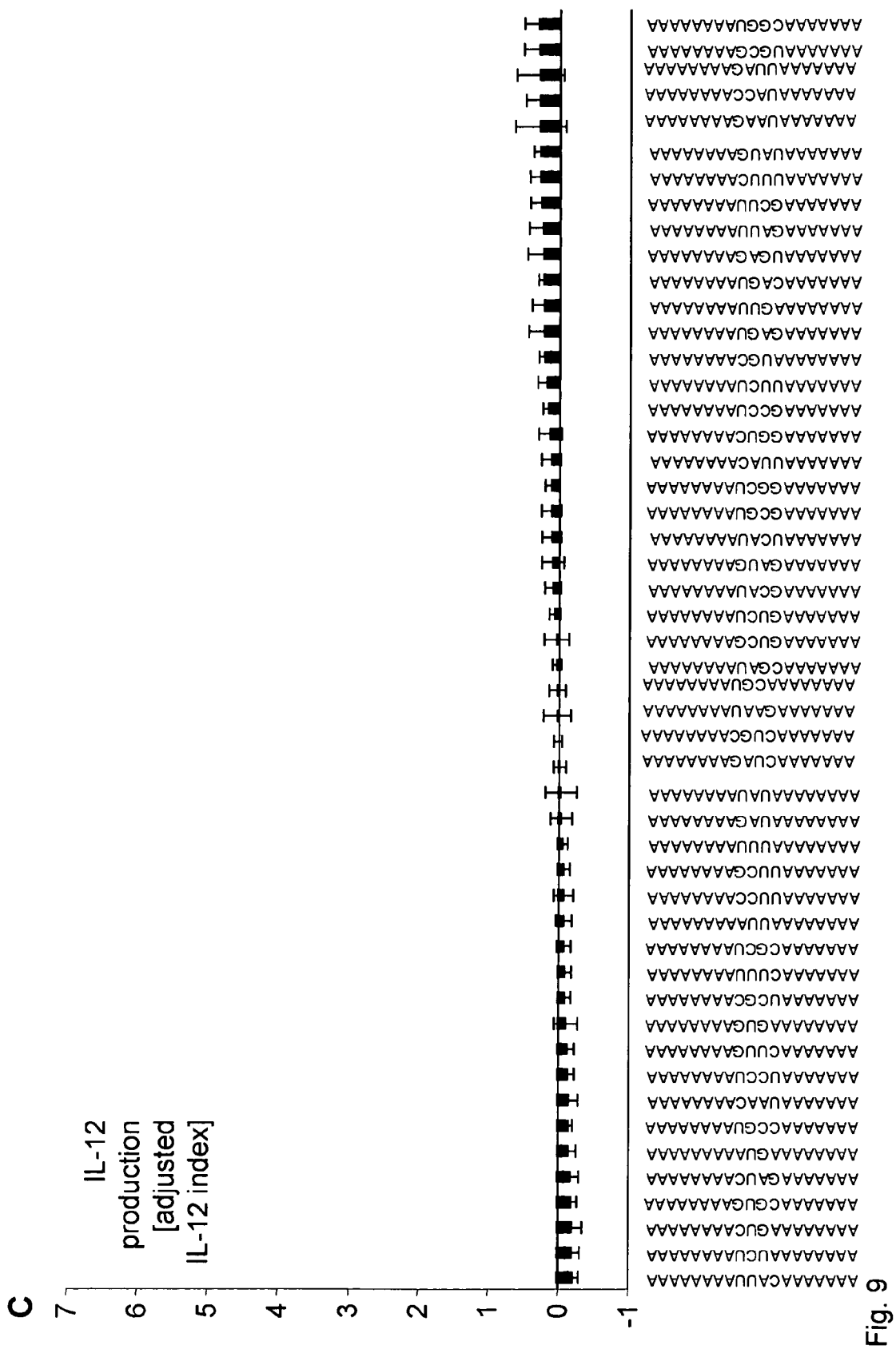
Figure 9:
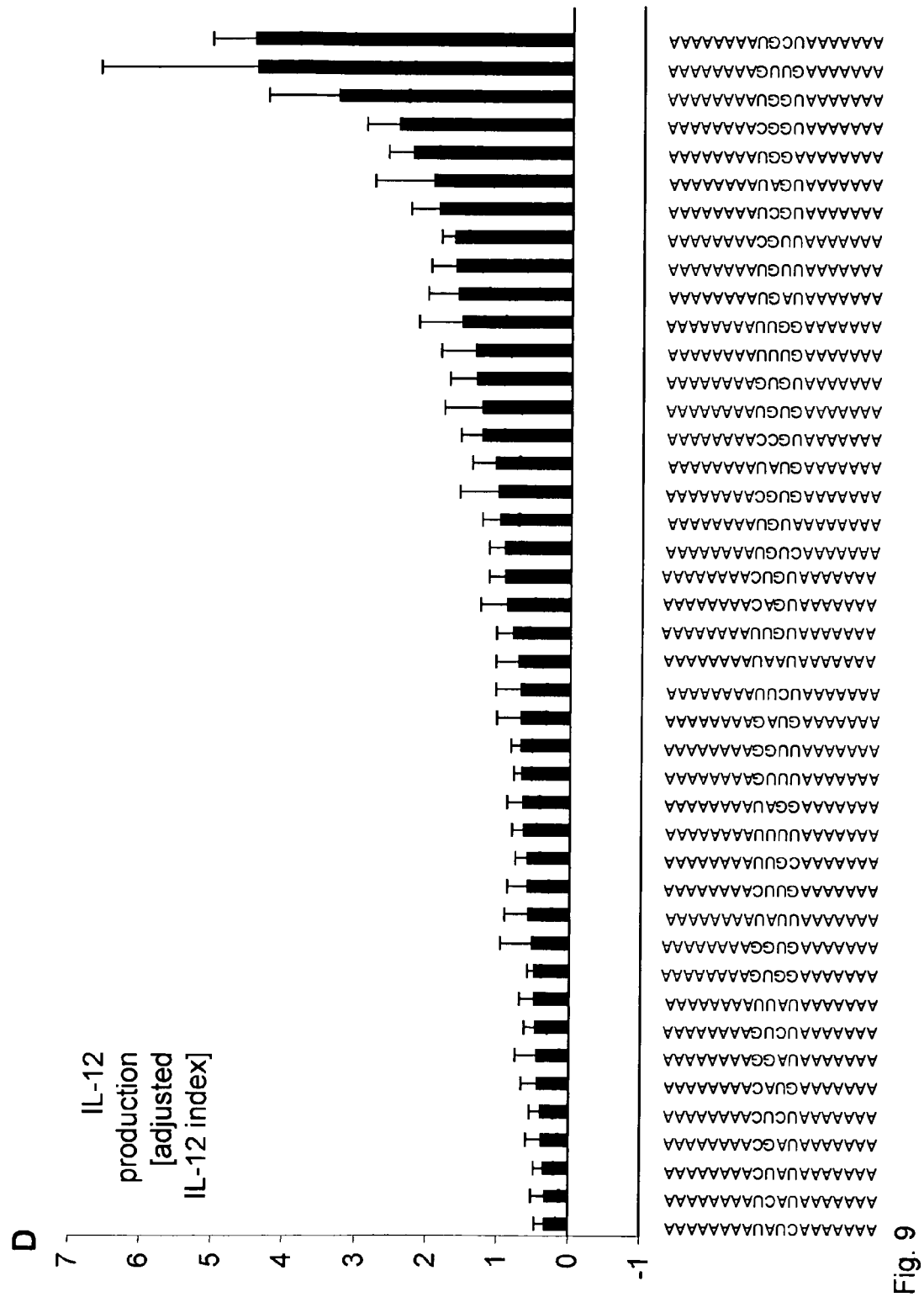

Rational Design of a 4mer-Motif Library to Screen for Potent Motifs within ssRNA Previous experiments have shown that a minimal length of 19 bases is required for maximal IL-12 induction by ssRNA oligonucleotides (see FIG. 8). Since poly adenosine oligonucleotides proved to be inactive in terms of IL-12 induction, we decided to generate a ssRNA oligonucleotide library by placing putative motifs into the centre of poly adenosine RNA oligonucleotides. We generated a library of ssRNA oligonucleotides comprising all possible 4mer motifs in the centre of a poly adenosine oligonucleotide. In view of the fact that the flanking adenosine residues can be part of a 4mer RNA sequence motif, only 193 ssRNA oligonucleotides (Table 3) were needed to cover all 256 possible 4mer motifs.

Example 8

Generation and Processing of Raw Data

All 193 ssRNA oligonucleotides were tested on PBMC of six individual healthy donors using poly-L-Arg for complexation. At 44 hours after stimulation with RNA oligonucleotides, supernatants were collected and IL-12 production was measured by ELISA. Prior to statistical analysis the raw data were processed as follows: for each cell culture plate the mean IL-12 value of the experimental duplicates for each tested ssRNA oligonucleotide were normalized to the ssRNA oligonucleotide RNA9.2sense (5'-AGCUUAACCUGUC-CUUCAA-3' (SEQ ID NO: 194)). This standard RNA oligonucleotide was included as a positive control on all cell culture plates. Normalization was performed by calculating the ratio of IL-12 induced by the tested oligonucleotide and IL-12 induced by the standard oligonucleotide RNA9.2sense. Thus, for each tested oligonucleotide in an individual donor a mean ratio of IL-12 induction was obtained. In the following, this mean of the ratios is referred to as IL-12 index (one value of IL-12 index per donor). For example testing ssRNA-oligonucleotide ANP175 (5'-AAAAAAAUGCUAAAAAAA-3' (SEQ ID NO: 175)) in donor 3 gave the mean of the two raw values of the duplicates (IL-12 in supernatant) of 1725 pg/ml, whereas the control oligonucleotide RNA9.2sense (5'-AGCUUAACCUGUCCUUCAA-3' (SEQ ID NO: 194)) resulted in 908 pg/ml. The corresponding IL-12 index of oligonucleotide ANP175 for donor 3 was calculated to be 1.90 (=1725 pg/ml divided by 908 pg/ml).

Figure 10:
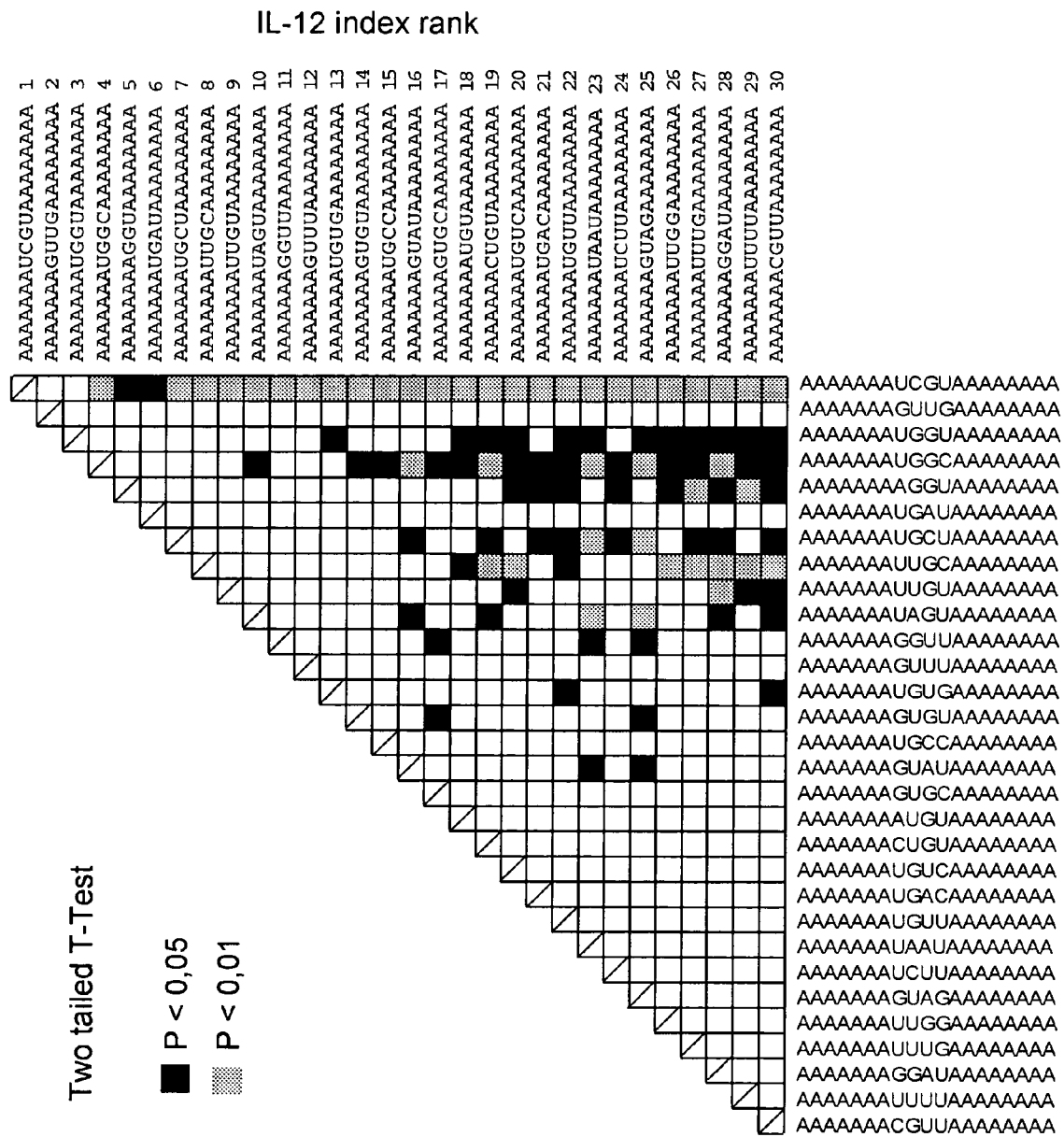
FIG. 10: A statistical analysis was performed to assess a putative significant difference for the adjusted IL-12 indices of all top thirty ssRNA oligonucleotides. A two-tailed Student's t-test was employed to calculate the p-value off all possible ssRNA oligonucleotide combinations. A p-value >0,01 and <0,05 is depicted by a black box, whereas a p-value <0,01 is depicted as a grey box.

Next, the means of all IL-12 indices for every individual donor were calculated. Then the adjusted IL-12 indices were calculated as IL-12 index minus the mean of all IL-12 indices of one individual donor. For example ssRNA oligonucleotide ANP175 of donor 3 (5'-AAAAAAAUGCUAAAAAAA-3' (SEQ ID NO: 175)) had an IL-12 index of 1.90, whereas the mean of all IL-12 indices of donor 3 was 0.44. The adjusted IL-12 index of ANP175 was calculated: 1.90 minus 0.44=1.46. The adjusted IL-12 indices from all six donors were summarized by calculating the means and the corresponding standard error of mean. The data are depicted in ascending order (FIG. 9A, B, C, D). The adjusted IL-12 indices of the top thirty ssRNA oligonucleotides of all six donors were compared using a two-tailed Student's t-test (FIG. 10). For most combinations tested, a significant difference was observed when the interval between the analyzed pairs was at least eight or nine places in the assortment.

Example 9

Calculating an Individual IL-12 Score for 1 mer-, 2mer- and 3mer-Motifs

A mean IL-12 index for all possible 1mer motifs (5'-X-3'), 2mer motifs (5'-XX-3',5'-X*X-3', 5'-X**X-3') or 3mer motifs (5'-XXX-3',5'-XX*X-3',5'-X*XX-3') was obtained by calculating a mean IL-12 index of all ssRNA-oligonucleotides containing the corresponding motifs. This mean IL-12 index is referred to as the IL-12 score of a given motif. For example the 3mer motif 5'-U*GU-3' was contained in ssRNA-oligonucleotides ANP 154, 166, 178 and 190 with respective adjusted IL-12 indices of 1.57, 4.42, 3.26 and 1.6. The IL-12 score of the 3mer motif 5'-U*GU-3' was thus calculated to be 2.71 with a standard error of mean of 0.69. The calculation of the IL-12 score of a motif did not account for the position of the motif within the sequence of the corresponding ssRNA oligonucleotides. Multiple occurrences of one motif within the same ssRNA-oligonucleotide was accounted for by adding the corresponding IL-12 index times the number of its occurrence within the oligonucleotide to the calculation of the corresponding IL-12 score of the motif. Consequently an IL-12 score could be assigned to all possible 1mer motifs (5'-X-3'), 2mer motifs (5'-XX-3',5'-X*X-3',5'-X**X-3') or 3mer motifs (5'-XXX-3',5'-XX*X-3',5'-X*XX-3') (FIG. 11).

Example 10

Using the IL-12 Score of 1mer-, 2mer- and 3mer-Motifs to Predict ssRNA-Oligonucleotides with a Low or High IL-12 Index Next we tested the predictive value of the calculated 1mer-, 2mer- and 3mer-motif IL-12 scores to predict ssRNA oligonucleotides with a low or high IL-12 index. Thus for each ssRNA oligonucleotide the occurrence of a set of motifs was tested and the respective IL-12 scores were assigned to the ssRNA. For example for the panel of 3mer motifs with unspaced sequences (5'-XXX-3') the ssRNA-oligonucleotide ANP 175 (5'-AAAAAAAUGGUAAAAAAA-3' (SEQ ID NO: 448)) was analyzed the following way:

| 3mer motif (5'-XXX-3') | IL-12 score | Occurrences within the ssRNA oligonucleotide ANP 175 | Assigned IL-12 score |
|---|---|---|---|
| 5'-AAA-3' | −0.0117 | 11 | −0.1287 |
| 5'-UAA-3' | +0.3798 | 1 | +0.3798 |

| 3mer motif (5'-XXX-3') | IL-12 score | Occurrences within the ssRNA oligonucleotide ANP 175 | Assigned IL-12 score |
|---|---|---|---|
| 5'-AAU-3' | +0.4008 | 1 | +0.4008 |
| 5'-AUG-3' | +0.7997 | 1 | +0.7997 |
| 5'-UGG-3' | +0.8403 | 1 | +0.8403 |
| 5'-GUA-3' | +0.9657 | 1 | +0.9657 |
| 5'-GGU-3' | +1.0603 | 1 | +1.0603 |
| | | | +4.3180 |

All ssRNA oligonucleotides were assigned an individual IL-12 score for all possible motif-combinations (1mer-, 2mer- and 3mer-motifs). Next, the prediction that was obtained by using the assigned IL-12 scores were compared to the actual adjusted IL-12 indices for all ssRNA-oligonucleotides and for each motif combination. Data were sorted in ascending order according to the adjusted IL-12 indices. For all predictions, the correlation coefficient was calculated: Using the IL-12 scores of 1mer motifs (5'-X-3') to predict the actual adjusted IL-12 indices off all ssRNA oligonucleotides a correlation coefficient of 0.6 was obtained (FIG. 12A). When 2mer motifs were used to predict the adjusted IL-12 indices a correlation coefficient of 0.70 was obtained for 5'-XX-3'-motifs, a correlation coefficient of 0.65 for 5'-X*X-3'-motifs and a correlation coefficient of 0.65 for 5'-X**X-3'-motifs (FIG. 12B). Using 3mer motifs to predict the adjusted IL-12 indices, a correlation coefficient of 0.76 was calculated for 5'-XXX-3'-motifs, of 0.75 for 5'-XX*X-3'-motifs and of 0.76 for 5'-X*XX-3'-motifs. When only the IL-12 scores of 3mer motifs were considered that were significantly higher or lower than the IL-12 scores of the other motifs (see FIG. 11C) a correlation coefficient of 0.78 could be obtained (correlations for prediction with different types of motifs see FIG. 12).

Example 11

Determined the Threshold IL-12 Scores for High and Low Immunostimulatory Activity The immunostimulatory activity of any given RNA oligonucleotide can be predicted using the 3mer-based algorithm as described previously. For research and drug discovery and development purposes, two groups of RNA oligonucleotide are of interest: Group A oligonucleotides which have high or maximal IL-12-inducing activity, and Group B oligonucleotides which have low or minimal IL-12-inducing activity. Among all possible ssRNA oligonucleotides of a certain length, 1% of the oligonucleotides with the highest IL-12 scores are assigned to Group A; where as 1% of the oligonucleotides with the lowest IL-12 scores are assigned to Group B. The cut-off IL-12 score for Group A oligonucleotide is the threshold for high or maximal immunostimulatory activity; the cut-off IL-12 score for Group B oligonucleotide is the threshold for low or minimal immunostimulatory activity.

The IL-12 score thresholds for high/maximal and low/minimal immunostimulatory activity for 19mer ssRNA oligonucleotides are determined as follows:

A pool of all possible sequences of 19mer RNA oligonucleotides consists of $4^{19}=274,877,906,944$ oligonucleotides. The IFN-α score for every single RNA oligonucleotide in the pool is calculated using the 3mer-based algorithm. All $4^{19}$ oligonucleotides are ranked based on their calculated predicted IL-12 scores. The threshold for group A is determined to be $$8.4064 \times n + 66.958$$

(n=length of the ssRNA oligonucleotide, and n>9).

All ssRNA oligonucleotides with a calculated IL-12 score above the threshold value are grouped into Group A. The Group A threshold for 19mer ssRNA oligonucleotides is 226.68. Non-limiting examples of Group A 19mer ssRNA oligonucleotides include the following:

| Sequence (5' → 3') | SEQ ID NO: | Predicted IL-12 score |
|---|---|---|
| UUUAUAAGUUUGCUGGUGC | 226 | 243 |
| UUGUUUGUAUGGCUAUCCG | 227 | 231 |
| UUGCUCUCGUGUGUGGUAU | 228 | 263 |
| UUGCGUUGUUGGAGUGGUC | 229 | 310 |
| UGUGUUGUUGGCUCUACAA | 230 | 246 |
| UGUAGUGGUCGGUGGCCCC | 231 | 261 |
| UGUAGUGAAGUUGUGUCCG | 232 | 266 |
| UGAGUUGGUGGACUGUUUG | 233 | 262 |
| UCUCGUUGGUUACGUUACU | 234 | 237 |
| UAUGGUGUUUCGUAUAUGU | 235 | 283 |

The threshold for Group B oligonucleotides is determined to be:

$$0.0468 \times n^2 - 2.3103 \times n - 23.244$$

(n=length of the ssRNA oligonucleotide, and X>9)

All ssRNA oligonucleotides with a calculated IL-12 score below the threshold value are grouped into Group B. The Group B threshold for 19mer ssRNA oligonucleotide is −50.2449. Non-limiting examples of Group B 19mer oligonucleotide include the following:

| Sequence (5' → 3') | SEQ ID NO: | Predicted IL-12 score |
|---|---|---|
| GACCCAACACACACGGGCC | 236 | −101 |
| AAAACAAAACGGAACCCAG | 237 | −91 |
| AAAAACCAACCCAAGAUCU | 238 | −81 |
| UUAGGGCAAACCACCAGAC | 239 | −73 |
| CAGACCAACGGAACGCGCA | 240 | −72 |
| CGGCCCACCAACCCGGACU | 241 | −70 |
| CCCAAGAGAGACGAAACGC | 242 | −70 |
| UACCACAGGCCCAAACGGC | 243 | −68 |
| AUCCGAGAAACUACCACCA | 244 | −68 |
| CCCAAUAACACAAAGCCUA | 235 | −67 |

For ssRNA oligonucleotides between 3 and 9 nucleotides in length, the Group A and Group B threshold values are given below in Table 6:

TABLE 6

Threshold IL-12 scores for Group A and Group B oligonucleotides 3-9 nucleotides in length.

| ssRNA oligonucleotide length | The predicted IL-12 score (using the IL12 point score matrix) | |
| --- | --- | --- |
| | threshold for GROUP B ssRNA oligonucleotides | threshold for GROUP A ssRNA oligonucelotides |
| 3 | −5 | 13 |
| 4 | −15 | 50 |
| 5 | −19 | 66 |
| 6 | −28 | 93.53 |
| 7 | −31 | 107.77 |
| 8 | −34 | 121 |
| 9 | −36 | 121.98 |

REFERENCES

1 Schroder, M. and Bowie, A. G., TLR3 in antiviral immunity: key player or bystander? *Trends Immunol* 2005.
2 Hemmi, H., Takeuchi, O., Kawai, T., Kaisho, T., Sato, S., Sanjo, H., Matsumoto, M., Hoshino, K., Wagner, H., Takeda, K. and Akira, S., A Toll-like receptor recognizes bacterial DNA. *Nature* 2000. 408: 740-745.
3 Bauer, S., Kirschning, C. J., Hacker, H., Redecke, V., Hausmann, S., Akira, S., Wagner, H. and Lipford, G. B., Human TLR9 confers responsiveness to bacterial DNA via species-specific CpG motif recognition. *Proc Natl Acad Sci USA* 2001. 98: 9237-9242.
4 Krieg, A. M., Yi, A. K., Matson, S., Waldschmidt, T. J., Bishop, G. A., Teasdale, R., Koretzky, G. A. and Klinman, D. M., CpG motifs in bacterial DNA trigger direct B-cell activation. *Nature* 1995. 374: 546-549.
5 Heckelsmiller, K., Beck, S., Rall, K., Sipos, B., Schlamp, A., Tuma, E., Rothenfusser, S., Endres, S, and Hartmann, G., Combined dendritic cell- and CpG oligonucleotide-based immune therapy cures large murine tumors that resist chemotherapy. *Eur J Immunol* 2002. 32: 3235-3245.
6 Heckelsmiller, K., Rall, K., Beck, S., Schlamp, A., Seiderer, J., Jahrsdorfer, B., Krug, A., Rothenfusser, S., Endres, S, and Hartmann, G., Peritumoral CpG DNA elicits a coordinated response of CD8 T cells and innate effectors to cure established tumors in a murine colon carcinoma model. *J Immunol* 2002. 169: 3892-3899.
7 Krug, A., Towarowski, A., Britsch, S., Rothenfusser, S., Hornung, V., Bals, R., Giese, T., Engelmann, H., Endres, S., Krieg, A. M. and Hartmann, G., Toll-like receptor expression reveals CpG DNA as a unique microbial stimulus for plasmacytoid dendritic cells which synergizes with CD40 ligand to induce high amounts of IL-12. *Eur J Immunol* 2001. 31: 3026-3037.
8 Hornung, V., Rothenfusser, S., Britsch, S., Krug, A., Jahrsdorfer, B., Giese, T., Endres, S, and Hartmann, G., Quantitative expression of toll-like receptor 1-10 mRNA in cellular subsets of human peripheral blood mononuclear cells and sensitivity to CpG oligodeoxynucleotides. *J Immunol* 2002. 168: 4531-4537.
9 Choe, J., Kelker, M. S, and Wilson, I. A., Crystal structure of human toll-like receptor 3 (TLR3) ectodomain. *Science* 2005. 309: 581-585.
10 Hornung, V., Guenthner-Biller, M., Bourquin, C., Ablasser, A., Schlee, M., Uematsu, S., Noronha, A., Manoharan, M., Akira, S., de Fougerolles, A., Endres, S, and Hartmann, G., Sequence-specific potent induction of IFN-alpha by short interfering RNA in plasmacytoid dendritic cells through TLR7. *Nat Med* 2005. 11: 263-270.
11 Heil, F., Hemmi, H., Hochrein, H., Ampenberger, F., Kirschning, C., Akira, S., Lipford, G., Wagner, H. and Bauer, S., Species-specific recognition of single-stranded RNA via toll-like receptor 7 and 8. *Science* 2004. 303: 1526-1529.
12 Diebold, S. S., Kaisho, T., Hemmi, H., Akira, S, and Reis e Sousa, C., Innate antiviral responses by means of TLR7-mediated recognition of single-stranded RNA. *Science* 2004. 303: 1529-1531.
13 Hartmann, G., Weeratna, R. D., Ballas, Z. K., Payette, P., Blackwell, S., Suparto, I., Rasmussen, W. L., Waldschmidt, M., Sajuthi, D., Purcell, R. H., Davis, H. L. and Krieg, A. M., Delineation of a CpG phosphorothioate oligodeoxynucleotide for activating primate immune responses in vitro and in vivo. *J Immunol* 2000. 164: 1617-1624.
14 Hartmann, G. and Krieg, A. M., Mechanism and function of a newly identified CpG DNA motif in human primary B cells. *J Immunol* 2000. 164: 944-953.
15 Gorden, K. B., Gorski, K. S., Gibson, S. J., Kedl, R. M., Kieper, W. C., Qiu, X., Tomai, M. A., Alkan, S. S, and Vasilakos, J. P., Synthetic TLR agonists reveal functional differences between human TLR7 and TLR8. *J Immunol* 2005. 174: 1259-1268.
16 Sugiyama, T., Gursel, M., Takeshita, F., Coban, C., Conover, J., Kaisho, T., Akira, S., Klinman, D. M. and Ishii, K. J., CpG RNA: identification of novel single-stranded RNA that stimulates human CD14+CD11c+ monocytes. *J Immunol* 2005.174: 2273-2279.
17 Judge, A. D., Sood, V., Shaw, J. R., Fang, D., McClintock, K. and MacLachlan, I., Sequence-dependent stimulation of the mammalian innate immune response by synthetic siRNA. *Nat Biotechnol* 2005. 23: 457-462.
18 Sioud, M., Induction of inflammatory cytokines and interferon responses by double-stranded and single-stranded siRNAs is sequence-dependent and requires endosomal localization. *J Mol Biol* 2005. 348: 1079-1090.
19 Barchet, W., Krug, A., Cella, M., Newby, C., Fischer, J. A., Dzionek, A., Pekosz, A. and Colonna, M., Dendritic cells respond to influenza virus through TLR7- and PKR-independent pathways. *Eur J Immunol* 2005. 35: 236-242.
20 Koski, G. K., Kariko, K., Xu, S., Weissman, D., Cohen, P. A. and Czerniecki, B. J., Cutting edge: innate immune system discriminates between RNA containing bacterial versus eukaryotic structural features that prime for high-level IL-12 secretion by dendritic cells. *J Immunol* 2004.172: 3989-3993.
21 Scheel, B., Teufel, R., Probst, J., Carralot, J. P., Geginat, J., Radsak, M., Jarrossay, D., Wagner, H., Jung, G., Rammensee, H. G., Hoerr, I. and Pascolo, S., Toll-like receptor-dependent activation of several human blood cell types by protamine-condensed mRNA. *Eur J Immunol* 2005. 35: 1557-1566.
22 Scheel, B., Braedel, S., Probst, J., Carralot, J. P., Wagner, H., Schild, H., Jung, G., Rammensee, H. G. and Pascolo, S., Immunostimulating capacities of stabilized RNA molecules. *Eur J Immunol* 2004. 34: 537-547.
23 Rudolph, C., Plank, C., Lausier, J., Schillinger, U., Muller, R. H. and Rosenecker, J., Oligomers of the arginine-rich motif of the HIV-1 TAT protein are capable of transferring plasmid DNA into cells. *J Biol Chem* 2003. 278: 11411-11418.

24 Fuchs, S. M. and Raines, R. T., Pathway for polyarginine entry into mammalian cells. *Biochemistry* 2004. 43: 2438-2444.

25 Lochmann, D., Jauk, E. and Zimmer, A., Drug delivery of oligonucleotides by peptides. *Eur J Pharm Biopharm* 2004. 58: 237-251.

TABLE 1

Partially annealed ssRNA oligonucleotides Complete base pairing is indicated by normal letters, whereas mismatches are indicated by underlined letters. Table 1 discloses SEQ ID NOS 194, 446, 194, 449, 449, 446, 450, 450, 446, 451, 451, 446, 452, 452, and 446, respectively, in order of appearance.

| Name | Sequence |
|---|---|
| 9.2sense | 5'-AGCUUAACCUGUCCUUCAA-3' |
| 9.2antisense | 5'-UUGAAGGACAGGUUAAGCU-3' |
| 9.2duplex | 5'-AGCUUAACCUGUCCUUCAA-3'<br>\|\|\|\|\|\|\|\|\|\|\|\|\|\|\|\|\|\|\|<br>3'-UCGAAUUGGACAGGAAGUU-5' |
| 9.2R | 5'-AGCUUAACCUGUCCUU-3' |
| 9.2R+9.2antisense | 5'-AGCUUAACCUGUCCUU-3'<br>\|\|\|\|\|\|\|\|\|\|\|\|\|\|\|\|<br>3'-UCGAAUUGGACAGGAA<u>GUU</u>-5' |
| 9.2L | 5'-UUAACCUGUCCUUCAA-3' |
| 9.2L+9.2antisense | 5'-UUAACCUGUCCUUCAA-3'<br>\|\|\|\|\|\|\|\|\|\|\|\|\|\|\|\|<br>3'-<u>UCG</u>AAUUGGACAGGAAGUU-5' |
| 9.2A | 5'-AGCUUAACCUGU-3' |
| 9.2A+9.2as | 5'-AGCUUAACCUGU-3'<br>\|\|\|\|\|\|\|\|\|\|\|\|<br>3'-UCGAAUUGGACA<u>GGAAGUU</u>-5' |
| 9.2B | 5'-ACCUGUCCUUCA-3' |
| 9.2B+9.2as | 5'-ACCUGUCCUUCA-3'<br>\|\|\|\|\|\|\|\|\|\|\|\|<br>3'-<u>UCGAAUU</u>GGACAGGAAGUU-5' |

TABLE 2

Self complementary ssRNA oligonucleotides Complete base pairing is indicated by normal letters, whereas mismatches are indicated by underlined letters. Table 2 discloses SEQ ID NOS 453, 454, 454, 455, 455, 456, 456, 457, 457, 458, 458, 459, and 459, respectively, in order of appearance.

| Name | Sequence |
|---|---|
| RNA-P20 | 5'-UUGAAGGACAUGUCCUUCAA-3'<br>\|\|\|\|\|\|\|\|\|\|\|\|\|\|\|\|\|\|\|\|<br>3'-AACUUCCUGUACAGGAAGUU-5' |
| RNA-P20-1M | 5'-U<u>G</u>GAAGGACAUGUCCUUC<u>A</u>A-3'<br>\| \|\|\|\|\|\|\|\|\|\|\|\|\|\|\|\|\|\| \|<br>3'-<u>A</u>ACUUCCUGUACAGGAAG<u>G</u>U-5' |
| RNA-P20-2M | 5'-U<u>GU</u>AAGGACAUGUCCUUC<u>A</u>A-3'<br>\| \|\|\|\|\|\|\|\|\|\|\|\|\|\|\|\|\| \|<br>3'-<u>A</u>ACUUCCUGUACAGGA<u>AUG</u>U-5' |
| RNA-P20-3'M | 5'-U<u>GUC</u>AGGACAUGUCCU<u>UCA</u>A-3'<br>\| \|\|\|\|\|\|\|\|\|\|\|\|\| \|<br>3'-<u>A</u>ACUUCCUGUACAGGA<u>CUG</u>U-5' |
| RNA-P20-5'M | 5'-U<u>G</u>UCCUGACAUGU<u>CC</u>UUC<u>A</u>A-3'<br>\| \|\|\|\|\|\|\|\| \|\|\|\|\| \|<br>3'-<u>A</u>ACUUCCUGUACAG<u>U</u>CCUGU-5' |
| RNA-P20-6M | 5'-UGUCCUUACAUGUCCUUCAA-3'<br>\| \|\|\|\|\|\| \|<br>3'-<u>A</u>ACUUCCUGUACA<u>U</u>UCCUGU-5' |
| RNA-M20 | 5'-UGUCCUUCAUGUCCUUCAA-3'<br>\| \|\| \|<br>5'-<u>A</u>ACUUCCUGU<u>AA</u>CUUCCUGU-3' |

TABLE 3

193 ssRNA oligonucleotide library covering all possible 256 4mer motifs

| Name | Sequence |
|---|---|
| ANP-Oligo 001 | AAAAAAAAAAAAAAAAA (SEQ ID NO: 1) |
| ANP-Oligo 002 | AAAAAAAACAAAAAAAA (SEQ ID NO: 2) |
| ANP-Oligo 003 | AAAAAAAAGAAAAAAAA (SEQ ID NO: 3) |
| ANP-Oligo 004 | AAAAAAAAUAAAAAAAA (SEQ ID NO: 4) |
| ANP-Oligo 005 | AAAAAAAACCAAAAAAA (SEQ ID NO: 5) |
| ANP-Oligo 006 | AAAAAAAACGAAAAAAA (SEQ ID NO: 6) |
| ANP-Oligo 007 | AAAAAAAACUAAAAAAA (SEQ ID NO: 7) |
| ANP-Oligo 008 | AAAAAAAAGCAAAAAAA (SEQ ID NO: 8) |
| ANP-Oligo 009 | AAAAAAAAGGAAAAAAA (SEQ ID NO: 9) |
| ANP-Oligo 010 | AAAAAAAAGUAAAAAAA (SEQ ID NO: 10) |
| ANP-Oligo 011 | AAAAAAAAUCAAAAAAA (SEQ ID NO: 11) |
| ANP-Oligo 012 | AAAAAAAAUGAAAAAAA (SEQ ID NO: 12) |
| ANP-Oligo 013 | AAAAAAAAUUAAAAAAA (SEQ ID NO: 13) |
| ANP-Oligo 014 | AAAAAAAACACAAAAAA (SEQ ID NO: 14) |
| ANP-Oligo 015 | AAAAAAAACAGAAAAAA (SEQ ID NO: 15) |
| ANP-Oligo 016 | AAAAAAAACAUAAAAAA (SEQ ID NO: 16) |
| ANP-Oligo 017 | AAAAAAAACCCAAAAAA (SEQ ID NO: 17) |
| ANP-Oligo 018 | AAAAAAAACCGAAAAAA (SEQ ID NO: 18) |
| ANP-Oligo 019 | AAAAAAAACCUAAAAAA (SEQ ID NO: 19) |
| ANP-Oligo 020 | AAAAAAAACGCAAAAAA (SEQ ID NO: 20) |
| ANP-Oligo 021 | AAAAAAAACGGAAAAAA (SEQ ID NO: 21) |
| ANP-Oligo 022 | AAAAAAAACGUAAAAAA (SEQ ID NO: 22) |
| ANP-Oligo 023 | AAAAAAAACUCAAAAAA (SEQ ID NO: 23) |
| ANP-Oligo 024 | AAAAAAAACUGAAAAAA (SEQ ID NO: 24) |
| ANP-Oligo 025 | AAAAAAAACUUAAAAAA (SEQ ID NO: 25) |
| ANP-Oligo 026 | AAAAAAAAGACAAAAAA (SEQ ID NO: 26) |
| ANP-Oligo 027 | AAAAAAAAGAGAAAAAA (SEQ ID NO: 27) |

TABLE 3-continued 193 ssRNA oligonucleotide library covering all possible 256 4mer motifs

| Name | Sequence |
|---|---|
| ANP-Oligo 028 | AAAAAAAAGAUAAAAAAAA (SEQ ID NO: 28) |
| ANP-Oligo 029 | AAAAAAAAGCCAAAAAAAA (SEQ ID NO: 29) |
| ANP-Oligo 030 | AAAAAAAAGCGAAAAAAAA (SEQ ID NO: 30) |
| ANP-Oligo 031 | AAAAAAAAGCUAAAAAAAA (SEQ ID NO: 31) |
| ANP-Oligo 032 | AAAAAAAAGGCAAAAAAAA (SEQ ID NO: 32) |
| ANP-Oligo 033 | AAAAAAAAGGGAAAAAAAA (SEQ ID NO: 33) |
| ANP-Oligo 034 | AAAAAAAAGGUAAAAAAAA (SEQ ID NO: 34) |
| ANP-Oligo 035 | AAAAAAAAGUCAAAAAAAA (SEQ ID NO: 35) |
| ANP-Oligo 036 | AAAAAAAAGUGAAAAAAAA (SEQ ID NO: 36) |
| ANP-Oligo 037 | AAAAAAAAGUUAAAAAAAA (SEQ ID NO: 37) |
| ANP-Oligo 038 | AAAAAAAAUACAAAAAAAA (SEQ ID NO: 38) |
| ANP-Oligo 039 | AAAAAAAAUAGAAAAAAAA (SEQ ID NO: 39) |
| ANP-Oligo 040 | AAAAAAAAUAUAAAAAAAA (SEQ ID NO: 40) |
| ANP-Oligo 041 | AAAAAAAAUCCAAAAAAAA (SEQ ID NO: 41) |
| ANP-Oligo 042 | AAAAAAAAUCGAAAAAAAA (SEQ ID NO: 42) |
| ANP-Oligo 043 | AAAAAAAAUCUAAAAAAAA (SEQ ID NO: 43) |
| ANP-Oligo 044 | AAAAAAAAUGCAAAAAAAA (SEQ ID NO: 44) |
| ANP-Oligo 045 | AAAAAAAAUGGAAAAAAAA (SEQ ID NO: 45) |
| ANP-Oligo 046 | AAAAAAAAUGUAAAAAAAA (SEQ ID NO: 46) |
| ANP-Oligo 047 | AAAAAAAAUUCAAAAAAAA (SEQ ID NO: 47) |
| ANP-Oligo 048 | AAAAAAAAUUGAAAAAAAA (SEQ ID NO: 48) |
| ANP-Oligo 049 | AAAAAAAAUUUAAAAAAAA (SEQ ID NO: 49) |
| ANP-Oligo 050 | AAAAAAACAACAAAAAAAA (SEQ ID NO: 50) |
| ANP-Oligo 051 | AAAAAAACAAGAAAAAAAA (SEQ ID NO: 51) |
| ANP-Oligo 052 | AAAAAAACAAUAAAAAAAA (SEQ ID NO: 52) |
| ANP-Oligo 053 | AAAAAAACACCAAAAAAAA (SEQ ID NO: 53) |
| ANP-Oligo 054 | AAAAAAACACGAAAAAAAA (SEQ ID NO: 54) |
| ANP-Oligo 055 | AAAAAAACACUAAAAAAAA (SEQ ID NO: 55) |
| ANP-Oligo 056 | AAAAAAACAGCAAAAAAAA (SEQ ID NO: 56) |
| ANP-Oligo 057 | AAAAAAACAGGAAAAAAAA (SEQ ID NO: 57) |
| ANP-Oligo 058 | AAAAAAACAGUAAAAAAAA (SEQ ID NO: 58) |
| ANP-Oligo 059 | AAAAAAACAUCAAAAAAAA (SEQ ID NO: 59) |
| ANP-Oligo 060 | AAAAAAACAUGAAAAAAAA (SEQ ID NO: 60) |
| ANP-Oligo 061 | AAAAAAACAUUAAAAAAAA (SEQ ID NO: 61) |
| ANP-Oligo 062 | AAAAAAACCACAAAAAAAA (SEQ ID NO: 62) |
| ANP-Oligo 063 | AAAAAAACCAGAAAAAAAA (SEQ ID NO: 63) |
| ANP-Oligo 064 | AAAAAAACCAUAAAAAAAA (SEQ ID NO: 64) |
| ANP-Oligo 065 | AAAAAAACCCCAAAAAAAA (SEQ ID NO: 65) |
| ANP-Oligo 066 | AAAAAAACCCGAAAAAAAA (SEQ ID NO: 66) |
| ANP-Oligo 067 | AAAAAAACCCUAAAAAAAA (SEQ ID NO: 67) |
| ANP-Oligo 068 | AAAAAAACCGCAAAAAA4AA (SEQ ID NO: 68) |
| ANP-Oligo 069 | AAAAAAACCGGAAAAAAAA (SEQ ID NO: 69) |
| ANP-Oligo 070 | AAAAAAACCGUAAAAAAAA (SEQ ID NO: 70) |
| ANP-Oligo 071 | AAAAAAACCUCAAAAAAAA (SEQ ID NO: 71) |
| ANP-Oligo 072 | AAAAAAACCUGAAAAAAAA (SEQ ID NO: 72) |
| ANP-Oligo 073 | AAAAAAACCUUAAAAAAAA (SEQ ID NO: 73) |
| ANP-Oligo 074 | AAAAAAACGACAAAAAAAA (SEQ ID NO: 74) |
| ANP-Oligo 075 | AAAAAAACGAGAAAAAAAA (SEQ ID NO: 75) |
| ANP-Oligo 076 | AAAAAAACGAUAAAAAAAA (SEQ ID NO: 76) |
| ANP-Oligo 077 | AAAAAAACGCCAAAAAAAA (SEQ ID NO: 77) |
| ANP-Oligo 078 | AAAAAAACGCGAAAAAAAA (SEQ ID NO: 78) |
| ANP-Oligo 079 | AAAAAAACGCUAAAAAAAA (SEQ ID NO: 79) |
| ANP-Oligo 080 | AAAAAAACGGCAAAAAAAA (SEQ ID NO: 80) |
| ANP-Oligo 081 | AAAAAAACGGGAAAAAAAA (SEQ ID NO: 81) |
| ANP-Oligo 082 | AAAAAAACGGUAAAAAAAA (SEQ ID NO: 82) |
| ANP-Oligo 083 | AAAAAAACGUCAAAAAAAA (SEQ ID NO: 83) |
| ANP-Oligo 084 | AAAAAAACGUGAAAAAAAA (SEQ ID NO: 84) |
| ANP-Oligo 085 | AAAAAAACGUUAAAAAAAA (SEQ ID NO: 85) |
| ANP-Oligo 086 | AAAAAAACUACAAAAAAAA (SEQ ID NO: 86) |
| ANP-Oligo 087 | AAAAAAACUAGAAAAAAAA (SEQ ID NO: 87) |
| ANP-Oligo 088 | AAAAAAACUAUAAAAAAAA (SEQ ID NO: 88) |
| ANP-Oligo 089 | AAAAAAACUCCAAAAAAAA (SEQ ID NO: 89) |
| ANP-Oligo 090 | AAAAAAACUCGAAAAAAAA (SEQ ID NO: 90) |
| ANP-Oligo 091 | AAAAAAACUCUAAAAAAAA (SEQ ID NO: 91) |
| ANP-Oligo 092 | AAAAAAACUGCAAAAAAAA (SEQ ID NO: 92) |
| ANP-Oligo 093 | AAAAAAACUGGAAAAAAAA (SEQ ID NO: 93) |
| ANP-Oligo 094 | AAAAAAACUGUAAAAAAAA (SEQ ID NO: 94) |
| ANP-Oligo 095 | AAAAAAACUUCAAAAAAAA (SEQ ID NO: 95) |
| ANP-Oligo 096 | AAAAAAACUUGAAAAAAAA (SEQ ID NO: 96) |
| ANP-Oligo 097 | AAAAAAACUUUAAAAAAAA (SEQ ID NO: 97) |
| ANP-Oligo 098 | AAAAAAAGAACAAAAAAAA (SEQ ID NO: 98) |
| ANP-Oligo 099 | AAAAAAAGAAGAAAAAAAA (SEQ ID NO: 99) |
| ANP-Oligo 100 | AAAAAAAGAAUAAAAAAAA (SEQ ID NO: 100) |
| ANP-Oligo 101 | AAAAAAAGACCAAAAAAAA (SEQ ID NO: 101) |
| ANP-Oligo 102 | AAAAAAAGACGAAAAAAAA (SEQ ID NO: 102) |

TABLE 3-continued 193 ssRNA oligonucleotide library covering all possible 256 4mer motifs

| Name | Sequence |
|---|---|
| ANP-Oligo 103 | AAAAAAAGACUAAAAAAAA (SEQ ID NO: 103) |
| ANP-Oligo 104 | AAAAAAAGAGCAAAAAAAA (SEQ ID NO: 104) |
| ANP-Oligo 105 | AAAAAAAGAGGAAAAAAAA (SEQ ID NO: 105) |
| ANP-Oligo 106 | AAAAAAAGAGUAAAAAAAA (SEQ ID NO: 106) |
| ANP-Oligo 107 | AAAAAAAGAUCAAAAAAAA (SEQ ID NO: 107) |
| ANP-Oligo 108 | AAAAAAAGAUGAAAAAAAA (SEQ ID NO: 108) |
| ANP-Oligo 109 | AAAAAAAGAUUAAAAAAAA (SEQ ID NO: 109) |
| ANP-Oligo 110 | AAAAAAAGCACAAAAAAAA (SEQ ID NO: 110) |
| ANP-Oligo 111 | AAAAAAAGCAGAAAAAAAA (SEQ ID NO: 111) |
| ANP-Oligo 112 | AAAAAAAGCAUAAAAAAAA (SEQ ID NO: 112) |
| ANP-Oligo 113 | AAAAAAAGCCCAAAAAAAA (SEQ ID NO: 113) |
| ANP-Oligo 114 | AAAAAAAGCCGAAAAAAAA (SEQ ID NO: 114) |
| ANP-Oligo 115 | AAAAAAAGCCUAAAAAAAA (SEQ ID NO: 115) |
| ANP-Oligo 116 | AAAAAAAGCGCAAAAAAAA (SEQ ID NO: 116) |
| ANP-Oligo 117 | AAAAAAAGCGGAAAAAAAA (SEQ ID NO: 117) |
| ANP-Oligo 118 | AAAAAAAGCGUAAAAAAAA (SEQ ID NO: 118) |
| ANP-Oligo 119 | AAAAAAAGCUCAAAAAAAA (SEQ ID NO: 119) |
| ANP-Oligo 120 | AAAAAAAGCUGAAAAAAAA (SEQ ID NO: 120) |
| ANP-Oligo 121 | AAAAAAAGCUUAAAAAAAA (SEQ ID NO: 121) |
| ANP-Oligo 122 | AAAAAAAGGACAAAAAAAA (SEQ ID NO: 122) |
| ANP-Oligo 123 | AAAAAAAGGAGAAAAAAAA (SEQ ID NO: 123) |
| ANP-Oligo 124 | AAAAAAAGGAUAAAAAAAA (SEQ ID NO: 124) |
| ANP-Oligo 125 | AAAAAAAGGCCAAAAAAAA (SEQ ID NO: 125) |
| ANP-Oligo 126 | AAAAAAAGGCGAAAAAAAA (SEQ ID NO: 126) |
| ANP-Oligo 127 | AAAAAAAGGCUAAAAAAAA (SEQ ID NO: 127) |
| ANP-Oligo 128 | AAAAAAAGGGCAAAAAAAA (SEQ ID NO: 128) |
| ANP-Oligo 129 | AAAAAAAGGGGAAAAAAAA (SEQ ID NO: 129) |
| ANP-Oligo 130 | AAAAAAAGGGUAAAAAAAA (SEQ ID NO: 130) |
| ANP-Oligo 131 | AAAAAAAGGUCAAAAAAAA (SEQ ID NO: 131) |
| ANP-Oligo 132 | AAAAAAAGGUGAAAAAAAA (SEQ ID NO: 132) |
| ANP-Oligo 133 | AAAAAAAGGUUAAAAAAAA (SEQ ID NO: 133) |
| ANP-Oligo 134 | AAAAAAAGUACAAAAAAAA (SEQ ID NO: 134) |
| ANP-Oligo 135 | AAAAAAAGUAGAAAAAAAA (SEQ ID NO: 135) |
| ANP-Oligo 136 | AAAAAAAGUAUAAAAAAAA (SEQ ID NO: 136) |
| ANP-Oligo 137 | AAAAAAAGUCCAAAAAAAA (SEQ ID NO: 137) |
| ANP-Oligo 138 | AAAAAAAGUCGAAAAAAAA (SEQ ID NO: 138) |
| ANP-Oligo 139 | AAAAAAAGUCUAAAAAAAA (SEQ ID NO: 139) |
| ANP-Oligo 140 | AAAAAAAGUGCAAAAAAAA (SEQ ID NO: 140) |
| ANP-Oligo 141 | AAAAAAAGUGGAAAAAAAA (SEQ ID NO: 141) |
| ANP-Oligo 142 | AAAAAAAGUGUAAAAAAAA (SEQ ID NO: 142) |
| ANP-Oligo 143 | AAAAAAAGUUCAAAAAAAA (SEQ ID NO: 143) |
| ANP-Oligo 144 | AAAAAAAGUUGAAAAAAAA (SEQ ID NO: 144) |
| ANP-Oligo 145 | AAAAAAAGUUUAAAAAAAA (SEQ ID NO: 145) |
| ANP-Oligo 146 | AAAAAAAUAACAAAAAAAA (SEQ ID NO: 146) |
| ANP-Oligo 147 | AAAAAAAUAAGAAAAAAAA (SEQ ID NO: 147) |
| ANP-Oligo 148 | AAAAAAAUAAUAAAAAAAA (SEQ ID NO: 148) |
| ANP-Oligo 149 | AAAAAAAUACCAAAAAAAA (SEQ ID NO: 149) |
| ANP-Oligo 150 | AAAAAAAUACGAAAAAAAA (SEQ ID NO: 150) |
| ANP-Oligo 151 | AAAAAAAUACUAAAAAAAA (SEQ ID NO: 151) |
| ANP-Oligo 152 | AAAAAAAUAGCAAAAAAAA (SEQ ID NO: 152) |
| ANP-Oligo 153 | AAAAAAAUAGGAAAAAAAA (SEQ ID NO: 153) |
| ANP-Oligo 154 | AAAAAAAUAGUAAAAAAAA (SEQ ID NO: 154) |
| ANP-Oligo 155 | AAAAAAAUAUCAAAAAAAA (SEQ ID NO: 155) |
| ANP-Oligo 156 | AAAAAAAUAUGAAAAAAAA (SEQ ID NO: 156) |
| ANP-Oligo 157 | AAAAAAAUAUUAAAAAAAA (SEQ ID NO: 157) |
| ANP-Oligo 158 | AAAAAAAUCACAAAAAAAA (SEQ ID NO: 158) |
| ANP-Oligo 159 | AAAAAAAUCAGAAAAAAAA (SEQ ID NO: 159) |
| ANP-Oligo 160 | AAAAAAAUCAUAAAAAAAA (SEQ ID NO: 160) |
| ANP-Oligo 161 | AAAAAAAUCCCAAAAAAAA (SEQ ID NO: 161) |
| ANP-Oligo 162 | AAAAAAAUCCGAAAAAAAA (SEQ ID NO: 162) |
| ANP-Oligo 163 | AAAAAAAUCCUAAAAAAAA (SEQ ID NO: 163) |
| ANP-Oligo 164 | AAAAAAAUCGCAAAAAAAA (SEQ ID NO: 164) |
| ANP-Oligo 165 | AAAAAAAUCGGAAAAAAAA (SEQ ID NO: 165) |
| ANP-Oligo 166 | AAAAAAAUCGUAAAAAAAA (SEQ ID NO: 166) |
| ANP-Oligo 167 | AAAAAAAUCUCAAAAAAAA (SEQ ID NO: 167) |
| ANP-Oligo 168 | AAAAAAAUCUGAAAAAAAA (SEQ ID NO: 168) |
| ANP-Oligo 169 | AAAAAAAUCUUAAAAAAAA (SEQ ID NO: 169) |
| ANP-Oligo 170 | AAAAAAAUGACAAAAAAAA (SEQ ID NO: 170) |
| ANP-Oligo 171 | AAAAAAAUGAGAAAAAAAA (SEQ ID NO: 171) |
| ANP-Oligo 172 | AAAAAAAUGAUAAAAAAAA (SEQ ID NO: 172) |
| ANP-Oligo 173 | AAAAAAAUGCCAAAAAAAA (SEQ ID NO: 173) |
| ANP-Oligo 174 | AAAAAAAUGCGAAAAAAAA (SEQ ID NO: 174) |
| ANP-Oligo 175 | AAAAAAAUGCUAAAAAAAA (SEQ ID NO: 175) |
| ANP-Oligo 176 | AAAAAAAUGGCAAAAAAAA (SEQ ID NO: 176) |
| ANP-Oligo 177 | AAAAAAAUGGGAAAAAAAA (SEQ ID NO: 177) |

TABLE 3-continued

193 ssRNA oligonucleotide library covering all possible 256 4mer motifs

| Name | Sequence |
|---|---|
| ANP-Oligo 178 | AAAAAAAUGGUAAAAAAAA (SEQ ID NO: 178) |
| ANP-Oligo 179 | AAAAAAAUGUCAAAAAAAA (SEQ ID NO: 179) |
| ANP-Oligo 180 | AAAAAAAUGUGAAAAAAAA (SEQ ID NO: 180) |
| ANP-Oligo 181 | AAAAAAAUGUUAAAAAAAA (SEQ ID NO: 181) |
| ANP-Oligo 182 | AAAAAAAUUACAAAAAAAA (SEQ ID NO: 182) |
| ANP-Oligo 183 | AAAAAAAUUAGAAAAAAAA (SEQ ID NO: 183) |
| ANP-Oligo 184 | AAAAAAAUUAUAAAAAAAA (SEQ ID NO: 184) |
| ANP-Oligo 185 | AAAAAAAUUCCAAAAAAAA (SEQ ID NO: 185) |
| ANP-Oligo 186 | AAAAAAAUUCGAAAAAAAA (SEQ ID NO: 186) |
| ANP-Oligo 187 | AAAAAAAUUCUAAAAAAAA (SEQ ID NO: 187) |
| ANP-Oligo 188 | AAAAAAAUUGCAAAAAAAA (SEQ ID NO: 188) |
| ANP-Oligo 189 | AAAAAAAUUGGAAAAAAAA (SEQ ID NO: 189) |
| ANP-Oligo 190 | AAAAAAAUUGUAAAAAAAA (SEQ ID NO: 190) |
| ANP-Oligo 191 | AAAAAAAUUUCAAAAAAAA (SEQ ID NO: 191) |
| ANP-Oligo 192 | AAAAAAAUUUGAAAAAAAA (SEQ ID NO: 192) |
| ANP-Oligo 193 | AAAAAAAUUUUAAAAAAAA (SEQ ID NO: 193) |

TABLE 4

Adjusted IL-12 indices of the 193 ssRNA oligonucleotide library

| Name | Adjusted Sequence | IL-12 index Mean | SEM | |
|---|---|---|---|---|
| ANP-Oligo 018 | AAAAAAAACCGAAAAAAAA | −0.68 | 0.12 | (SEQ ID NO: 18) |
| ANP-Oligo 053 | AAAAAAACACCAAAAAAAA | −0.67 | 0.11 | (SEQ ID NO: 53) |
| ANP-Oligo 020 | AAAAAAAACGCAAAAAAAA | −0.66 | 0.12 | (SEQ ID NO: 20) |
| ANP-Oligo 051 | AAAAAAACAAGAAAAAAAA | −0.66 | 0.11 | (SEQ ID NO: 51) |
| ANP-Oligo 062 | AAAAAAACCACAAAAAAAA | −0.66 | 0.11 | (SEQ ID NO: 62) |
| ANP-Oligo 029 | AAAAAAAAGCCAAAAAAAA | −0.66 | 0.11 | (SEQ ID NO: 29) |
| ANP-Oligo 009 | AAAAAAAAGGAAAAAAAAA | −0.66 | 0.12 | (SEQ ID NO: 9) |
| ANP-Oligo 017 | AAAAAAAACCCAAAAAAAA | −0.66 | 0.12 | (SEQ ID NO: 17) |
| ANP-Oligo 075 | AAAAAAACGAGAAAAAAAA | −0.65 | 0.11 | (SEQ ID NO: 75) |
| ANP-Oligo 015 | AAAAAAAACAGAAAAAAAA | −0.65 | 0.12 | (SEQ ID NO: 15) |
| ANP-Oligo 054 | AAAAAAACACGAAAAAAAA | −0.65 | 0.11 | (SEQ ID NO: 54) |
| ANP-Oligo 080 | AAAAAAACGGCAAAAAAAA | −0.65 | 0.11 | (SEQ ID NO: 80) |
| ANP-Oligo 102 | AAAAAAAGACGAAAAAAAA | −0.64 | 0.09 | (SEQ ID NO: 102) |
| ANP-Oligo 042 | AAAAAAAAUCGAAAAAAAA | −0.64 | 0.1 | (SEQ ID NO: 42) |
| ANP-Oligo 050 | AAAAAAACAACAAAAAAAA | −0.64 | 0.11 | (SEQ ID NO: 50) |
| ANP-Oligo 069 | AAAAAAACCGGAAAAAAAA | −0.64 | 0.1 | (SEQ ID NO: 69) |
| ANP-Oligo 128 | AAAAAAAGGGCAAAAAAAA | −0.64 | 0.1 | (SEQ ID NO: 128) |
| ANP-Oligo 014 | AAAAAAAACACAAAAAAAA | −0.64 | 0.11 | (SEQ ID NO: 14) |
| ANP-Oligo 021 | AAAAAAAACGGAAAAAAAA | −0.63 | 0.11 | (SEQ ID NO: 21) |
| ANP-Oligo 003 | AAAAAAAAGAAAAAAAAAA | −0.63 | 0.11 | (SEQ ID NO: 3) |
| ANP-Oligo 117 | AAAAAAAGCGGAAAAAAAA | −0.63 | 0.09 | (SEQ ID NO: 117) |
| ANP-Oligo 006 | AAAAAAAACGAAAAAAAAA | −0.63 | 0.12 | (SEQ ID NO: 6) |
| ANP-Oligo 081 | AAAAAAACGGGAAAAAAAA | −0.63 | 0.1 | (SEQ ID NO: 81) |

TABLE 4-continued

Adjusted IL-12 indices of the 193 ssRNA oligonucleotide library

| Name | Adjusted Sequence | IL-12 index Mean | SEM | |
|---|---|---|---|---|
| ANP-Oligo 105 | AAAAAAAGAGGAAAAAAAA | −0.62 | 0.09 | (SEQ ID NO: 105) |
| ANP-Oligo 066 | AAAAAAACCCGAAAAAAAA | −0.62 | 0.11 | (SEQ ID NO: 66) |
| ANP-Oligo 027 | AAAAAAAAGAGAAAAAAAA | −0.62 | 0.1 | (SEQ ID NO: 27) |
| ANP-Oligo 032 | AAAAAAAAGGCAAAAAAAA | −0.62 | 0.1 | (SEQ ID NO: 32) |
| ANP-Oligo 077 | AAAAAAACGCCAAAAAAAA | −0.62 | 0.1 | (SEQ ID NO: 77) |
| ANP-Oligo 005 | AAAAAAAACCAAAAAAAAA | −0.62 | 0.12 | (SEQ ID NO: 5) |
| ANP-Oligo 104 | AAAAAAAGAGCAAAAAAAA | −0.61 | 0.08 | (SEQ ID NO: 104) |
| ANP-Oligo 099 | AAAAAAAGAAGAAAAAAAA | −0.61 | 0.1 | (SEQ ID NO: 99) |
| ANP-Oligo 008 | AAAAAAAAGCAAAAAAAAA | −0.61 | 0.12 | (SEQ ID NO: 8) |
| ANP-Oligo 057 | AAAAAAACAGGAAAAAAAA | −0.6 | 0.1 | (SEQ ID NO: 57) |
| ANP-Oligo 101 | AAAAAAAGACCAAAAAAAA | −0.6 | 0.08 | (SEQ ID NO: 101) |
| ANP-Oligo 026 | AAAAAAAAGACAAAAAAAA | −0.6 | 0.1 | (SEQ ID NO: 26) |
| ANP-Oligo 074 | AAAAAAACGACAAAAAAAA | −0.6 | 0.09 | (SEQ ID NO: 74) |
| ANP-Oligo 098 | AAAAAAAGAACAAAAAAAA | −0.6 | 0.1 | (SEQ ID NO: 98) |
| ANP-Oligo 030 | AAAAAAAAGCGAAAAAAAA | −0.6 | 0.1 | (SEQ ID NO: 30) |
| ANP-Oligo 033 | AAAAAAAAGGGAAAAAAAA | −0.59 | 0.09 | (SEQ ID NO: 33) |
| ANP-Oligo 065 | AAAAAAACCCCAAAAAAAA | −0.59 | 0.1 | (SEQ ID NO: 65) |
| ANP-Oligo 078 | AAAAAAACGCGAAAAAAAA | −0.59 | 0.1 | (SEQ ID NO: 78) |
| ANP-Oligo 114 | AAAAAAAGCCGAAAAAAAA | −0.58 | 0.08 | (SEQ ID NO: 114) |
| ANP-Oligo 116 | AAAAAAAGCGCAAAAAAAA | −0.58 | 0.07 | (SEQ ID NO: 116) |
| ANP-Oligo 110 | AAAAAAAGCACAAAAAAAA | −0.58 | 0.09 | (SEQ ID NO: 110) |
| ANP-Oligo 002 | AAAAAAAACAAAAAAAAAA | −0.57 | 0.12 | (SEQ ID NO: 2) |
| ANP-Oligo 063 | AAAAAAACCAGAAAAAAAA | −0.57 | 0.09 | (SEQ ID NO: 63) |
| ANP-Oligo 068 | AAAAAAACCGCAAAAAAAA | −0.56 | 0.08 | (SEQ ID NO: 68) |
| ANP-Oligo 007 | AAAAAAAACUAAAAAAAAA | −0.56 | 0.11 | (SEQ ID NO: 7) |
| ANP-Oligo 071 | AAAAAAACCUCAAAAAAAA | −0.56 | 0.09 | (SEQ ID NO: 71) |
| ANP-Oligo 056 | AAAAAAACAGCAAAAAAAA | −0.54 | 0.11 | (SEQ ID NO: 56) |
| ANP-Oligo 126 | AAAAAAAGGCGAAAAAAAA | −0.54 | 0.07 | (SEQ ID NO: 126) |
| ANP-Oligo 125 | AAAAAAAGGCCAAAAAAAA | −0.54 | 0.08 | (SEQ ID NO: 125) |
| ANP-Oligo 113 | AAAAAAAGCCCAAAAAAAA | −0.54 | 0.06 | (SEQ ID NO: 113) |
| ANP-Oligo 090 | AAAAAAACUCGAAAAAAAA | −0.54 | 0.07 | (SEQ ID NO: 90) |
| ANP-Oligo 055 | AAAAAAACACUAAAAAAAA | −0.53 | 0.11 | (SEQ ID NO: 55) |
| ANP-Oligo 123 | AAAAAAAGGAGAAAAAAAA | −0.51 | 0.08 | (SEQ ID NO: 123) |
| ANP-Oligo 019 | AAAAAAAACCUAAAAAAAA | −0.51 | 0.14 | (SEQ ID NO: 19) |
| ANP-Oligo 129 | AAAAAAAGGGGAAAAAAAA | −0.51 | 0.08 | (SEQ ID NO: 129) |
| ANP-Oligo 072 | AAAAAAACCUGAAAAAAAA | −0.51 | 0.07 | (SEQ ID NO: 72) |
| ANP-Oligo 162 | AAAAAAAUCCGAAAAAAAA | −0.5 | 0.07 | (SEQ ID NO: 162) |

TABLE 4-continued

Adjusted IL-12 indices of the 193 ssRNA oligonucleotide library

| Name | Adjusted Sequence | IL-12 index Mean | SEM | |
|---|---|---|---|---|
| ANP-Oligo 119 | AAAAAAAGCUCAAAAAAAA | −0.48 | 0.07 | (SEQ ID NO: 119) |
| ANP-Oligo 001 | AAAAAAAAAAAAAAAAAAA | −0.48 | 0.12 | (SEQ ID NO: 1) |
| ANP-Oligo 059 | AAAAAAACAUCAAAAAAAA | −0.48 | 0.07 | (SEQ ID NO: 59) |
| ANP-Oligo 024 | AAAAAAAACUGAAAAAAAA | −0.48 | 0.1 | (SEQ ID NO: 24) |
| ANP-Oligo 041 | AAAAAAAAUCCAAAAAAAA | −0.48 | 0.15 | (SEQ ID NO: 41) |
| ANP-Oligo 086 | AAAAAAACUACAAAAAAAA | −0.46 | 0.07 | (SEQ ID NO: 86) |
| ANP-Oligo 060 | AAAAAAACUAGAAAAAAAA | −0.46 | 0.08 | (SEQ ID NO: 60) |
| ANP-Oligo 047 | AAAAAAAAUUCAAAAAAAA | −0.45 | 0.13 | (SEQ ID NO: 47) |
| ANP-Oligo 130 | AAAAAAAGGGUAAAAAAAA | −0.44 | 0.08 | (SEQ ID NO: 130) |
| ANP-Oligo 122 | AAAAAAAGGACAAAAAAAA | −0.43 | 0.06 | (SEQ ID NO: 122) |
| ANP-Oligo 011 | AAAAAAAAUCAAAAAAAAA | −0.43 | 0.1 | (SEQ ID NO: 11) |
| ANP-Oligo 161 | AAAAAAAUCCCAAAAAAAA | −0.42 | 0.05 | (SEQ ID NO: 161) |
| ANP-Oligo 089 | AAAAAAACUCCAAAAAAAA | −0.42 | 0.07 | (SEQ ID NO: 89) |
| ANP-Oligo 023 | AAAAAAAACUCAAAAAAAA | −0.41 | 0.06 | (SEQ ID NO: 23) |
| ANP-Oligo 004 | AAAAAAAAUAAAAAAAAAA | −0.4 | 0.12 | (SEQ ID NO: 4) |
| ANP-Oligo 158 | AAAAAAAUCACAAAAAAAA | −0.39 | 0.09 | (SEQ ID NO: 158) |
| ANP-Oligo 095 | AAAAAAACUUCAAAAAAAA | −0.39 | 0.07 | (SEQ ID NO: 95) |
| ANP-Oligo 120 | AAAAAAAGCUGAAAAAAAA | −0.38 | 0.04 | (SEQ ID NO: 120) |
| ANP-Oligo 064 | AAAAAAACCAUAAAAAAAA | −0.38 | 0.09 | (SEQ ID NO: 64) |
| ANP-Oligo 052 | AAAAAAACAAUAAAAAAAA | −0.37 | 0.12 | (SEQ ID NO: 52) |
| ANP-Oligo 016 | AAAAAAAACAUAAAAAAAA | −0.37 | 0.14 | (SEQ ID NO: 16) |
| ANP-Oligo 177 | AAAAAAAUGGGAAAAAAAA | −0.35 | 0.08 | (SEQ ID NO: 117) |
| ANP-Oligo 048 | AAAAAAAAUUGAAAAAAAA | −0.35 | 0.1 | (SEQ ID NO: 48) |
| ANP-Oligo 091 | AAAAAAACUCUAAAAAAAA | −0.33 | 0.07 | (SEQ ID NO: 91) |
| ANP-Oligo 038 | AAAAAAAAUACAAAAAAAA | −0.32 | 0.13 | (SEQ ID NO: 38) |
| ANP-Oligo 028 | AAAAAAAAGAUAAAAAAAA | −0.32 | 0.08 | (SEQ ID NO: 28) |
| ANP-Oligo 111 | AAAAAAAGCAGAAAAAAAA | −0.32 | 0.12 | (SEQ ID NO: 111) |
| ANP-Oligo 031 | AAAAAAAAGCUAAAAAAAA | −0.32 | 0.12 | (SEQ ID NO: 31) |
| ANP-Oligo 093 | AAAAAAACUGGAAAAAAAA | −0.31 | 0.04 | (SEQ ID NO: 93) |
| ANP-Oligo 025 | AAAAAAAACUUAAAAAAAA | −0.31 | 0.08 | (SEQ ID NO: 25) |
| ANP-Oligo 150 | AAAAAAAUACGAAAAAAAA | −0.3 | 0.12 | (SEQ ID NO: 150) |
| ANP-Oligo 067 | AAAAAAACCCUAAAAAAAA | −0.3 | 0.1 | (SEQ ID NO: 67) |
| ANP-Oligo 045 | AAAAAAAAUGGAAAAAAAA | −0.29 | 0.13 | (SEQ ID NO: 45) |
| ANP-Oligo 159 | AAAAAAAUCAGAAAAAAAA | −0.28 | 0.09 | (SEQ ID NO: 159) |
| ANP-Oligo 073 | AAAAAAACCUUAAAAAAAA | −0.28 | 0.07 | (SEQ ID NO: 73) |
| ANP-Oligo 137 | AAAAAAAGUCCAAAAAAAA | −0.27 | 0.05 | (SEQ ID NO: 137) |

TABLE 4-continued

Adjusted IL-12 indices of the 193 ssRNA oligonucleotide library

| Name | Adjusted Sequence | IL-12 index Mean | SEM | |
|---|---|---|---|---|
| ANP-Oligo 083 | AAAAAAACGUCAAAAAAAA | -0.27 | 0.11 | (SEQ ID NO: 83) |
| ANP-Oligo 165 | AAAAAAAUCGGAAAAAAAA | -0.26 | 0.17 | (SEQ ID NO: 165) |
| ANP-Oligo 103 | AAAAAAAGACUAAAAAAAA | -0.25 | 0.09 | (SEQ ID NO: 103) |
| ANP-Oligo 012 | AAAAAAAAUGAAAAAAAAA | -0.23 | 0.11 | (SEQ ID NO: 12) |
| ANP-Oligo 061 | AAAAAAACAUUAAAAAAAA | -0.23 | 0.08 | (SEQ ID NO: 61) |
| ANP-Oligo 043 | AAAAAAAAUCUAAAAAAAA | -0.22 | 0.1 | (SEQ ID NO: 43) |
| ANP-Oligo 035 | AAAAAAAAGUCAAAAAAAA | -0.22 | 0.14 | (SEQ ID NO: 35) |
| ANP-Oligo 084 | AAAAAAACGUGAAAAAAAA | -0.2 | 0.07 | (SEQ ID NO: 84) |
| ANP-Oligo 107 | AAAAAAAGUACAAAAAAAA | -0.2 | 0.11 | (SEQ ID NO: 107) |
| ANP-Oligo 010 | AAAAAAAAGUAAAAAAAAA | -0.16 | 0.1 | (SEQ ID NO: 10) |
| ANP-Oligo 070 | AAAAAAACCGUAAAAAAAA | -0.16 | 0.06 | (SEQ ID NO: 70) |
| ANP-Oligo 146 | AAAAAAAUAACAAAAAAAA | -0.16 | 0.14 | (SEQ ID NO: 146) |
| ANP-Oligo 163 | AAAAAAAUCCUAAAAAAAA | -0.15 | 0.09 | (SEQ ID NO: 163) |
| ANP-Oligo 096 | AAAAAAACUUGAAAAAAAA | -0.14 | 0.09 | (SEQ ID NO: 96) |
| ANP-Oligo 036 | AAAAAAAAGUGAAAAAAAA | -0.12 | 0.17 | (SEQ ID NO: 36) |
| ANP-Oligo 164 | AAAAAAAUCGCAAAAAAAA | -0.1 | 0.08 | (SEQ ID NO: 164) |
| ANP-Oligo 097 | AAAAAAACUUUAAAAAAAA | -0.1 | 0.1 | (SEQ ID NO: 97) |
| ANP-Oligo 079 | AAAAAAACGCUAAAAAAAA | -0.09 | 0.1 | (SEQ ID NO: 79) |
| ANP-Oligo 013 | AAAAAAAAUUAAAAAAAAA | -0.09 | 0.12 | (SEQ ID NO: 13) |
| ANP-Oligo 185 | AAAAAAAUUCCAAAAAAAA | -0.08 | 0.14 | (SEQ ID NO: 185) |
| ANP-Oligo 186 | AAAAAAAUUCGAAAAAAAA | -0.08 | 0.09 | (SEQ ID NO: 186) |
| ANP-Oligo 049 | AAAAAAAAUUUAAAAAAAA | -0.07 | 0.07 | (SEQ ID NO: 49) |
| ANP-Oligo 039 | AAAAAAAAUAGAAAAAAAA | -0.05 | 0.15 | (SEQ ID NO: 39) |
| ANP-Oligo 040 | AAAAAAAAUAUAAAAAAAA | -0.04 | 0.22 | (SEQ ID NO: 40) |
| ANP-Oligo 087 | AAAAAAACUAGAAAAAAAA | -0.03 | 0.09 | (SEQ ID NO: 87) |
| ANP-Oligo 092 | AAAAAAACUGCAAAAAAAA | 0 | 0.06 | (SEQ ID NO: 92) |
| ANP-Oligo 100 | AAAAAAAGAAUAAAAAAAA | 0.01 | 0.19 | (SEQ ID NO: 100) |
| ANP-Oligo 022 | AAAAAAAACGUAAAAAAAA | 0.02 | 0.12 | (SEQ ID NO: 22) |
| ANP-Oligo 076 | AAAAAAACGAUAAAAAAAA | 0.02 | 0.06 | (SEQ ID NO: 76) |
| ANP-Oligo 138 | AAAAAAAGUCGAAAAAAAA | 0.02 | 0.18 | (SEQ ID NO: 138) |
| ANP-Oligo 139 | AAAAAAAGUCUAAAAAAAA | 0.05 | 0.08 | (SEQ ID NO: 139) |
| ANP-Oligo 112 | AAAAAAAGCAUAAAAAAAA | 0.08 | 0.12 | (SEQ ID NO: 112) |
| ANP-Oligo 108 | AAAAAAAGUAGAAAAAAAA | 0.08 | 0.16 | (SEQ ID NO: 108) |
| ANP-Oligo 160 | AAAAAAAUCAUAAAAAAAA | 0.1 | 0.14 | (SEQ ID NO: 160) |
| ANP-Oligo 118 | AAAAAAAGCGUAAAAAAAA | 0.1 | 0.14 | (SEQ ID NO: 118) |
| ANP-Oligo 127 | AAAAAAAGGCUAAAAAAAA | 0.11 | 0.09 | (SEQ ID NO: 127) |
| ANP-Oligo 182 | AAAAAAAUUACAAAAAAAA | 0.11 | 0.13 | (SEQ ID NO: 182) |

TABLE 4-continued

Adjusted IL-12 indices of the 193 ssRNA oligonucleotide library

| Name | Adjusted Sequence | IL-12 index Mean | SEM | |
|---|---|---|---|---|
| ANP-Oligo 131 | AAAAAAAGGUCAAAAAAAA | 0.12 | 0.16 | (SEQ ID NO: 131) |
| ANP-Oligo 115 | AAAAAAAGCCUAAAAAAAA | 0.15 | 0.08 | (SEQ ID NO: 115) |
| ANP-Oligo 187 | AAAAAAAUUCUAAAAAAAA | 0.18 | 0.12 | (SEQ ID NO: 187) |
| ANP-Oligo 044 | AAAAAAAAUCGAAAAAAAA | 0.2 | 0.09 | (SEQ ID NO: 44) |
| ANP-Oligo 106 | AAAAAAAGAGUAAAAAAAA | 0.21 | 0.22 | (SEQ ID NO: 106) |
| ANP-Oligo 037 | AAAAAAAAGUUAAAAAAAA | 0.21 | 0.17 | (SEQ ID NO: 37) |
| ANP-Oligo 058 | AAAAAAACAGUAAAAAAAA | 0.22 | 0.08 | (SEQ ID NO: 58) |
| ANP-Oligo 171 | AAAAAAAUGAGAAAAAAAA | 0.22 | 0.23 | (SEQ ID NO: 171) |
| ANP-Oligo 109 | AAAAAAAGUAAAAAAAAAA | 0.22 | 0.21 | (SEQ ID NO: 106) |
| ANP-Oligo 121 | AAAAAAAGCUUAAAAAAAA | 0.24 | 0.17 | (SEQ ID NO: 121) |
| ANP-Oligo 191 | AAAAAAAUUUCAAAAAAAA | 0.27 | 0.15 | (SEQ ID NO: 191) |
| ANP-Oligo 156 | AAAAAAAUAUGAAAAAAAA | 0.27 | 0.09 | (SEQ ID NO: 156) |
| ANP-Oligo 147 | AAAAAAAUAAGAAAAAAAA | 0.27 | 0.36 | (SEQ ID NO: 147) |
| ANP-Oligo 149 | AAAAAAAUACCAAAAAAAA | 0.27 | 0.2 | (SEQ ID NO: 149) |
| ANP-Oligo 183 | AAAAAAAUUAGAAAAAAAA | 0.27 | 0.33 | (SEQ ID NO: 183) |
| ANP-Oligo 174 | AAAAAAAUGCGAAAAAAAA | 0.28 | 0.23 | (SEQ ID NO: 174) |
| ANP-Oligo 082 | AAAAAAACGGUAAAAAAAA | 0.29 | 0.2 | (SEQ ID NO: 82) |
| ANP-Oligo 088 | AAAAAAACUAUAAAAAAAA | 0.3 | 0.15 | (SEQ ID NO: 88) |
| ANP-Oligo 151 | AAAAAAAUACUAAAAAAAA | 0.3 | 0.2 | (SEQ ID NO: 151) |
| ANP-Oligo 155 | AAAAAAAUAUCAAAAAAAA | 0.33 | 0.14 | (SEQ ID NO: 155) |
| ANP-Oligo 152 | AAAAAAAUAGCAAAAAAAA | 0.35 | 0.23 | (SEQ ID NO: 152) |
| ANP-Oligo 167 | AAAAAAAUCUCAAAAAAAA | 0.37 | 0.16 | (SEQ ID NO: 167) |
| ANP-Oligo 134 | AAAAAAAGUACAAAAAAAA | 0.42 | 0.24 | (SEQ ID NO: 134) |
| ANP-Oligo 153 | AAAAAAAUAGGAAAAAAAA | 0.42 | 0.31 | (SEQ ID NO: 153) |
| ANP-Oligo 168 | AAAAAAAUCUGAAAAAAAA | 0.45 | 0.16 | (SEQ ID NO: 168) |
| ANP-Oligo 157 | AAAAAAAUAUUAAAAAAAA | 0.46 | 0.22 | (SEQ ID NO: 157) |
| ANP-Oligo 132 | AAAAAAAGGUGAAAAAAAA | 0.47 | 0.1 | (SEQ ID NO: 132) |
| ANP-Oligo 141 | AAAAAAAGUGGAAAAAAAA | 0.5 | 0.45 | (SEQ ID NO: 141) |
| ANP-Oligo 184 | AAAAAAAUUAUAAAAAAAA | 0.56 | 0.33 | (SEQ ID NO: 184) |
| ANP-Oligo 143 | AAAAAAAGUUCAAAAAAAA | 0.56 | 0.29 | (SEQ ID NO: 143) |
| ANP-Oligo 085 | AAAAAAACGUUAAAAAAAA | 0.57 | 0.18 | (SEQ ID NO: 85) |
| ANP-Oligo 193 | AAAAAAAUUUUAAAAAAAA | 0.62 | 0.18 | (SEQ ID NO: 193) |
| ANP-Oligo 124 | AAAAAAAGGAUAAAAAAAA | 0.63 | 0.23 | (SEQ ID NO: 124) |
| ANP-Oligo 192 | AAAAAAAUUUGAAAAAAAA | 0.65 | 0.12 | (SEQ ID NO: 192) |
| ANP-Oligo 189 | AAAAAAAUUGGAAAAAAAA | 0.66 | 0.15 | (SEQ ID NO: 189) |
| ANP-Oligo 135 | AAAAAAAGUAGAAAAAAAA | 0.67 | 0.34 | (SEQ ID NO: 135) |

TABLE 4-continued

Adjusted IL-12 indices of the 193 ssRNA oligonucleotide library

| Name | Adjusted Sequence | IL-12 index Mean | SEM | |
|---|---|---|---|---|
| ANP-Oligo 169 | AAAAAAAUCUUAAAAAAAA | 0.67 | 0.36 | (SEQ ID NO: 169) |
| ANP-Oligo 148 | AAAAAAAUAAUAAAAAAAA | 0.7 | 0.34 | (SEQ ID NO: 148) |
| ANP-Oligo 181 | AAAAAAAUGUUAAAAAAAA | 0.79 | 0.23 | (SEQ ID NO: 181) |
| ANP-Oligo 170 | AAAAAAAUGACAAAAAAAA | 0.86 | 0.39 | (SEQ ID NO: 170) |
| ANP-Oligo 179 | AAAAAAAUGUCAAAAAAAA | 0.9 | 0.23 | (SEQ ID NO: 179) |
| ANP-Oligo 094 | AAAAAAACUGUAAAAAAAA | 0.9 | 0.22 | (SEQ ID NO: 94) |
| ANP-Oligo 046 | AAAAAAAAUGUAAAAAAAA | 0.97 | 0.26 | (SEQ ID NO: 46) |
| ANP-Oligo 140 | AAAAAAAGUGCAAAAAAAA | 0.99 | 0.55 | (SEQ ID NO: 140) |
| ANP-Oligo 136 | AAAAAAAGUAUAAAAAAAA | 1.04 | 0.33 | (SEQ ID NO: 136) |
| ANP-Oligo 173 | AAAAAAAUGCCAAAAAAAA | 1.22 | 0.3 | (SEQ ID NO: 173) |
| ANP-Oligo 142 | AAAAAAAGUGUAAAAAAAA | 1.23 | 0.54 | (SEQ ID NO: 142) |
| ANP-Oligo 180 | AAAAAAAUGUGAAAAAAAA | 1.31 | 0.37 | (SEQ ID NO: 180) |
| ANP-Oligo 145 | AAAAAAAGUUUAAAAAAAA | 1.32 | 0.5 | (SEQ ID NO: 145) |
| ANP-Oligo 133 | AAAAAAAGGUUAAAAAAAA | 1.51 | 0.61 | (SEQ ID NO: 133) |
| ANP-Oligo 154 | AAAAAAAUAGUAAAAAAAA | 1.57 | 0.43 | (SEQ ID NO: 154) |
| ANP-Oligo 190 | AAAAAAAUUGUAAAAAAAA | 1.6 | 0.36 | (SEQ ID NO: 190) |
| ANP-Oligo 188 | AAAAAAAUUGCAAAAAAAA | 1.62 | 0.19 | (SEQ ID NO: 188) |
| ANP-Oligo 175 | AAAAAAAUGCUAAAAAAAA | 1.85 | 0.4 | (SEQ ID NO: 175) |
| ANP-Oligo 172 | AAAAAAAUGAUAAAAAAAA | 1.92 | 0.83 | (SEQ ID NO: 172) |
| ANP-Oligo 034 | AAAAAAAAGGUAAAAAAAA | 2.21 | 0.36 | (SEQ ID NO: 34) |
| ANP-Oligo 176 | AAAAAAAUGGCAAAAAAAA | 2.41 | 0.46 | (SEQ ID NO: 176) |
| ANP-Oligo 178 | AAAAAAAUGGUAAAAAAAA | 3.26 | 0.98 | (SEQ ID NO: 178) |
| ANP-Oligo 144 | AAAAAAAGUUGAAAAAAAA | 4.39 | 2.19 | (SEQ ID NO: 144) |
| ANP-Oligo 166 | AAAAAAAUCGUAAAAAAAA | 4.42 | 0.6 | (SEQ ID NO: 166) |

The invention claimed is:

1. A method for preparing an antisense RNA oligonucleotide having gene silencing activity and high IL-12 inducing activity, comprising the steps of:
   (a) identifying all potential antisense sequences between 18 and 50 nucleotides in length, for a target mRNA;
   (b) identifying antisense sequences that have gene silencing activity;
   (c) identifying antisense RNA sequences from those among identified in step (b) which have an IL-12 score of at least $8.4064 \times n + 66.958$, wherein the IL-12 score is assigned according to the method comprising the steps of:
      (i) identifying all possible 3-nucleotide (3mer) motifs contained in the oligonucleotide;
      (ii) assigning an IL-12 point score for each individual 3mer motif
         (A) for a 3mer motif which appears in Table 5, assign an IL-12 point score according to Table 5;
         (B) for a 3mer motif which does not appear in Table 5, assign an IL-12 point score of 0;
      (iii) assigning the sum of the IL-12 point scores of individual 3mer motifs as the IL-12 score of the oligonucleotide;
      and wherein n is the length of the sequence and n is between 18 and 50;
   (d) decreasing the IL-12 score threshold by 1 if no antisense sequence is identified in step (c), until at least one antisense sequence is identified;
   (e) preparing the antisense RNA identified in step (c) or (d); and
   (f) optionally testing the gene silencing and/or the IL-12 inducing activity of the antisense prepared in (e).

2. A method for preparing an antisense RNA oligonucleotide having gene silencing activity and high IL-12 inducing activity, comprising the steps of:
   (a) identifying all potential antisense sequences between 18 and 50 nucleotides in length for a target mRNA;
   (b) assigning an IL-12 score for all of the potential antisense sequences identified in (a) according to the method comprising the steps of:
      (i) identifying all possible 3-nucleotide (3mer) motifs contained in the oligonucleotide;
      (ii) assigning an IL-12 point score for each individual 3mer motif
         (A) for a 3mer motif which appears in Table 5, assign an IL-12 point score according to Table 5;
         (B) for a 3mer motif which does not appear in Table 5, assign an IL-12 point score of 0; and
      (iii) assigning the sum of the IL-12 point scores of individual 3mer motifs as the IL-12 score of the oligonucleotide;
   (c) identifying 10 potential antisense sequences with the highest IL-12 scores;
   (d) identifying antisense sequences with gene silencing activity among the 10 potential antisense sequences identified in step (c);
   (e) identifying 10 potential antisense sequences with the next highest IL-12 scores if no antisense sequence can be identified in step (d); repeat steps (d) and (e) until at least one antisense sequence is identified;
   (f) preparing the antisense RNA identified in step (d) or (e); and
   (g) optionally testing the gene silencing and/or the IL-12 inducing activity of the antisense RNA prepared in (f).

3. The method of claim 1, wherein the antisense oligonucleotide is at least 80% complementary to the target mRNA.

4. The method of claim 1, wherein the antisense RNA oligonucleotide comprises a 2'-modified ribose.

5. The method of claim 1, wherein the antisense RNA oligonucleotide comprises a phosphorothioate linkage.

6. The method of claim 1, wherein the antisense RNA oligonucleotide comprises a ligand.

7. The method of claim 1, wherein the antisense RNA oligonucleotide is 5'-phosphorylated.

8. The method of claim 1, wherein the antisense RNA oligonucleotide is produced by chemical synthesis.

9. The method of claim 2, wherein the antisense oligonucleotide is at least 80% complementary to the target mRNA.

10. The method of claim 2, wherein the antisense RNA oligonucleotide comprises a 2'-modified ribose.

11. The method of claim 2, wherein the antisense RNA oligonucleotide comprises a phosphorothioate linkage.

12. The method of claim 2, wherein the antisense RNA oligonucleotide comprises a ligand.

13. The method of claim 2, wherein the antisense RNA oligonucleotide is 5'-phosphorylated.

14. The method of claim 2, wherein the antisense RNA oligonucleotide is produced by chemical synthesis.

* * * * *